United States Patent
Godbole et al.

(10) Patent No.: US 6,806,254 B2
(45) Date of Patent: Oct. 19, 2004

(54) METHODS AND MATERIALS RELATING TO ALPHA-2-MACROGLOBULIN-LIKE POLYPEPTIDES AND POLYNUCLEOTIDES

(75) Inventors: Shubhada D. Godbole, Santa Clara, CA (US); Bryan J. Boyle, San Francisco, CA (US); Nancy K. Mize, Mountain View, CA (US); Cenhua Deng, Cupertino, CA (US); Ryle W. Goodrich, San Jose, CA (US); Matthew C. Arterburn, Los Gatos, CA (US); Ping Zhou, Cupertino, CA (US); Y. Tom Tang, San Jose, CA (US); Chenghua Liu, San Jose, CA (US); George Yeung, Mountain View, CA (US); Radoje T. Drmanac, Palo Alto, CA (US)

(73) Assignee: Nuvelo, Inc., Sunnyvale, CA (US)

( * ) Notice: Subject to any disclaimer, the term of this patent is extended or adjusted under 35 U.S.C. 154(b) by 94 days.

(21) Appl. No.: 09/756,247

(22) Filed: Jan. 8, 2001

(65) Prior Publication Data

US 2003/0180722 A1 Sep. 25, 2003

Related U.S. Application Data

(63) Continuation-in-part of application No. 09/649,167, filed on Aug. 23, 2000, now abandoned, which is a continuation-in-part of application No. 09/540,217, filed on Mar. 31, 2000, now abandoned, and application No. 09/756,247, which is a continuation-in-part of application No. 09/684,711, filed on Oct. 6, 2000, now abandoned, which is a continuation-in-part of application No. 09/560,875, filed on Apr. 27, 2000, now abandoned, which is a continuation-in-part of application No. 09/496,914, filed on Feb. 3, 2000, now abandoned.

(51) Int. Cl.$^7$ .................. A61K 38/00; C07K 14/435
(52) U.S. Cl. ........................ 514/12; 530/350
(58) Field of Search ............... 530/23.1, 23.5, 530/350; 514/12

(56) References Cited

U.S. PATENT DOCUMENTS

2002/0090672 A1 * 7/2002 Rosen et al. ............... 435/69.1
2003/0044890 A1 * 3/2003 Rosen et al. ............... 435/69.1

FOREIGN PATENT DOCUMENTS

WO      WO 02/29058 A2 * 4/2002

* cited by examiner

*Primary Examiner*—Marianne P. Allen
(74) *Attorney, Agent, or Firm*—Renee S. Polizotto

(57) ABSTRACT

The invention provides novel polynucleotides and polypeptides encoded by such polynucleotides and mutants or variants thereof that correspond to novel human secreted alpha-2-macroglobulin-like polypeptides. These polynucleotides comprise nucleic acid sequences isolated from cDNA library from fetal brain mRNA (Clontech) (SEQ ID NO: 1) and uterus mRNA (Clontech) (SEQ ID NO: 26). Other aspects of the invention include vectors containing processes for producing novel human secreted alpha-2-macroglobulin-like polypeptides, and antibodies specific for such polypeptides.

2 Claims, 10 Drawing Sheets

BLASTX ALIGNMENT OF SEQ ID NO: 4 ALPHA-2-MACROGLOBULIN-LIKE POLYPEPTIDE WITH HUMAN ALPHA-2-MACROGLOBULIN PRECURSOR SEQ ID NO: 23

```
Query: Alpha-2-macroglobulin polypeptide(SEQ ID NO: 4)
Subject: gi|4557225 ref|NP_000005.1| alpha-2-macroglobulin precursor sp|P01023|A2MG_HUMAN ALPHA-2-MACROGLOBULIN
PRECURSOR (ALPHA-2-M) pir||MAHU alpha-2-macroglobulin precursor - human >gb|AAA51551.1| (M11313) alpha-2-macroglobulin
precursor [Homo sapiens] (SEQ ID NO: 23)
Length = 1474

Score = 2714 (960.4 bits), Expect = 1.7e-281, P = 1.7e-281
Identities = 596/1494 (39%), Positives = 874/1494 (58%)

Query:    13  LLLGM_ALSPAIAEELPNVLVTLPARLNFPSVQKVCLDLSPGYSDVKFTVTLETKDKTQK  192
              LLL +L      +++ + P Y+V +P+ L+   + ++K C+ LS   V   +LE+       +
Sbjct:    14  LLLVLLPTDASVSGK-PQYMVLVPSLLHTETTEKGCVLLSYLNETVTVSASLESVRGNRS   72

Query:   193  LLEYSGLKKRHLHCISFLVPPAGGTEEVATIRVSGVGNNISFEEKKKVLIQRQGNGTPV   372
              L    + LHC++F VP +   EEV  V  G   F+++ + +    FV
Sbjct:    73  LFTDLEAENDVLHCVAFAVPK-SSSNEEVMFLTVQVKGPTQEFKKRTTVMVKNEDSLVFV  131

Query:   373  QTDKPLYTPGQQVYFRIVTMDSNFVPVNDKYSMVELQDPNSNRIAQWLEVVPEQGIVDLS   552
              QTDK +Y PGQ V FR+V+MD NF P+N+    +V +QDP  NRIAQW      E G+   S
Sbjct:   132  QTDKSIYKPGQTVKFRVVSMDENFHPLNELIPLVYIQDPKGNRIAQWQSFQLEGGLKQFS   191

Query:   553  FQLAPEAMLGTYTVAVAE---GKTFGTFSVFEYVLPKFKVEVVEPKELSTVQESFLVXIC   723
              F L+ E    G+Y V V +    G+T      F+VEE+VLPKF+V+V  PK +  +++E  V +C
Sbjct:   192  FPLSSEPFQGSYKVVVQKKSGGRTEHPFTVEEFVLPKFEVQVTVPKI=TLEEEMNVSVC   251

Query:   724  CRYTYGKPMLGAVQVSVCQKANTVWYREVEREQLPDKCRNLSGQTDKTGCFSAPVDMATF   903
                      YTYGKP+ G V VS+C+K +       +          E   C  SGQ + GCF   V     F
Sbjct:   252  GLYTYGKPVPGHVTVSICRKYSDA--SDCHGEDSQAFCEKFSGQLNSHGCFYQQVK=KVF   309

Query:   904  DLIGYAYSHQINIVATVVEEGTGVEANATQNIYISPQMGSMTFEDTSNFYHPNFPFSGKI  1083
              QL +   Y  ++ A + EEGT VE      Q+ I+ ++    PF G++
Sbjct:   310  QLKRKEYEMKLHTEAQIQFRGTVVELTGRQSSEITRTITKLSFVKVDSHFRQGIPFFGQV   369

Query:  1084  RVRGHDDSFLKNHLVFLVIYGTNGTFNQTLVLVIDNNGLAPHTLETSGWNGTDVSLEGKTQM  1263
              R+     + N  +F 1 G       TD +GL  F++ T+   GT   ++
Sbjct:   370  RLVDGKGVPIPNKVIF--IRGNEANYYSNATTDEHGLVQFSINTTNVMGTSLTVRVNYKD   427

Query:  1264  EDLVYNPEQVPRYYQNAYLHLRPFYSTRSFLG=HRLNGPLKCCGQPQEVLVDYYIDPADA  1443
              Y + V    +S +    +S ++SF+ +     ++  L CG  Q V      Y ++
Sbjct:   428  RSPCYGYQWVSEEHEEAHHTAYLVFSPSKSFVHLEPMSHELPCGHTQTVQAHYITNGGTL   487
```

Fig 1A

BLASTX ALIGNMENT OF SEQ ID NO: 4 ALPHA-2-MACROGLOBULIN-LIKE POLYPEPTIDE WITH
HUMAN ALPHA-2-MACROGLOBULIN PRECURSOR SEQ ID NO: 23

```
Query:  1444  SPDQEISPSYYLIGKGSLVMEGQKHLNSKKKGLKASFSLSLTFTSRLAPDPSLVIYAIFP   1623
              +++SF Y ++ KG +V  G  L  K++ +K  FS+S+   S  -AP   L+IYA+ P
Sbjct:  488   LGLKKLSFYLIMAKGGIVRTGTHGLLVKQEMKGHFSISIPVKSD-APVARLLIYAVLP    547

Query:  1624  SGGVVADKIQFSVGMCFDNQVSLGFSPSPSQQLPGAEVELQLQAAPGSLCALRAVDESVLLL 1803
              +G V+ D ++ V C  N+V L FSPSQ LP +    L++ AAP S+CALRAVD+SVLL+
Sbjct:  548   TGDVIGDSAKYDVENCLANKVDLSFSPSQSLPASHAHLRVTAAPQSVCALRAVDQSVLLM   607

Query:  1804  RPDRELSNRSVYCMFPFWYGHYPYQVAEYDQCPVSGPWDFPQPLIDPMPQGESSQRSIIW   1983
              +PD ELS   SVY + P                E D   GP +  Q    D ++ +    I +
Sbjct:  608   KPDAELSASSVYNLLP-------------EKDLTGFPGPLN-DQDEDCINRHNVYINGITY 655

Query:  1984  RP-SFSEGTDLFSFFRDVGLKILSNAKIKKPVDCSH------RSPE------YSTAMGGG  2124
              P S + D++SF  D+GLK  +N+KI+KP  C              PE          Y + + G
Sbjct:  656   TPVSSTNEKDMYSFLEDMGLKAFTNSKIRKPMCPQLQQYEMHGPEGLRVGFYESDVMGR   715

Query:  2125  GHPEAFESSTPLHQAEDSQVRQYFPETWLWDLFPIGNSCKEAVHVTVPDA-TEWKAMSFC  2304
              GH          P H        VR+YFPETW+WDL +   ++G   V VTVPD ITEWKA +FC
Sbjct:  716   GHARLVHVEEP-HT--ETVRKYFPETWIWDLVVVNSAGVAFVGVTVPDTITEWKAGAFC   771

Query:  2305  TSQSRGFGLSPTVGLTAFKPFFVDLTLPYSVVRGESFRLTATIFNYLKDCIRVQTDLAKS  2484
              S+  G G+S T  L AF +PFFV+LT+P+SV+ RGE+F L AT+ NYL  CIRV   L  S
Sbjct:  772   LSEDAGLGLSSTASLRAFQPFFVELTMPYSVIRGEAFTLKATVLNYLPKCIRVSVQLEAS   831

Query:  2485  HFYQIESWADSQTSSCLCADDAKTHHWNITAVKLGHINFPTISTKILLDSNEPCCGQKGFVP  2664
                                  Q   C+CA+   T  W +T    LG++NFT+S + L+S  CG +    VP
Sbjct:  832   PAFLAVPVEKEQAPHCICANGRQTVSWAVTPKSLGNVNFTVSAEALESQELCGTEVPSVP   891

Query:  2665  QKGRSDTLIKPVLVKPEGVLVEKTHSSLLCPKGKVASESVSLELPVDIVPDSTKAYVTVL  2844
              + GR DT+KP+LV+PEG+  E T  +SLLCP G   SE +SL+LP ++V +S +A V+VL
Sbjct:  892   EHGRKDTVIKPLLVEPEGLEKETTFNSLLCPSGGEVSEELSLKLPPNVVEESARASVSVL   951

Query:  2845  GKQLEILDSERKRRMEAAKVWRDIMGTALQNLDGLVQMPSGGCGEQNMVLFAPIIYVLQYL  3024
                             DI+G+A+QN    L+QMP GCGEQNMVLFAP IYVL YL
Sbjct:  952   G-------DILGSAMQNTQNLLQMPYGCGEQNMVLFAPNIYVLDYL            990

Query:  3025  EKAGLLTEEIRSRAVGFLEIGYQKELMYKHSNGSYSAPFGERDGN--GNTWLTAFVTKCFG  3198
              +      LT E++S+A+G+L  GYQ++L YKH +GSYS FGER G  GNTWLTAFV K F
Sbjct:  991   NETQQLTPEVRSKAIGYLNTGYQRQLNYKHYDGSYSTFGERYGRNQGNTWLTAFVLKTFA   1050
```

Fig. 1B

BLASTX ALIGNMENT OF SEQ ID NO: 4 ALPHA-2-MACROGLOBULIN-LIKE POLYPEPTIDE WITH
HUMAN ALPHA-2-MACROGLOBULIN PRECURSOR SEQ ID NO: 23

```
Query:  3199  QAQKFIFIDPKNIQDALKWMAGNQLPSGCYANVGNLLHTAMKGGVDDFVSLTAYVTAALL  3378
              QA+ +IFID  +I  AL W++  Q   +GC+ + G+LL+ A+KGGV+DEV+L+AY+T ALL
Sbjct:  1051  QARAYIFIDEAHITQALIWLSQRQKDNGCFRSSGSLLNNAIKGCVEDEVTLSAYITIALL  1110

Query:  3379  EMGKDVDDPMVSQGLRCLKNSATST------TNLYTQALLAYIFSLAGEMDIRNILLKQ  3537
              E+    V P+V  L CL+ SA    T      ++++YT+ALLAY F+LAG  D R  +LK
Sbjct:  1111  EIPLTVTHPVVRNALFCLE-SAWKTAQEGDHGSHVYTKALLAYAFALAGNQDKRKEVLKS  1169

Query:  3538  LDQQAIISGESIYWSQKPTPSSNASPWSEPAA--VDVELTAYALLAQLT-KPSLTQKEIA  3708
              L+++A+   S++W +  P +   + P  + EP A     +VE+T+Y LLA LT +P+ T +++
Sbjct:  1170  LNEEAVKKDNSVHWERPQKPKAPVGHFYFPQAPSAEVEMTSYVLLAYLTAQPAPTSEDLT  1229

Query:  3709  KATSIVAWLAKQHNAYGGFSSTQDTVVALQALAKY-ATTAYMPSEEINLVVKSTENFQRT  3885
              +AT+IV W+ KQ NA GGFSSTQDTVVAL AL+KY A T        + + ++S+   F
Sbjct:  1230  SATNIVKWITKQQNAQGGFSSTQDTVVALHALSKYGAATFTRTGKAAQVTIQSSGTFSSK  1289

Query:  3886  FNIQSVNRLVFQQDTLPNVPGMYTLEASGQGCVYQTVLRYNILPPTNMKTFSLSVEIGK  4065
              F + + NRL+ QQ +LP +PG Y+++ +G+GCVY +QT L+YN+LP       F+L V+
Sbjct:  1290  FQVDNNNRLLLQQVSLPELPGEYSMKVTGEGCVYLQTSLKYNILPEKEEFPFALGVQTLP  1349

Query:  4066  ARCEQPTSPRSLTLTHTSYVGSRSSSNMAIVEVKMLSGFSPMEGTNQLLLQQPLVKKVE  4245
              C++P + S    +++  SY   GSR3+SNMAIV+VKM+SGF P++ T  ++L   V + E
Sbjct:  1350  QTCDEPKAHTSFCISLSVSYTGSRSASNMAIVDVKMVSGFIPLKPTVKMLERSNHVSRTE  1409

Query:  4246  FGTDTLNIYLDELIKNTQTYTFT+SQSVLVTNLKPATIKVYDYYLPGSFKLSQY  4407
              ++ + IYLD++  T + FT+ Q V V +LKPA +KVYDY   F +++Y
Sbjct:  1410  VSSNHVLIYLDKVSNQTLSLFPTVLQDVPVRDLKPAIVKVYDYYETDEFAIAEY  1463
```

FIG. 1C

BLASTX ALIGNMENT OF SEQ ID NO: 4 ALPHA-2-MACROGLOBULIN-LIKE POLYPEPTIDE WITH
RECOMBINANT HUMAN ALPHA-2-MACROGLOBULIN SEQ ID NO: 24

```
Query: Alpha-2-macroglobulin polypeptide(SEQ ID NO: 4)
Subject: sp|R11334|R11334 Recombinant human alpha-2 macroglobulin. (SEQ ID NO 24)
Length = 1474

Score = 2699 (955.2 bits), Expect = 3.2e-280, P = 3.2e-280
Identities = 596/1494 (39%), Positives = 870/1494 (58%)

Query:   13  LLLGMLALSPAIAEELPNYLVTLPARLNFPSVQKVCLDLSPGYSDVKFTVTLETKDKTQK    192
             LLL +L  + A     P Y+V +P+ L+   +K C+ LS     V  + +LE+    +
Sbjct:   13  LLLVLVPTDASVSGKPQYMVLVPSLLHTETTEKGCVLLSYLNETVTVSASLESVRGNRS    72

Query:  193  LLEYSGLKKRHLHCISFLVPPAGTEEVATIRVSGVGNNISFEEKKKVLIQRQNGTFV    372
             L    +  LHC++F VP +    EEV  + V  G     F+++  V+++ + + FV
Sbjct:   73  LFTDLEAENDVLHCVAFAVPK-SSSNEEVMFLTVQVKGFTQEFKKRTTVMVRNEDSLVFV    131

Query:  373  QTDKPLYTPGQQVYFRIVTMDSNFVPVNDKYSMVELQDPNSNRIAQWLEVPEQGIVDLS    552
             QTDK +Y PGQ V FR+V+MD NF P+N+    +V +QDP NRIAQW      E G+   S
Sbjct:  132  QTDKSIYKPGQTVKFRVVSMDENFH2LNELIPLVYIQDPKGNRIAQWQSFQLEGGLKQFS    191

Query:  553  FQLAPEAMLGTYTVAVAE---GKTFGTFSVEEYVLPKFKVEVVPKELSTVQESFLVKIC    723
             F L+ E   G+Y V V  +   G+T   F+VEE+VLPKF+V+V  PK ++ +E  V +C
Sbjct:  192  FPLSSEPFQGSYKVVVQKKSGGRTEHPFTVEEFVLPKFEVQVTVPKIITILEEMNVSVC    251

Query:  724  CRYTYGKPMLGAVCSVCQKANTYWYREVEREQLPDKCRNLSGQTDKTGCFSAPVDMATF    903
             YTYGKP+ G V VS+C+K +    +    E     C     SCQ +  GCF  V    F
Sbjct:  252  GLYTYGKFVTGHVTVSICRKYSDA--SDCHGEDSQAFCEKFSGQLNSHGCFYQQVKTKVF    309

Query:  904  DLIGYAYSHQINIVATVVEEGTGVEANATQNIYISPQMGSMTFEDTSNFYHPNFPFSGKI    1083
             L     Y +++  A + EEGT VE    Q+ I+     +  F    PF G++
Sbjct:  310  QLKRKEYEMKLHTEAQIQEEGTVVELTGRQSSEITRTITKLSFVKVDSHFRQGIPFFGQV    369

Query: 1084  RVRGHDDSFLKNHLVFLVIYGTNGTFNQTLVTDNNGLAPFTLETSGWNGTTVSLEGKFQM    1263
             R+    +  + N ++F  I G      +    TD +GL F++ T+  GT +++ ++
Sbjct:  370  RLVDGKGVPIPNKVIF--IRGNEANYYSNACTDEIGLVQPSINTTNVMGTSLTVRVNYKD    427

Query: 1264  EDLVYNPEQVPRYYQNAYLHLRPFYSTTRSFLGIHRLNGPLKCGQPQEVLVDYYIDPADA    1443
              Y +V A+   +SF+ ++ +S ++SF+ +++ L CG  Q V  Y  ++
Sbjct:  428  RSPCYGYQWVSEHEEAHHTAYLVFSPSKSFVHLEPMSHELPCGHTQTVQAHYILNGGTL    487

Query: 1444  SPDQEISFSFYYLIGKGSLVMEGQXHLNSKKKGLKASFSLSLTFTSRLAPDPSLVIYAIFP    1623
             +++SF Y ++ XG +V G   L  K++ +K  FS+S+   S +AP  L+IYA+  P
Sbjct:  488  LGLKKLSFYYLIMAKGGIVRTGTHGLLVKQEDMKGHFSISIPVKSDIAPVARLLIYAVLP    547
```

Fig. 2A

BLASTX ALIGNMENT OF SEQ ID NO: 4 ALPHA-2-MACROGLOBULIN-LIKE POLYPEPTIDE WITH
RECOMBINANT HUMAN ALPHA-2-MACROGLOBULIN SEQ ID NO: 24

```
Query: 1624 SGGVVADKIQFSVGMCFDNQVSLGFSPSQCLPGAEVELQLQAAPGSLCALRAVDESVLLL 1803
            +G V+ D  ++ V C  N+V L FSPSQ LP +    L++ AAP S+CALRAVD+SVLL+
Sbjct:  548 TGDVLGDSAKYDVENCLANKVDLSFSPSQSLPASHAHLRVTAAPQSVCALRAVDQSVLLM  607

Query: 1804 RDDRELSNRSVYGMFPFWYGHPYPYQVAEYDQCPVSGPWDFPQPLIDPMPQGHSSQRSIIW 1983
            +PD ELS   SVY + P           E D      GP +  Q  D + + +     I +
Sbjct:  608 KPDAELSASSVYNLLP----------EKDLTGFPGPLN-DQDEECINRHNVYINGITY    655

Query: 1984 RP-SFSEGTDLFSFFRDVGLKILSNAKIKKPVDCSH--------RSPE------YSTAMGGG 2124
            P  S +  D++SF  D+GLK  +N+KI+KP  C        PE       Y + + G
Sbjct:  656 TPVSSTNEKDMYSFLEDMGLKAFTNSKIRKPKMCPQLQQYEMHGEGLRVGFYESDVMGR    715

Query: 2125 GHPEAFESSTPLHQAEDSQVRQYFPETWLWDLFPIGNSGKEAVHVTVPDAITEWKAMSFC 2304
            GH      P H           VR+YF  ETW+WDL +  ++G     V TVPD ITEWKA +FC
Sbjct:  716 GHARLVHVEEP-HT----ETVRKYFAETWIWDLVVVNSAGVAEWGVTVPDTITEWKAGAFC  771

Query: 2305 TSQSRGFGLSPTVGLTAFKPFFVDLTLPYSVVRGESFRLTATIFNYLKDCIRVQTDLAKS 2484
            S+   G G+S T L AF+ PFFV+LT+ PYSV+RGE+F L AT+ NYL  CIRV    L S
Sbjct:  772 LSEDACLGISSTASLRAFQPFFVELTMPYSVIRGEAFTLKATVLNYLPKCIRVSVQLEAS  831

Query: 2485 HEYQLESWADSQTSSCLCADDAKTHWMNITAVKLGHINFTISTKILDSNEPCGGQKGFVP 2664
                    +      Q     C+CA+   T   W +T   LG++NFT+S +  L+S E CG +    VP
Sbjct:  832 PAFLAVPVEKEQAPHCICANGRQTVSWAVTPKSLGNVNFTVSAEALESQELCGTEVPSVP  891

Query: 2665 QKGRSDTLIKPVLVKPEGVLVEKTHSSLLCPKGKVASESVSLELPVDIVPDSTKAYVTVL 2844
            + GR DT+IKP+LV+PEG+     E T  +SLLCP G   SE +SL+LP ++V +A V+VL
Sbjct:  892 EHGRKDTVIKPLLVEPEGLEKETTFNSLLCPSGGEVSEELSLKLPNVVEESARASVSVL  951

Query: 2845 GKQLEILDSERKRRMEAAKVWRDIMGTALQMLDGLVQMPSGCGEQNMLFAPIIYVLQYL 3024
                          DI+G+A+QN    L+QMP GCGEQNMVLFAP IYVL Y+
Sbjct:  952 G----------DILGSAMQNTQNLLQMPYGCGEQNMVLFAPNIYVLDYL  990

Query: 3025 EKAGLLTEEIKSRAVGPLEIGYQKELMYKHSNGSYSAFGERDGN--GNTWLTAFVTKCFG 3198
            +     L T EI+S+A+G+L  GYQ++L YKH +GSYS FGER G   GNTWLTAFV K F
Sbjct:  991 NETQQLTPEIKSKAIGYLNTGYRQLNYKHYDGSYSTFGERYGRNQGNTWLTAFVLKTFA 1050

Query: 3199 QAQKFIFIDPKNIQDALKWMAGNQLPSGCYANVGNLLHTAMKGGVDDEVSLTAYVTAALL 3378
            QA+ +IFID +I  AL W++    Q   +GC+    +GLL+ A+KGGV+DEV+L+AY+T ALL
Sbjct: 1051 QARAYIFIDEAHTQALIWLSQRQKDNGCFRSSGSLLNNAIKGGVEDEVTLSAYITIALL 1110
```

Fig. 2B

BLASTX ALIGNMENT OF SEQ ID NO: 4 ALPHA-2-MACROGLOBULIN-LIKE POLYPEPTIDE WITH
RECOMBINANT HUMAN ALPHA-2-MACROGLOBULIN SEQ ID NO: 24

```
Query:  3379  EMGKDVDDPMVSQGLRCLKMSATST------TNLYTQALLAYIFSLAGEMDIRNILLKQ  3537
              E+   V  P+V   L CL+ SA   T         +++YT+ ALLAY F+LAG  D R  +LK
Sbjct:  1111  EILLTVTHPVVRNALFCLE-SAWKTAQEGDHGSHVYTKALLAYAFALAGNQDKRKEVLKS  1169

Query:  3538  LDQQAIISGESIYWSQKPTPSSNASPWSEPAA--VDVELTAYALLAQLT-KPSLTQKEIA  3708
              L+++A+    S++W  +  P +     + FP A    +VE+T+Y LLA LT +P! T +++
Sbjct:  1170  LNEEAVKKDNSVHWERPQKPKAPVGHFYEPQAPSAEVEMTSVLLAYLTAQPAPTSEDLT   1229

Query:  3709  KATSIVAWLAKQHNAYGGFSSTQDTVVALQALAKY-ATTAYMPSEEINLVVKSTENFQRT  3885
              A!+1V W+ KQ NA GGFSSTQ TVVAL AL+KY A T      +   + ++S+  F
Sbjct:  1230  SATNIVKWITKQQNAQGFSSTQHTVVALHALSKYGAATFTRTGKAAQVT-QSSGTFSSK   1289

Query:  3886  FNIQSVNRLVFQQDTLPNVPGMYTLEASGQGCVYVQTVLRYNILPPTNMKTFSLSVEIGK  4065
              F + + NRL+ QQ +LP +PG Y+++ +G+GCVY+QT L+YNIIP        F+L V+
Sbjct:  1290  FQVDNNNRLLLQQVSLPELPGEYSMKVTGFGCVYLQTSLKYNILPEKEEFPFALGVQTLP  1349

Query:  4066  ARCEQPTSPRSLTLTIHTSYVGSRSSSNMAIVEVEVKMLSGFSPMEGTNQLLLQQPLVKKVE  4245
              C++P + S  +++ SY  GSRS+ SNMAIV+VKM+SGF P++ T  ++L +   V + E
Sbjct:  1350  QTCDEPKAHTSFQISLSVSYTGSRSASNMAIVDVKMVSGFIPLKPTVKMLERSNHVSRTE  1409

Query:  4246  FGTDTINIYLDELIKNTQTYTFTISQSVLVTNLKPATIKVYDYYLPGSFKLSQY  4407
              ++   + IYLD++   T +  FT+ Q V V +LKPA +KVYDY   F +++Y
Sbjct:  1410  VSSNHVLIYLDKVSNQTLSLFFTVLQDVPVRDLKPAIVKVYDYYETDEFATAEY  1463
```

FIG. 2C

BLASTX ALIGNMENT OF SEQ ID NO: 29 ALPHA-2-MACROGLOBULIN-LIKE POLYPEPTIDE WITH OVOS_CHICK OVOSTATIN PRECURSOR SEQ ID NO: 41

```
Query: Alpha-2-macroglobulin polypeptide (SEQ ID NO: 29)
Subject: >sp|P20740|OVOS_CHICK OVOSTATIN PRECURSOR (OVOMACROGLOBULIN) >pir||A20872 ovostatin precursor - chicken
         >emb|CAA55384.1| (X78801) ovomacroglobulin, ovostatin [Gallus gallus] (SEQ ID NO: 41)
Length = 1473

Score = 1300 (462.7 bits), Expect = 6.1e-135, Sum P(2) = 6.1e-135
Identities = 297/849 (34%), Positives = 457/849 (53%), Frame = +3

Query:   96 VYKFVPVSPTKMWAQLLLGMLALSPAIAEEL-PNYLVTLPARLNFPSVQKVCLDLSPGYS 272
             + +  ++ KMW + +L +L A +E  P Y++ +PA L   S   +VCL
Sbjct:    9 TLSFFCLTVRKMWLKFILAILLLHAAACKEFEPQYVLMVPAVLQSDSPSQVCLQFFNLNQ 68

Query:  273 DVKFTVTLETKDTQKLLEYSGLKKRHLHCISFLVPPAGGTEEVATIRVSGVGNNISFE 452
               V LE       +E +       L  C++F+++P      +A I   G     +
Sbjct:   69 TISVRVVLEYDTINTIFEKNTTTSNGLQCLNFMIPPVT--SVSLAFISFTAKGTTFDLK 126

Query:  453 EKKKVLIQRQGNGTFVQTDKPLYTPGQQVYFRIVTMDSNFVPVNDKYSMVELQDPNSNRI 632
            E++  V+I    + FVQTDKP+Y PGQ V FR+V +D NF PV + +QDP +NRI
Sbjct:  127 ERRSVMIWNMESFVFVQTDKPIYKPGQSVMFRVVALDFNFKPVQEMYPLIAVQDPQNNRI 186

Query:  633 AQWLEVVPEQGIVDLSFQLAPEAMLGTYTVAVAE--G-KTFGTFSVEEYVLPKFKVEVVR 803
            QW V E  IV +  F L E +LG Y + V +  G +T   +F VEEYVLPKF V V
Sbjct:  187 FQWQNVTSEINIVQIEFPLTERPILGNYKIIVTKKSGERTSHSFLVEEYVLPKFDVTVTA 246

Query:  804 PKELSTVQESFLVKICCRYTYGKPMLGAVQVSVCQKANTYWYREVEREQLPDKCRNLSGQ 983
            P L+ +     VKIC  YTYG+P+ G VQ+SVC+  ++Y   R +     C+++  +
Sbjct:  247 PGSLTVMDSELTVKICAVYTYGQPVEGKVQLSVCRDFDSYG---RCKKSPVCQSFTKD 301

Query:  984 TDKTGCFSAPVDMATFDLIGYAYSHQINIVATVVEEGTGVEANATQNIYISPQMGSMTFE 1163
             D  GC S  +     F+L   Y   +++ A V E+       ATQ+I I+  M S+ FE
Sbjct:  302 LDTDGCLSHILSSKVFELNRIGYKRNLDVKAIVTEKEQVCNLTATQSISTTQVMSSLQFE 361

Query: 1164 DTSNFYHPNFPFSGKIRVRGHDDSFLKNHLVFLVIVGTNGTFNQTLVTDNNGLAPFTLET 1343
             + Y  P+G+I++   D+S +N++L+    N T  N  T   TD NG+APF+++T
Sbjct:  362 NVDHHYRRGIPYFGQIKLVDKDNSPISNKVIQLFVNNKN-THNFT--TDINGIAPFSIDT 418
```

Fig 3A

BLASTX ALIGNMENT OF SEQ ID NO: 29 ALPHA-2-MACROGLOBULIN-LIKE POLYPEPTIDE WITH
OVOS_CHICK OVOSTATIN PRECURSOR SEQ ID NO: 41

```
Query: 1344 SGWNGTDVSLEGKFQMEDLVYNPEQVPRYYQNAVLHLRPFYSTTRSFLGIHRLNGPLKCG 1523
            S    ++SL+ ++ D  ++  +   Y +A L ++  YS T SF+ I  L   + CG
Sbjct:  419 SKIFDPELSLKALYKTSDQCHSEGWIEPSYPDASLSVQRLYSWTSSFVRIEPLWKDMSCG  478

Query: 1524 QPQEVLVDYYIDPADASPTQEISFSYYLIGKGSLVMEGQKILNSKKKGLKASFSLSLTFT 1703
            Q + +  V Y  ++       ++F Y  + KG +V+ G+    +N +         +F + L
Sbjct:  479 QKRMITVYYILNTEGYEHINIVNFYVVGMAKGKIVLTGEIKVNIQADQ-NGTFMIPLVVN  537

Query: 1704 SRLAPDPSLVIYAIFPSGGVVADKIQFSVEMCFDNQVSIGFSPSQQLPGAEVELQLQAAP 1883
            ++AP   L++Y + P+  +VAD   ++FS+E CF N+V L FS  Q L  + V L  ++AA
Sbjct:  538 EKMAPALRLLVYMLHPAKELVADSVRFSIEKCFKNKVQLQFSEKQMLTTSNVSLVIEAAA  597

Query: 1884 CSLCALRAVDESVLLLRPDRELSNRSVYGMFPFWYGHYPYQVAEYDQCPVSGPMDFPQPL 2063
            S  CA+RAVD+S+LLL++ + ELS  ++Y + P          Q     +   D PQ
Sbjct:  598 NSFCAVRAVDKSMILLKSETELSAETIYNLHPI----QDLQGYIFNGLNLE---DDPQ---  648

Query: 2064 IDPMPQGHSS-QRSIIWRPSFSE-GTDLFSFFRDVGLKILSNAKIKKPVTCSH---RSPE 2228
            DP    +   +RP  S  G D++ F  RD+G+K  +N+KI++P C+         R P
Sbjct:  649 -DPCVSSDDIFHKGLYYRPLTSGLGPDVYQFLRDMGMKFFTNSKIRQPTVCTRETVRPPS  707

Query: 2229 YSTAMG--AGGGHPE------AFESSTPLHQAEDSQVRQYFPETWLWDLFPIGNSGKEAVH 2387
            Y    G   A  H +       AE    H E    +R++FPFTW+WD+ I  ++GK +V
Sbjct:  708 YFLNAGFTASTHHVKLSAEVAREERGKRHILET--IREFFPETWIWDIILINSTGKASVS  765

Query: 2388 VTVPDAITEWKAMSFCTSQSRGFGLSPTVGLTAFKPFFVDLTLPYSVVRGESFRLTATIF 2567
            T+PD ITEWKA +FC   +   GFG+S    LTAF+ PFFVDLTLPYS++  GE F + A +F
Sbjct:  766 YTIPDTITEWKASAFCVEELAGFGMSVPATLTAFQPFFVDLTLPYSIHGEDFLVRANVF  825

Query: 2568 NYLKDCIRV 2594
            NYL  CI++
Sbjct:  826 NYLNHCIKI  834
```

Fig 3B

BLASTX ALIGNMENT OF SEQ ID NO: 29 ALPHA-2-MACROGLOBULIN-LIKE POLYPEPTIDE WITH
RECOMBINANT HUMAN ALPHA-2-MACROGLOBULIN SEQ ID NO: 24

Query: Alpha-2-macroglobulin polypeptide (SEQ ID NO: 29)
Subject: sp|R11334|R11334 Recombinant human alpha-2 macroglobulin. SEQ ID NO: 24
Length = 1474

Score = 1289 (458.8 bits), Expect = 5.6e-134, Sum P(2) = 5.6e-134
Identities = 300/834 (35%), Positives = 448/834 (53%), Frame = +3

```
Query:   141 LLLGMLALSPAIAEELPNYLVTLPARLNPSVQKVCLDLSPGYSDVKFTVTLETKDKTQK   320
             LLL +L   + A    P Y+V +P+ L+    +K C+ LS     V  + +LE+
Sbjct:    13 LLLLVLVPTDASVSGKPQYMVIVPSLLHTETTEKGCVLLSYLNETVTVSASLESVRGNRS    72

Query:   321 LLEYSGLKKRHLHCISFLVPPPAGGTEEVATIRVSGVGNNISFEEKKKVLIQRQGNGTFV   500
             L    + + LHC++F VP +   EEV   G  F+++ V+++ +  FV
Sbjct:    73 LFTDLEAENDVLHCVAFAVPK--SSSNEEVMFLTVQVKGPTQEFKKRTTVMVKNEDSLVFV   131

Query:   501 QTDKPLYTPGQQVTFRIVTMDSNFVPVADKYSMVELQDPNSNRIAQWLEVVPEQGIVDLS   680
             QTDK +Y PGQ V    FR+V+MD  NF  P+N+     +V +QDP NRIAQW    R G+    S
Sbjct:   132 QTDKSIYKPGQTVKFRVVSMDENFHPLNELIPLVYIQDPKGNRIAQWQSFQLEGGLKQFS   191

Query:   681 FQLAPEAMLGTYTVAVAE---GKTFGTFSVEEVLPKFKVEVEPKELSTVQESFLVKIC    851
             F L+ E    G+Y V V    G+T   G+T  F+VEE+V PKF++V+V  PK ++ ++E    V +C
Sbjct:   192 FPLSSEPFQGSYKVVVQKKSGGRTEHPFTVEEFVLPKFEVQVTVPKITTLEREMNVSVC   251

Query:   852 CRYTYGKPMLGAVQVSVCQKANTYWYREVEREQLPDKCRNLSGQTDKTGCFSAPVDMATF  1031
                   +      +         E  C  SGQ +    GCF  V    F
Sbjct:   252 GLYTYGKPVFGHVTVSICRKYSDA--SDCHGEDSQAFCEKPSGQLNSHGCFYQQVKTKVF   309

Query:  1032 DLIGYAYSHQINIVATVVEEGTGVEANATQNIYISPQMGSMTFEDTSNFYHIPNFPFSGKI  1211
             L    Y +++  A + EEGT VE       Q+  I+ +    ++F     ++F PF G++
Sbjct:   310 QLKRKEYEMKLHTEAQIQEEGTVVELTGRQSSEITRTITKLSFVKVDSHFRQGIPFFGQV   369

Query:  1212 RVRGHDDSFLKNHLVFLVIYGTNGTFNQTLVTDNNGLAPFTLETSGWNGTDVSLEGKFQM  1391
             R+     + N ++F  I G        TD +GL F++ T+   GT +++
Sbjct:   370 RLVDGKGVPIPNKVIF--IRGNEANYYSNATTDEHGLVQFSINTTNVMGTSLTVRVNYKD   427

Query:  1392 EDLVYNPEQVPRYYQNAYLHLRPFYSTTRSFLGIHRLNGPLKCGQPQEVLVDYYIDPADA  1571
             Y +V  ++ A+      -S  ++SF+ +  ++ L CG  Q  V  ++
Sbjct:   428 RSPCYGYQWVSEHEEAHHTAYLVFSPSKSFVHLEPMSHELPCGHTQTVQAHYILNGGTL   487
```

Fig. 4A

BLASTX ALIGNMENT OF SEQ ID NO: 29 ALPHA-2-MACROGLOBULIN-LIKE POLYPEPTIDE WITH
RECOMBINANT HUMAN ALPHA-2-MACROGLOBULIN SEQ ID NO: 24

```
Query: 1572 SPDQEISFSYYLIGKGSLVMEGQKHLNSKKKGLKASFSI.SLTFTSRLAPDPSLVIYAIFP 1751
            +++SF Y ++ KG +V G  L K++ +K  FS+S+    S +AP  L+IYA+ P
Sbjct:  488 LGLKKLSFYYLIMAKGGTVRTGTHGLLVKQEDMKGHFSISIPVKSDIAPVARLLIYAVLP  547

Query: 1752 SGGVVADKIQFSVEMCFDNQVSLGFSPSQQLPGAEVELQLQAAPGSLCALRAVDESVLLL 1931
            +G V+ D  ++ VE C  N+V L FSPSQ LP +  L++ AAP S+CALRAVD+SVLL+
Sbjct:  548 TGDVIGDSAKYDVENCLANKVDLSFSPSQSLPASHAHLRVTAAPQSVCALRAVDQSVLLM  607

Query: 1932 RPDRELSNRSVYGMFPFWYGHYPYQVAEYDQCPVSGPWDFPQPLIDPMPQGHSSQRSIIW 2111
            +PD ELS  SVY + P       E D       GP + Q    D +++     I +
Sbjct:  608 KPDAELSASSVYNLLP-------------EKDLTGFPGPLN-DQDDEDCINRIINVYINGITY  655

Query: 2112 RP-SFSEGTDLPSFFRDVGLKILSNAKIKKPVDCSH------RSPE------YSTAMGAG 2252
            P S +   D++SF  D+GLK  +N+KI+KP  C         PE      Y + + G
Sbjct:  656 TFVSSTNEKDMYSFLEDMGLKAFTNSKIRKPKMCPQLQQYEMHGPEGLRVGFYESDV-MG  714

Query: 2253 GGHPEAFESSTPLHQAEDSQVRQYFPETWLWDLFPIGNSGKEAVHVTVPDAITEWKAMSF 2432
            GH        P H      +R+YF  ETW+WDL  + +++G   V VTVPD ITEWKA +F
Sbjct:  715 RGHARLVHVEEP-HT---ETVRKYFAETWIWDLVVVNSAGVAEVGVTVPDTITEWKAGAF  770

Query: 2433 CTSQSRGFGLSPTVGLTAFKPFFVDLTLPFYSVVRGESFRLTATIFNYLKDCIRV 2594
            C S+  G G+S T L   AF+PFFV +LT+PYSV+RGE+F L AT+ NYL  CIRV
Sbjct:  771 CLSEDAGLGISSTASLRAFQPFFVELTMPYSVIRGEAFTLKATVLNYLPKCIRV  824
```

Fig. 4B

SEQUENCE LISTING

<160> NUMBER OF SEQ ID NOS: 41

<210> SEQ ID NO 1
<211> LENGTH: 386
<212> TYPE: DNA
<213> ORGANISM: Homo sapiens

<400> SEQUENCE: 1

```
tggatagcaa cttcgctcca gggaatgaca agcactccat gggggaacta caggatccaa      60
atagcaacag gattgcacag ggctggaagt ggtacctgag caaggcattg tatacctgtc     120
cttccaactg gcaccagagg caatgctgga cacctacatg tggcagtggc tgagggcaag     180
acctttggta ctttcagtgt ggaggaatat gtgctgccga agtttaagga ggatttcgtc     240
cacaatccgg gggtcgggag taggaattat tttttgcttt gaggagaaca aaaaggttct     300
aattcagagg gggaacggca cctttgtaca gactgacaaa cctctctaca ccccagggca     360
gcaagtgtat ttccgcattg tcacca                                          386
```

<210> SEQ ID NO 2
<211> LENGTH: 1359
<212> TYPE: DNA
<213> ORGANISM: Homo sapiens

<400> SEQUENCE: 2

```
tggacaattc ggcacgagct agcaacttct ggactgaaga agaggcactt acattggatc      60
tcctttcttg taccacctcc tgctggtggc acagaagaag tggccacaat ccgggtgtcg     120
ggagttgtga aataacatca gctttgagga aaggaaaaag gttctaattc agaggcaggg     180
gaacggcacc tttgtacaga ctgacaaacc tctctacacc ccagggcagc aagtgtattt     240
ccgcattgtc accatggata gcaacttcgt tccagtgaat gacaagtact ccatggtgga     300
actacaggat ccaaatagca acaggattgc acagtggctg gaagtggtac ctgagcaagg     360
cattgtagac ctgtccttcc aactggcacc agaggcaatg ctgggcacct acactgtggc     420
agtggctgag ggcaagacct tggtactttt cagtgtggag gaatatgtgc tgccgaagtt     480
taaggtggaa gtggtggaac ccaaggagtt atcaacggtg caggaatctt tcttagtaaa     540
aatttgttgt aggtacacct atggaaagcc catgctaggg gcagtgcagg tatctgtgtg     600
tcagaagggc aaatacttac tggtatcgag aggtgggaac gggaaccagc ttcctggacc     660
aatgcaggaa cctctctgga cagactgaca aaacaggatg tttctcagca cctgtggaca     720
tggccacctt tgacctcatt ggatatgcgt acagccatca aatcaatatt gtggctactg     780
ttgtggagga agggacaggt gtggaggcca atgccactca gaatatctac atttctccac     840
aaatgggatt aaatgacctt tggaagacac cagcaatttt taccatccaa attttcccct     900
tcagtgggga agataaggaa ttaggggcca atgatgacct cttcctcaag aaccatctag     960
tgtttctggt gatttatggc acaaatggaa ccttcaacca gaccctggtt actgataaca    1020
atggcctagc tccctttacc tttggagaaa tccccggtgg aaagggacag aacgttctct    1080
ggagggaaag ttttcaatag gaaaacttat tatataatcc ggaacaaagg gccaccgtta    1140
ctaccaaaaa ggcctaacct gggcctgcga acccttttac aagaacaaac ccggaacttt    1200
cctttggcat tcccccggct taaacggccc cttgaaatgt ggccagcccc aggaagtgct    1260
ggtggaatta ttcacattcga cccgggccat gcaagcccct gacccaagag atcaaccttc    1320
ttctactatt ttaaataggg aaaggaagtt tggtgaatg                           1359
```

<210> SEQ ID NO 3
<211> LENGTH: 4527
<212> TYPE: DNA
<213> ORGANISM: Homo sapiens
<220> FEATURE:
<221> NAME/KEY: CDS
<222> LOCATION: (1)..(4527)

<400> SEQUENCE: 3

```
atg tgg gct cag ctc ctt cta gga atg ttg gcc cta tca cca gcc att       48
Met Trp Ala Gln Leu Leu Leu Gly Met Leu Ala Leu Ser Pro Ala Ile
1               5                   10                  15 gca gaa gaa ctt cca aac tac ctg gtg aca tta cca gcc cgg cta aat       96
Ala Glu Glu Leu Pro Asn Tyr Leu Val Thr Leu Pro Ala Arg Leu Asn
            20                  25                  30 ttc ccc tcc gtt cag aag gtt tgt ttg gac ctg agc cct ggg tac agt      144
Phe Pro Ser Val Gln Lys Val Cys Leu Asp Leu Ser Pro Gly Tyr Ser
        35                  40                  45 gat gtt aaa ttc acg gtt act ctg gag acc aag gac aag acc cag aag      192
Asp Val Lys Phe Thr Val Thr Leu Glu Thr Lys Asp Lys Thr Gln Lys
    50                  55                  60 ttg cta gaa tac tct gga ctg aag aag agg cac tta cat tgt atc tcc      240
Leu Leu Glu Tyr Ser Gly Leu Lys Lys Arg His Leu His Cys Ile Ser
65                  70                  75                  80 ttt ctt gta cca cct cct gct ggt ggc aca gaa gaa gtg gcc aca atc      288
```

```
Phe Leu Val Pro Pro Ala Gly Gly Thr Glu Glu Val Ala Thr Ile
             85                  90                  95 cgg gtg tcg gga gtt gga aat aac atc agc ttt gag gag aag aaa aag      336
Arg Val Ser Gly Val Gly Asn Asn Ile Ser Phe Glu Glu Lys Lys Lys
            100                 105                 110 gtt cta att cag agg cag ggg aac ggc acc ttt gta cag act gac aaa      384
Val Leu Ile Gln Arg Gln Gly Asn Gly Thr Phe Val Gln Thr Asp Lys
            115                 120                 125 cct ctc tac acc cca ggg cag caa gtg tat ttc cgc att gtc acc atg      432
Pro Leu Tyr Thr Pro Gly Gln Gln Val Tyr Phe Arg Ile Val Thr Met
    130                 135                 140 gat agc aac ttc gtt cca gtg aat gac aag tac tcc atg gtg gaa cta      480
Asp Ser Asn Phe Val Pro Val Asn Asp Lys Tyr Ser Met Val Glu Leu
145                 150                 155                 160 cag gat cca aat agc aac agg att gca cag tgg ctg gaa gtg gta cct      528
Gln Asp Pro Asn Ser Asn Arg Ile Ala Gln Trp Leu Glu Val Val Pro
                165                 170                 175 gag caa ggc att gta gac ctg tcc ttc caa ctg gca cca gag gca atg      576
Glu Gln Gly Ile Val Asp Leu Ser Phe Gln Leu Ala Pro Glu Ala Met
            180                 185                 190 ctg ggc acc tac act gtg gca gtg gct gag ggc aag acc ttt ggt act      624
Leu Gly Thr Tyr Thr Val Ala Val Ala Glu Gly Lys Thr Phe Gly Thr
        195                 200                 205 ttc agt gtg gag gaa tat gtg ctg ccg aag ttt aag gtg gaa gtg gtg      672
Phe Ser Val Glu Glu Tyr Val Leu Pro Lys Phe Lys Val Glu Val Val
    210                 215                 220 gaa ccc aag gag tta tca acg gtg cag gaa tct ttc tta gta aaa att      720
Glu Pro Lys Glu Leu Ser Thr Val Gln Glu Ser Phe Leu Val Lys Ile
225                 230                 235                 240 tgt tgt agg tac acc tat gga aag ccc atg cta ggg gca gtg cag gta      768
Cys Cys Arg Tyr Thr Tyr Gly Lys Pro Met Leu Gly Ala Val Gln Val
                245                 250                 255 tct gtg tgt cag aag gca aat act tac tgg tat cga gag gtg gaa cgg      816
Ser Val Cys Gln Lys Ala Asn Thr Tyr Trp Tyr Arg Glu Val Glu Arg
            260                 265                 270 gaa cag ctt cct gac aaa tgc agg aac ctc tct gga cag act gac aaa      864
Glu Gln Leu Pro Asp Lys Cys Arg Asn Leu Ser Gly Gln Thr Asp Lys
        275                 280                 285 aca gga tgt ttc tca gca cct gtg gac atg gcc acc ttt gac ctc att      912
Thr Gly Cys Phe Ser Ala Pro Val Asp Met Ala Thr Phe Asp Leu Ile
    290                 295                 300 gga tat gcg tac agc cat caa atc aat att gtg gct act gtt gtg gag      960
Gly Tyr Ala Tyr Ser His Gln Ile Asn Ile Val Ala Thr Val Val Glu
305                 310                 315                 320 gaa ggg aca ggt gtg gag gcc aat gcc act cag aat atc tac att tct     1008
Glu Gly Thr Gly Val Glu Ala Asn Ala Thr Gln Asn Ile Tyr Ile Ser
                325                 330                 335 cca caa atg gga tca atg acc ttt gaa gac acc agc aat ttt tac cat     1056
Pro Gln Met Gly Ser Met Thr Phe Glu Asp Thr Ser Asn Phe Tyr His
            340                 345                 350 cca aat ttc ccc ttc agt ggg aag ata aga gtt agg ggc cat gat gac     1104
Pro Asn Phe Pro Phe Ser Gly Lys Ile Arg Val Arg Gly His Asp Asp
        355                 360                 365 tcc ttc ctc aag aac cat cta gtg ttt ctg gtg att tat ggc aca aat     1152
Ser Phe Leu Lys Asn His Leu Val Phe Leu Val Ile Tyr Gly Thr Asn
    370                 375                 380 gga acc ttc aac cag acc ctg gtt act gat aac aat ggc cta gct ccc     1200
Gly Thr Phe Asn Gln Thr Leu Val Thr Asp Asn Asn Gly Leu Ala Pro
385                 390                 395                 400
```

```
ttt acc ttg gag aca tcc ggt tgg aat ggg aca gac gtt tct ctg gag    1248
Phe Thr Leu Glu Thr Ser Gly Trp Asn Gly Thr Asp Val Ser Leu Glu
            405                 410                 415 gga aag ttt caa atg gaa gac tta gta tat aat ccg gaa caa gtg cca    1296
Gly Lys Phe Gln Met Glu Asp Leu Val Tyr Asn Pro Glu Gln Val Pro
            420                 425                 430 cgt tac tac caa aat gcc tac ctg cac ctg cga ccc ttc tac agc aca    1344
Arg Tyr Tyr Gln Asn Ala Tyr Leu His Leu Arg Pro Phe Tyr Ser Thr
            435                 440                 445 acc cgc agc ttc ctt ggc atc cac cgg cta aac ggc ccc ttg aaa tgt    1392
Thr Arg Ser Phe Leu Gly Ile His Arg Leu Asn Gly Pro Leu Lys Cys
450                 455                 460 ggc cag ccc cag gaa gtg ctg gtg gat tat tac atc gac ccg gcc gat    1440
Gly Gln Pro Gln Glu Val Leu Val Asp Tyr Tyr Ile Asp Pro Ala Asp
465                 470                 475                 480 gca agc cct gac caa gag atc agc ttc tcc tac tat tta ata ggg aaa    1488
Ala Ser Pro Asp Gln Glu Ile Ser Phe Ser Tyr Tyr Leu Ile Gly Lys
            485                 490                 495 gga agt ttg gtg atg gag ggg cag aaa cac ctg aac tct aag aag aaa    1536
Gly Ser Leu Val Met Glu Gly Gln Lys His Leu Asn Ser Lys Lys Lys
            500                 505                 510 gga ctg aaa gcc tcc ttc tct ctc tca ctg acc ttc act tcg aga ctg    1584
Gly Leu Lys Ala Ser Phe Ser Leu Ser Leu Thr Phe Thr Ser Arg Leu
            515                 520                 525 gcc cct gat cct tcc ctg gtg atc tat gcc att ttt ccc agt gga ggt    1632
Ala Pro Asp Pro Ser Leu Val Ile Tyr Ala Ile Phe Pro Ser Gly Gly
            530                 535                 540 gtt gta gct gac aaa att cag ttc tca gtc ggg atg tgc ttt gac aat    1680
Val Val Ala Asp Lys Ile Gln Phe Ser Val Gly Met Cys Phe Asp Asn
545                 550                 555                 560 cag gtt tcc ctt ggc ttc tcc ccc tcc cag cag ctt cca gga gca gaa    1728
Gln Val Ser Leu Gly Phe Ser Pro Ser Gln Gln Leu Pro Gly Ala Glu
            565                 570                 575 gtg gag ctg cag ctg cag gca gct ccc gga tcc ctg tgt gcg ctc cgg    1776
Val Glu Leu Gln Leu Gln Ala Ala Pro Gly Ser Leu Cys Ala Leu Arg
            580                 585                 590 gcg gtg gat gag agt gtc tta ctg ctt agg cca gac aga gag ctg agc    1824
Ala Val Asp Glu Ser Val Leu Leu Arg Pro Asp Arg Glu Leu Ser
            595                 600                 605 aac cgc tct gtc tat ggg atg ttt cca ttc tgg tat ggt cac tac ccc    1872
Asn Arg Ser Val Tyr Gly Met Phe Pro Phe Trp Tyr Gly His Tyr Pro
            610                 615                 620 tat caa gtg gct gag tat gat cag tgt cca gtg tct ggc cca tgg gac    1920
Tyr Gln Val Ala Glu Tyr Asp Gln Cys Pro Val Ser Gly Pro Trp Asp
625                 630                 635                 640 ttt cct cag ccc ctc att gac cca atg ccc caa ggg cat tcg agc cag    1968
Phe Pro Gln Pro Leu Ile Asp Pro Met Pro Gln Gly His Ser Ser Gln
            645                 650                 655 cgt tcc att atc tgg agg ccc tcg ttc tct gaa ggc acg gac ctt ttc    2016
Arg Ser Ile Ile Trp Arg Pro Ser Phe Ser Glu Gly Thr Asp Leu Phe
            660                 665                 670 agc ttt ttc cgg gac gtg ggc ctg aaa ata ctg tcc aat gcc aaa atc    2064
Ser Phe Phe Arg Asp Val Gly Leu Lys Ile Leu Ser Asn Ala Lys Ile
            675                 680                 685 aag aag cca gta gat tgc agt cac aga tct cca gaa tac agc act gct    2112
Lys Lys Pro Val Asp Cys Ser His Arg Ser Pro Glu Tyr Ser Thr Ala
            690                 695                 700 atg ggt ggc ggt ggt cat cca gag gct ttt gag tca tca act cct tta    2160
Met Gly Gly Gly Gly His Pro Glu Ala Phe Glu Ser Ser Thr Pro Leu
705                 710                 715                 720
```

```
cat caa gca gag gat tct cag gtc cgc cag tac ttc cca gag acc tgg        2208
His Gln Ala Glu Asp Ser Gln Val Arg Gln Tyr Phe Pro Glu Thr Trp
            725                 730                 735 ctc tgg gat ctg ttt cct att ggt aac tcg ggg aag gag gcg gtc cac        2256
Leu Trp Asp Leu Phe Pro Ile Gly Asn Ser Gly Lys Glu Ala Val His
        740                 745                 750 gtc aca gtt cct gac gcc atc acc gag tgg aag gcg atg agt ttc tgc        2304
Val Thr Val Pro Asp Ala Ile Thr Glu Trp Lys Ala Met Ser Phe Cys
            755                 760                 765 act tcc cag tca aga ggc ttc ggg ctt tca ccc act gtt gga cta act        2352
Thr Ser Gln Ser Arg Gly Phe Gly Leu Ser Pro Thr Val Gly Leu Thr
770                 775                 780 gct ttc aag ccg ttc ttt gtt gac ctg act ctc cct tac tca gta gtc        2400
Ala Phe Lys Pro Phe Phe Val Asp Leu Thr Leu Pro Tyr Ser Val Val
785                 790                 795                 800 cgt ggg gaa tcc ttt cgt ctt act gcc acc atc ttc aat tac cta aag        2448
Arg Gly Glu Ser Phe Arg Leu Thr Ala Thr Ile Phe Asn Tyr Leu Lys
                805                 810                 815 gat tgc atc agg gtt cag act gac ctg gct aaa tcg cat gag tac cag        2496
Asp Cys Ile Arg Val Gln Thr Asp Leu Ala Lys Ser His Glu Tyr Gln
            820                 825                 830 cta gaa tca tgg gca gat tct cag acc tcc agt tgt ctc tgt gct gat        2544
Leu Glu Ser Trp Ala Asp Ser Gln Thr Ser Ser Cys Leu Cys Ala Asp
        835                 840                 845 gac gca aaa acc cac cac tgg aac atc aca gct gtc aaa ttg ggt cac        2592
Asp Ala Lys Thr His His Trp Asn Ile Thr Ala Val Lys Leu Gly His
850                 855                 860 att aac ttt act att agt aca aag att ctg gac agc aat gaa cca tgt        2640
Ile Asn Phe Thr Ile Ser Thr Lys Ile Leu Asp Ser Asn Glu Pro Cys
865                 870                 875                 880 ggg ggc cag aag ggg ttt gtt ccc caa aag ggc cga agt gac acg ctc        2688
Gly Gly Gln Lys Gly Phe Val Pro Gln Lys Gly Arg Ser Asp Thr Leu
                885                 890                 895 atc aag cca gtt ctc gtc aaa cct gag gga gtc ctg gtg gag aag aca        2736
Ile Lys Pro Val Leu Val Lys Pro Glu Gly Val Leu Val Glu Lys Thr
            900                 905                 910 cac agc tca ttg ctg tgc cca aaa gga aag gtg gca tct gaa tct gtc        2784
His Ser Ser Leu Leu Cys Pro Lys Gly Lys Val Ala Ser Glu Ser Val
        915                 920                 925 tcc ctg gag ctc cca gtg gac att gtt cct gac tcg acc aag gct tat        2832
Ser Leu Glu Leu Pro Val Asp Ile Val Pro Asp Ser Thr Lys Ala Tyr
930                 935                 940 gtt acg gtt ctg ggt aag cag tta gag att ctt gac tca gaa agg aaa        2880
Val Thr Val Leu Gly Lys Gln Leu Glu Ile Leu Asp Ser Glu Arg Lys
945                 950                 955                 960 agg cga atg gag gct gca aag gtg tgg aga gac att atg ggc aca gcc        2928
Arg Arg Met Glu Ala Ala Lys Val Trp Arg Asp Ile Met Gly Thr Ala
                965                 970                 975 ctg cag aac ctg gat ggt ctg gtg cag atg ccc agt ggc tgt ggc gag        2976
Leu Gln Asn Leu Asp Gly Leu Val Gln Met Pro Ser Gly Cys Gly Glu
            980                 985                 990 cag aac atg gtc ttg ttt gct ccc atc atc tat gtc ttg cag tac ctg        3024
Gln Asn Met Val Leu Phe Ala Pro Ile Ile Tyr Val Leu Gln Tyr Leu
        995                 1000                1005 gag aag gca ggg ctg ctg acg gag gag atc agg tct cgg gca gtg        3069
Glu Lys Ala Gly Leu Leu Thr Glu Glu Ile Arg Ser Arg Ala Val
            1010                1015                1020 ggt ttc ctg gaa ata ggg tac cag aag gag ctg atg tac aaa cac        3114
Gly Phe Leu Glu Ile Gly Tyr Gln Lys Glu Leu Met Tyr Lys His
```

```
                                       -continued 1025                1030                1035
agc aat ggc tca tac agt gcc ttt ggg gag cga gat gga aat gga      3159
Ser Asn Gly Ser Tyr Ser Ala Phe Gly Glu Arg Asp Gly Asn Gly
    1040                1045                1050 aac aca tgg ctg aca gcg ttt gtc aca aaa tgc ttt ggc caa gct      3204
Asn Thr Trp Leu Thr Ala Phe Val Thr Lys Cys Phe Gly Gln Ala
    1055                1060                1065 cag aaa ttc atc ttc att gat ccc aag aac atc cag gat gct ctc      3249
Gln Lys Phe Ile Phe Ile Asp Pro Lys Asn Ile Gln Asp Ala Leu
    1070                1075                1080 aag tgg atg gca gga aac cag ctc ccc agt ggc tgc tat gcc aac      3294
Lys Trp Met Ala Gly Asn Gln Leu Pro Ser Gly Cys Tyr Ala Asn
    1085                1090                1095 gtg gga aat ctc ctt cac aca gct atg aag ggt ggt gtt gat gat      3339
Val Gly Asn Leu Leu His Thr Ala Met Lys Gly Gly Val Asp Asp
    1100                1105                1110 gag gtc tcc ttg act gcg tat gtc aca gct gca ttg ctg gag atg      3384
Glu Val Ser Leu Thr Ala Tyr Val Thr Ala Ala Leu Leu Glu Met
    1115                1120                1125 gga aag gat gta gat gac cca atg gtg agt cag ggt cta cgg tgt      3429
Gly Lys Asp Val Asp Asp Pro Met Val Ser Gln Gly Leu Arg Cys
    1130                1135                1140 ctc aag aat tcg gcc acc tcc acg acc aac ctc tac aca cag gcc      3474
Leu Lys Asn Ser Ala Thr Ser Thr Thr Asn Leu Tyr Thr Gln Ala
    1145                1150                1155 ctg ttg gct tac att ttc tcc ctg gct ggg gaa atg gac atc aga      3519
Leu Leu Ala Tyr Ile Phe Ser Leu Ala Gly Glu Met Asp Ile Arg
    1160                1165                1170 aac att ctc ctt aaa cag tta gat caa cag gct atc atc tca gga      3564
Asn Ile Leu Leu Lys Gln Leu Asp Gln Gln Ala Ile Ile Ser Gly
    1175                1180                1185 gaa tcc att tac tgg agc cag aaa cct act cca tca tcg aac gcc      3609
Glu Ser Ile Tyr Trp Ser Gln Lys Pro Thr Pro Ser Ser Asn Ala
    1190                1195                1200 agc cct tgg tct gag cct gcg gct gta gat gtg gaa ctc aca gca      3654
Ser Pro Trp Ser Glu Pro Ala Ala Val Asp Val Glu Leu Thr Ala
    1205                1210                1215 tat gca ttg ttg gcc cag ctt acc aag ccc agc ctg act caa aag      3699
Tyr Ala Leu Leu Ala Gln Leu Thr Lys Pro Ser Leu Thr Gln Lys
    1220                1225                1230 gag ata gcg aag gcc act agc ata gtg gct tgg ttg gcc aag caa      3744
Glu Ile Ala Lys Ala Thr Ser Ile Val Ala Trp Leu Ala Lys Gln
    1235                1240                1245 cac aat gca tat ggg ggc ttc tct tct act cag gat act gta gtt      3789
His Asn Ala Tyr Gly Gly Phe Ser Ser Thr Gln Asp Thr Val Val
    1250                1255                1260 gct ctc caa gct ctt gcc aaa tat gcc act acc gcc tac atg cca      3834
Ala Leu Gln Ala Leu Ala Lys Tyr Ala Thr Thr Ala Tyr Met Pro
    1265                1270                1275 tct gag gag atc aac ctg gtt gta aaa tcc act gag aat ttc cag      3879
Ser Glu Glu Ile Asn Leu Val Val Lys Ser Thr Glu Asn Phe Gln
    1280                1285                1290 cgc aca ttc aac ata cag tca gtt aac aga ttg gta ttt cag cag      3924
Arg Thr Phe Asn Ile Gln Ser Val Asn Arg Leu Val Phe Gln Gln
    1295                1300                1305 gat acc ctg ccc aat gtc cct gga atg tac acg ttg gag gcc tca      3969
Asp Thr Leu Pro Asn Val Pro Gly Met Tyr Thr Leu Glu Ala Ser
    1310                1315                1320 ggc cag ggc tgt gtc tat gtg cag acg gtg ttg aga tac aat att      4014
```

```
Gly Gln Gly Cys Val Tyr Val Gln Thr Val Leu Arg Tyr Asn Ile
    1325              1330                1335 ctc cct ccc aca aat atg aag acc ttt agt ctt agt gtg gaa ata      4059
Leu Pro Pro Thr Asn Met Lys Thr Phe Ser Leu Ser Val Glu Ile
    1340              1345                1350 gga aaa gct aga tgt gag caa ccg act tca cct cga tcc ttg act      4104
Gly Lys Ala Arg Cys Glu Gln Pro Thr Ser Pro Arg Ser Leu Thr
    1355              1360                1365 ctc act att cac acc agt tat gtg ggg agc cgt agc tct tcc aat      4149
Leu Thr Ile His Thr Ser Tyr Val Gly Ser Arg Ser Ser Ser Asn
    1370              1375                1380 atg gct att gtg gaa gtg aag atg cta tct ggg ttc agt ccc atg      4194
Met Ala Ile Val Glu Val Lys Met Leu Ser Gly Phe Ser Pro Met
    1385              1390                1395 gag ggc acc aat cag tta ctt ctc cag caa ccc ctg gtg aag aag      4239
Glu Gly Thr Asn Gln Leu Leu Leu Gln Gln Pro Leu Val Lys Lys
    1400              1405                1410 gtt gaa ttt gga act gac aca ctt aac att tac ttg gat gag ctc      4284
Val Glu Phe Gly Thr Asp Thr Leu Asn Ile Tyr Leu Asp Glu Leu
    1415              1420                1425 att aag aac act cag act tac acc ttc acc atc agc caa agt gtg      4329
Ile Lys Asn Thr Gln Thr Tyr Thr Phe Thr Ile Ser Gln Ser Val
    1430              1435                1440 ctg gtc acc aac ttg aaa cca gca acc atc aag gtc tat gac tac      4374
Leu Val Thr Asn Leu Lys Pro Ala Thr Ile Lys Val Tyr Asp Tyr
    1445              1450                1455 tac cta cca ggt tct ttt aaa tta tct cag tac aca att gtg tgg      4419
Tyr Leu Pro Gly Ser Phe Lys Leu Ser Gln Tyr Thr Ile Val Trp
    1460              1465                1470 tcc atg aac aat gac agc ata gtg gac tct gtg gca cgg cac cca      4464
Ser Met Asn Asn Asp Ser Ile Val Asp Ser Val Ala Arg His Pro
    1475              1480                1485 gaa cca ccc cct ttc aag aca gaa gca ttt att cct tca ctt cct      4509
Glu Pro Pro Pro Phe Lys Thr Glu Ala Phe Ile Pro Ser Leu Pro
    1490              1495                1500 ggg agt gtt aac aac tga                                          4527
Gly Ser Val Asn Asn
    1505

<210> SEQ ID NO 4
<211> LENGTH: 1508
<212> TYPE: PRT
<213> ORGANISM: Homo sapiens

<400> SEQUENCE: 4

Met Trp Ala Gln Leu Leu Leu Gly Met Leu Ala Leu Ser Pro Ala Ile
1               5                   10                  15

Ala Glu Glu Leu Pro Asn Tyr Leu Val Thr Leu Pro Ala Arg Leu Asn
                20                  25                  30

Phe Pro Ser Val Gln Lys Val Cys Leu Asp Leu Ser Pro Gly Tyr Ser
            35                  40                  45

Asp Val Lys Phe Thr Val Thr Leu Glu Thr Lys Asp Lys Thr Gln Lys
        50                  55                  60

Leu Leu Glu Tyr Ser Gly Leu Lys Lys Arg His Leu His Cys Ile Ser
65                  70                  75                  80

Phe Leu Val Pro Pro Pro Ala Gly Gly Thr Glu Glu Val Ala Thr Ile
                85                  90                  95

Arg Val Ser Gly Val Gly Asn Asn Ile Ser Phe Glu Glu Lys Lys Lys
            100                 105                 110
```

-continued

```
Val Leu Ile Gln Arg Gln Gly Asn Gly Thr Phe Val Gln Thr Asp Lys
        115                 120                 125

Pro Leu Tyr Thr Pro Gly Gln Gln Val Tyr Phe Arg Ile Val Thr Met
        130                 135                 140

Asp Ser Asn Phe Val Pro Val Asn Asp Lys Tyr Ser Met Val Glu Leu
145                 150                 155                 160

Gln Asp Pro Asn Ser Asn Arg Ile Ala Gln Trp Leu Glu Val Val Pro
                165                 170                 175

Glu Gln Gly Ile Val Asp Leu Ser Phe Gln Leu Ala Pro Glu Ala Met
            180                 185                 190

Leu Gly Thr Tyr Thr Val Ala Val Ala Glu Gly Lys Thr Phe Gly Thr
        195                 200                 205

Phe Ser Val Glu Glu Tyr Val Leu Pro Lys Phe Lys Val Glu Val Val
        210                 215                 220

Glu Pro Lys Glu Leu Ser Thr Val Gln Glu Ser Phe Leu Val Lys Ile
225                 230                 235                 240

Cys Cys Arg Tyr Thr Tyr Gly Lys Pro Met Leu Gly Ala Val Gln Val
                245                 250                 255

Ser Val Cys Gln Lys Ala Asn Thr Tyr Trp Tyr Arg Glu Val Glu Arg
            260                 265                 270

Glu Gln Leu Pro Asp Lys Cys Arg Asn Leu Ser Gly Gln Thr Asp Lys
        275                 280                 285

Thr Gly Cys Phe Ser Ala Pro Val Asp Met Ala Thr Phe Asp Leu Ile
        290                 295                 300

Gly Tyr Ala Tyr Ser His Gln Ile Asn Ile Val Ala Thr Val Val Glu
305                 310                 315                 320

Glu Gly Thr Gly Val Glu Ala Asn Ala Thr Gln Asn Ile Tyr Ile Ser
                325                 330                 335

Pro Gln Met Gly Ser Met Thr Phe Glu Asp Thr Ser Asn Phe Tyr His
            340                 345                 350

Pro Asn Phe Pro Phe Ser Gly Lys Ile Arg Val Arg Gly His Asp Asp
        355                 360                 365

Ser Phe Leu Lys Asn His Leu Val Phe Leu Val Ile Tyr Gly Thr Asn
        370                 375                 380

Gly Thr Phe Asn Gln Thr Leu Val Thr Asp Asn Asn Gly Leu Ala Pro
385                 390                 395                 400

Phe Thr Leu Glu Thr Ser Gly Trp Asn Gly Thr Asp Val Ser Leu Glu
                405                 410                 415

Gly Lys Phe Gln Met Glu Asp Leu Val Tyr Asn Pro Glu Gln Val Pro
            420                 425                 430

Arg Tyr Tyr Gln Asn Ala Tyr Leu His Leu Arg Pro Phe Tyr Ser Thr
        435                 440                 445

Thr Arg Ser Phe Leu Gly Ile His Arg Leu Asn Gly Pro Leu Lys Cys
        450                 455                 460

Gly Gln Pro Gln Glu Val Leu Val Asp Tyr Tyr Ile Asp Pro Ala Asp
465                 470                 475                 480

Ala Ser Pro Asp Gln Glu Ile Ser Phe Ser Tyr Tyr Leu Ile Gly Lys
                485                 490                 495

Gly Ser Leu Val Met Glu Gly Gln Lys His Leu Asn Ser Lys Lys Lys
            500                 505                 510

Gly Leu Lys Ala Ser Phe Ser Leu Ser Leu Thr Phe Thr Ser Arg Leu
        515                 520                 525
```

-continued

```
Ala Pro Asp Pro Ser Leu Val Ile Tyr Ala Ile Phe Pro Ser Gly Gly
        530                 535                 540

Val Val Ala Asp Lys Ile Gln Phe Ser Val Gly Met Cys Phe Asp Asn
545                 550                 555                 560

Gln Val Ser Leu Gly Phe Ser Pro Ser Gln Gln Leu Pro Gly Ala Glu
                565                 570                 575

Val Glu Leu Gln Leu Gln Ala Ala Pro Gly Ser Leu Cys Ala Leu Arg
        580                 585                 590

Ala Val Asp Glu Ser Val Leu Leu Arg Pro Asp Arg Glu Leu Ser
        595                 600                 605

Asn Arg Ser Val Tyr Gly Met Phe Pro Phe Trp Tyr Gly His Tyr Pro
610                 615                 620

Tyr Gln Val Ala Glu Tyr Asp Gln Cys Pro Val Ser Gly Pro Trp Asp
625                 630                 635                 640

Phe Pro Gln Pro Leu Ile Asp Pro Met Pro Gln Gly His Ser Ser Gln
                645                 650                 655

Arg Ser Ile Ile Trp Arg Pro Ser Phe Ser Glu Gly Thr Asp Leu Phe
                660                 665                 670

Ser Phe Phe Arg Asp Val Gly Leu Lys Ile Leu Ser Asn Ala Lys Ile
        675                 680                 685

Lys Lys Pro Val Asp Cys Ser His Arg Ser Pro Glu Tyr Ser Thr Ala
690                 695                 700

Met Gly Gly Gly Gly His Pro Glu Ala Phe Glu Ser Ser Thr Pro Leu
705                 710                 715                 720

His Gln Ala Glu Asp Ser Gln Val Arg Gln Tyr Phe Pro Glu Thr Trp
                725                 730                 735

Leu Trp Asp Leu Phe Pro Ile Gly Asn Ser Gly Lys Glu Ala Val His
                740                 745                 750

Val Thr Val Pro Asp Ala Ile Thr Glu Trp Lys Ala Met Ser Phe Cys
        755                 760                 765

Thr Ser Gln Ser Arg Gly Phe Gly Leu Ser Pro Thr Val Gly Leu Thr
770                 775                 780

Ala Phe Lys Pro Phe Val Asp Leu Thr Leu Pro Tyr Ser Val Val
785                 790                 795                 800

Arg Gly Glu Ser Phe Arg Leu Thr Ala Thr Ile Phe Asn Tyr Leu Lys
                805                 810                 815

Asp Cys Ile Arg Val Gln Thr Asp Leu Ala Lys Ser His Glu Tyr Gln
                820                 825                 830

Leu Glu Ser Trp Ala Asp Ser Gln Thr Ser Ser Cys Leu Cys Ala Asp
        835                 840                 845

Asp Ala Lys Thr His His Trp Asn Ile Thr Ala Val Lys Leu Gly His
850                 855                 860

Ile Asn Phe Thr Ile Ser Thr Lys Ile Leu Asp Ser Asn Glu Pro Cys
865                 870                 875                 880

Gly Gly Gln Lys Gly Phe Val Pro Gln Lys Gly Arg Ser Asp Thr Leu
                885                 890                 895

Ile Lys Pro Val Leu Val Lys Pro Glu Gly Val Leu Val Glu Lys Thr
                900                 905                 910

His Ser Ser Leu Leu Cys Pro Lys Gly Lys Val Ala Ser Glu Ser Val
        915                 920                 925

Ser Leu Glu Leu Pro Val Asp Ile Val Pro Asp Ser Thr Lys Ala Tyr
930                 935                 940

Val Thr Val Leu Gly Lys Gln Leu Glu Ile Leu Asp Ser Glu Arg Lys
```

-continued

```
           945                 950                 955                 960
Arg  Arg  Met  Glu  Ala  Ala  Lys  Val  Trp  Arg  Asp  Ile  Met  Gly  Thr  Ala
                     965                 970                 975
Leu  Gln  Asn  Leu  Asp  Gly  Leu  Val  Gln  Met  Pro  Ser  Gly  Cys  Gly  Glu
           980                 985                 990
Gln  Asn  Met  Val  Leu  Phe  Ala  Pro  Ile  Ile  Tyr  Val  Leu  Gln  Tyr  Leu
           995                1000                1005
Glu  Lys  Ala  Gly  Leu  Leu  Thr  Glu  Glu  Ile  Arg  Ser  Arg  Ala  Val
          1010                1015                1020
Gly  Phe  Leu  Glu  Ile  Gly  Tyr  Gln  Lys  Glu  Leu  Met  Tyr  Lys  His
          1025                1030                1035
Ser  Asn  Gly  Ser  Tyr  Ser  Ala  Phe  Gly  Glu  Arg  Asp  Gly  Asn  Gly
          1040                1045                1050
Asn  Thr  Trp  Leu  Thr  Ala  Phe  Val  Thr  Lys  Cys  Phe  Gly  Gln  Ala
          1055                1060                1065
Gln  Lys  Phe  Ile  Phe  Ile  Asp  Pro  Lys  Asn  Ile  Gln  Asp  Ala  Leu
          1070                1075                1080
Lys  Trp  Met  Ala  Gly  Asn  Gln  Leu  Pro  Ser  Gly  Cys  Tyr  Ala  Asn
          1085                1090                1095
Val  Gly  Asn  Leu  Leu  His  Thr  Ala  Met  Lys  Gly  Gly  Val  Asp  Asp
          1100                1105                1110
Glu  Val  Ser  Leu  Thr  Ala  Tyr  Val  Thr  Ala  Ala  Leu  Leu  Glu  Met
          1115                1120                1125
Gly  Lys  Asp  Val  Asp  Pro  Met  Val  Ser  Gln  Gly  Leu  Arg  Cys
          1130                1135                1140
Leu  Lys  Asn  Ser  Ala  Thr  Ser  Thr  Thr  Asn  Leu  Tyr  Thr  Gln  Ala
          1145                1150                1155
Leu  Leu  Ala  Tyr  Ile  Phe  Ser  Leu  Ala  Gly  Glu  Met  Asp  Ile  Arg
          1160                1165                1170
Asn  Ile  Leu  Leu  Lys  Gln  Leu  Asp  Gln  Gln  Ala  Ile  Ile  Ser  Gly
          1175                1180                1185
Glu  Ser  Ile  Tyr  Trp  Ser  Gln  Lys  Pro  Thr  Pro  Ser  Ser  Asn  Ala
          1190                1195                1200
Ser  Pro  Trp  Ser  Glu  Pro  Ala  Ala  Val  Asp  Val  Glu  Leu  Thr  Ala
          1205                1210                1215
Tyr  Ala  Leu  Leu  Ala  Gln  Leu  Thr  Lys  Pro  Ser  Leu  Thr  Gln  Lys
          1220                1225                1230
Glu  Ile  Ala  Lys  Ala  Thr  Ser  Ile  Val  Ala  Trp  Leu  Ala  Lys  Gln
          1235                1240                1245
His  Asn  Ala  Tyr  Gly  Gly  Phe  Ser  Ser  Thr  Gln  Asp  Thr  Val  Val
          1250                1255                1260
Ala  Leu  Gln  Ala  Leu  Ala  Lys  Tyr  Ala  Thr  Thr  Ala  Tyr  Met  Pro
          1265                1270                1275
Ser  Glu  Glu  Ile  Asn  Leu  Val  Val  Lys  Ser  Thr  Glu  Asn  Phe  Gln
          1280                1285                1290
Arg  Thr  Phe  Asn  Ile  Gln  Ser  Val  Asn  Arg  Leu  Val  Phe  Gln  Gln
          1295                1300                1305
Asp  Thr  Leu  Pro  Asn  Val  Pro  Gly  Met  Tyr  Thr  Leu  Glu  Ala  Ser
          1310                1315                1320
Gly  Gln  Gly  Cys  Val  Tyr  Val  Gln  Thr  Val  Leu  Arg  Tyr  Asn  Ile
          1325                1330                1335
Leu  Pro  Pro  Thr  Asn  Met  Lys  Thr  Phe  Ser  Leu  Ser  Val  Glu  Ile
          1340                1345                1350
```

-continued

| Gly | Lys<br>1355 | Ala | Arg | Cys | Glu<br>1360 | Gln | Pro | Thr | Ser | Pro<br>1365 | Arg | Ser | Leu | Thr |

Leu Thr Ile His Thr Ser Tyr Val Gly Ser Arg Ser Ser Ser Asn
    1370            1375            1380

Met Ala Ile Val Glu Val Lys Met Leu Ser Gly Phe Ser Pro Met
    1385            1390            1395

Glu Gly Thr Asn Gln Leu Leu Leu Gln Gln Pro Leu Val Lys Lys
    1400            1405            1410

Val Glu Phe Gly Thr Asp Thr Leu Asn Ile Tyr Leu Asp Glu Leu
    1415            1420            1425

Ile Lys Asn Thr Gln Thr Tyr Thr Phe Thr Ile Ser Gln Ser Val
    1430            1435            1440

Leu Val Thr Asn Leu Lys Pro Ala Thr Ile Lys Val Tyr Asp Tyr
    1445            1450            1455

Tyr Leu Pro Gly Ser Phe Lys Leu Ser Gln Tyr Thr Ile Val Trp
    1460            1465            1470

Ser Met Asn Asn Asp Ser Ile Val Asp Ser Val Ala Arg His Pro
    1475            1480            1485

Glu Pro Pro Pro Phe Lys Thr Glu Ala Phe Ile Pro Ser Leu Pro
    1490            1495            1500

Gly Ser Val Asn Asn
    1505

<210> SEQ ID NO 5
<211> LENGTH: 4527
<212> TYPE: DNA
<213> ORGANISM: Homo sapiens

<400> SEQUENCE: 5

```
atgtgggctc agctccttct aggaatgttg gccctatcac cagccattgc agaagaactt      60
ccaaactacc tggtgacatt accagcccgg ctaaatttcc cctccgttca gaaggtttgt     120
ttggacctga gccctgggta cagtgatgtt aaattcacgg ttactctgga gaccaaggac     180
aagacccaga agttgctaga atactctgga ctgaagaaga ggcacttaca ttgtatctcc     240
tttcttgtac cacctcctgc tggtggcaca gaagaagtgg ccacaatccg ggtgtcggga     300
gttggaaata acatcagctt tgaggagaag aaaaaggttc taattcagag caggggaac      360
ggcacctttg tacagactga caaacctctc tacaccccag ggcagcaagt gtatttccgc     420
attgtcacca tggatagcaa cttcgttcca gtgaatgaca gtactccat ggtggaacta      480
caggatccaa atagcaacag gattgcacag tggctggaag tggtacctga gcaaggcatt     540
gtagacctgt ccttccaact ggcaccagag gcaatgctgg gcacctacac tgtggcagtg     600
gctgagggca agacctttgg tactttcagt gtggaggaat atgtgctgcc gaagtttaag     660
gtggaagtgg tgaacccaa ggagttatca acggtgcagg aatctttctt agtaaaaatt      720
tgttgtaggt acacctatgg aaagcccatg ctaggggcag tgcaggtatc tgtgtgtcag     780
aaggcaaata cttactggta tcgagaggtg aacgggaac agcttcctga caaatgcagg     840
aacctctctg gacagactga caaacagga tgtttctcag cacctgtgga catggccacc     900
tttgacctca ttggatatgc gtacagccat caaatcaata ttgtggctac tgttgtggag     960
gaagggacag gtgtggaggc caatgccact cagaatatct acatttctcc acaaatggga    1020
tcaatgacct tgaagacac cagcaatttt taccatccaa atttcccctt cagtgggaag    1080
ataagagtta ggggccatga tgactccttc ctcaagaacc atctagtgtt tctggtgatt    1140
```

-continued

```
tatggcacaa atgaacctt caaccagacc ctggttactg ataacaatgg cctagctccc      1200
tttaccttgg agacatccgg ttggaatggg acagacgttt ctctggaggg aaagtttcaa      1260
atggaagact tagtatataa tccggaacaa gtgccacgtt actaccaaaa tgcctacctg      1320
cacctgcgac ccttctacag cacaacccgc agcttccttg gcatccaccg gctaaacggc      1380
cccttgaaat gtggccagcc ccaggaagtg ctggtggatt attacatcga cccgccgat       1440
gcaagccctg accaagagat cagcttctcc tactatttaa tagggaaagg aagtttggtg      1500
atggaggggc agaaacacct gaactctaag aagaaaggac tgaaagcctc cttctctctc      1560
tcactgacct tcacttcgag actggcccct gatccttccc tggtgatcta tgccatttt      1620
cccagtggag gtgttgtagc tgacaaaatt cagttctcag tcgggatgtg ctttgacaat      1680
caggtttccc ttggcttctc ccctcccag cagcttccag gagcagaagt ggagctgcag       1740
ctgcaggcag ctcccggatc cctgtgtgcg ctccggcgg tggatgagag tgtcttactg       1800
cttaggccag acagagagct gagcaaccgc tctgtctatg gatgtttcc attctggtat       1860
ggtcactacc cctatcaagt ggctgagtat gatcagtgtc cagtgtctgg cccatgggac      1920
tttcctcagc ccctcattga cccaatgccc caagggcatt cgagccagcg ttccattatc      1980
tggaggccct cgttctctga aggcacggac cttttcagct ttttccggga cgtgggcctg      2040
aaaatactgt ccaatgccaa atcaagaag ccagtagatt gcagtcacag atctccagaa       2100
tacagcactg ctatggggtgg cggtggtcat ccagaggctt ttgagtcatc aactcccttta   2160
catcaagcag aggattctca ggtccgccag tacttcccag agacctggct ctgggatctg     2220
tttcctattg gtaactcggg gaaggaggcg gtccacgtca cagttcctga cgccatcacc      2280
gagtggaagg cgatgagttt ctgcacttcc cagtcaagag gcttcgggct ttcacccact      2340
gttggactaa ctgctttcaa gccgttcttt gttgacctga ctctcccctta ctcagtagtc    2400
cgtgggaat cctttcgtct tactgccacc atcttcaatt acctaaagga ttgcatcagg       2460
gttcagactg acctggctaa atcgcatgag taccagctag aatcatgggc agattctcag      2520
acctccagtt gtctctgtgc tgatgacgca aaacccacc actggaacat acagctgtc        2580
aaattgggtc acattaactt tactattagt acaaagattc tggacagcaa tgaaccatgt     2640
gggggccaga agggtttgt tccccaaaag ggccgaagtg acacgctcat caagccagtt       2700
ctcgtcaaac ctgagggagt cctggtggag aagacacaca gctcattgct gtgcccaaaa     2760
ggaaaggtgg catctgaatc tgtctcccctg gagctcccag tggacattgt tcctgactcg    2820
accaaggctt atgttacggt tctgggtaag cagttagaga ttcttgactc agaaaggaaa    2880
aggcgaatgg aggctgcaaa ggtgtggaga acattatgg gcacagccct gcagaacctg     2940
gatggtctgg tgcagatgcc cagtggctgt ggcgagcaga acatggtctt gtttgctccc   3000
atcatctatg tcttgcagta cctggagaag gcagggctgc tgacgaggga gatcaggtct     3060
cgggcagtgg gtttcctgga aatagggtac cagaaggagc tgatgtacaa acacagcaat     3120
ggctcataca gtgccttttgg ggagcgagat ggaaatggaa acacatggct gacagcgttt   3180
gtcacaaaat gctttggcca agctcagaaa ttcatcttca ttgatcccaa gaacatccag    3240
gatgctctca gtggatggc aggaaaccag ctccccagtg ctgctatgc caacgtggga      3300
aatctccttc acacagctat gaagggtggt gttgatgatg aggtctcctt gactgcgtat    3360
gtcacagctg cattgctgga gatgggaaag gatgtagatg acccaatggt gagtcagggt     3420
ctacggtgtc tcaagaattc ggccaccctcc acgaccaacc tctacacaca ggccctgttg   3480
```

-continued

```
gcttacattt tctccctggc tggggaaatg gacatcagaa acattctcct taaacagtta    3540
gatcaacagg ctatcatctc aggagaatcc atttactgga gccagaaacc tactccatca    3600
tcgaacgcca gcccttggtc tgagcctgcg gctgtagatg tggaactcac agcatatgca    3660
ttgttggccc agcttaccaa gcccagcctg actcaaaagg agatagcgaa ggccactagc    3720
atagtggctt ggttggccaa gcaacacaat gcatatgggg gcttctcttc tactcaggat    3780
actgtagttg ctctccaagc tcttgccaaa tatgccacta ccgcctacat gccatctgag    3840
gagatcaacc tggttgtaaa atccactgag aatttccagc gcacattcaa catacagtca    3900
gttaacagat tggtatttca gcaggatacc ctgcccaatg tccctggaat gtacacgttg    3960
gaggcctcag gccagggctg tgtctatgtg cagacggtgt tgagatacaa tattctccct    4020
cccacaaata tgaagacctt tagtcttagt gtggaaatag gaaaagctag atgtgagcaa    4080
ccgacttcac ctcgatcctt gactctcact attcacacca gttatgtggg gagccgtagc    4140
tcttccaata tggctattgt ggaagtgaag atgctatctg ggttcagtcc catggagggc    4200
accaatcagt tacttctcca gcaacccctg gtgaagaagg ttgaatttgg aactgacaca    4260
cttaacattt acttggatga gctcattaag aacactcaga cttacacctt caccatcagc    4320
caaagtgtgc tggtcaccaa cttgaaacca gcaaccatca aggtctatga ctactaccta    4380
ccaggttctt ttaaattatc tcagtacaca attgtgtggt ccatgaacaa tgacagcata    4440
gtggactctg tggcacggca cccagaacca ccccctttca agacagaagc atttattcct    4500
tcacttcctg ggagtgttaa caactga                                         4527
```

```
<210> SEQ ID NO 6
<211> LENGTH: 31
<212> TYPE: PRT
<213> ORGANISM: Homo sapiens

<400> SEQUENCE: 6

Ile Val Ala Trp Leu Ala Lys Gln His Asn Ala Tyr Gly Gly Phe Ser
1               5                   10                  15

Ser Thr Gln Asp Thr Val Val Ala Leu Gln Ala Leu Ala Lys Tyr
            20                  25                  30

<210> SEQ ID NO 7
<211> LENGTH: 30
<212> TYPE: PRT
<213> ORGANISM: Homo sapiens

<400> SEQUENCE: 7

Ala Phe Lys Pro Phe Phe Val Asp Leu Thr Leu Pro Tyr Ser Val Val
1               5                   10                  15

Arg Gly Glu Ser Phe Arg Leu Thr Ala Thr Ile Phe Asn Tyr
            20                  25                  30

<210> SEQ ID NO 8
<211> LENGTH: 32
<212> TYPE: PRT
<213> ORGANISM: Homo sapiens

<400> SEQUENCE: 8

Leu Val Gln Met Pro Ser Gly Cys Gly Glu Gln Asn Met Val Leu Phe
1               5                   10                  15

Ala Pro Ile Ile Tyr Val Leu Gln Tyr Leu Glu Lys Ala Gly Leu Leu
            20                  25                  30
```

```
<210> SEQ ID NO 9
<211> LENGTH: 29
<212> TYPE: PRT
<213> ORGANISM: Homo sapiens

<400> SEQUENCE: 9

Thr Phe Val Gln Thr Asp Lys Pro Leu Tyr Thr Pro Gly Gln Gln Val
1               5                   10                  15

Tyr Phe Arg Ile Val Thr Met Asp Ser Asn Phe Val Pro
            20                  25

<210> SEQ ID NO 10
<211> LENGTH: 33
<212> TYPE: PRT
<213> ORGANISM: Homo sapiens

<400> SEQUENCE: 10

Phe Thr Ile Ser Gln Ser Val Leu Val Thr Asn Leu Lys Pro Ala Thr
1               5                   10                  15

Ile Lys Val Tyr Asp Tyr Tyr Leu Pro Gly Ser Phe Lys Leu Ser Gln
            20                  25                  30

Tyr

<210> SEQ ID NO 11
<211> LENGTH: 24
<212> TYPE: PRT
<213> ORGANISM: Homo sapiens

<400> SEQUENCE: 11

Ser Asn Met Ala Ile Val Glu Val Lys Met Leu Ser Gly Phe Ser Pro
1               5                   10                  15

Met Glu Gly Thr Asn Gln Leu Leu
            20

<210> SEQ ID NO 12
<211> LENGTH: 27
<212> TYPE: PRT
<213> ORGANISM: Homo sapiens

<400> SEQUENCE: 12

Phe Val Asp Leu Thr Leu Pro Tyr Ser Val Val Arg Gly Glu Ser Phe
1               5                   10                  15

Arg Leu Thr Ala Thr Ile Phe Asn Tyr Leu Lys
            20                  25

<210> SEQ ID NO 13
<211> LENGTH: 21
<212> TYPE: PRT
<213> ORGANISM: Homo sapiens

<400> SEQUENCE: 13

Val Pro Asp Ala Ile Thr Glu Trp Lys Ala Met Ser Phe Cys Thr Ser
1               5                   10                  15

Gln Ser Arg Gly Phe
            20

<210> SEQ ID NO 14
<211> LENGTH: 13
<212> TYPE: PRT
<213> ORGANISM: Homo sapiens

<400> SEQUENCE: 14
```

-continued

```
Phe Ser Val Glu Glu Tyr Val Leu Pro Lys Phe Lys Val
1               5                   10

<210> SEQ ID NO 15
<211> LENGTH: 27
<212> TYPE: PRT
<213> ORGANISM: Homo sapiens

<400> SEQUENCE: 15

Trp Met Ala Gly Asn Gln Leu Pro Ser Gly Cys Tyr Ala Asn Val Gly
1               5                   10                  15

Asn Leu Leu His Thr Ala Met Lys Gly Val
            20                  25

<210> SEQ ID NO 16
<211> LENGTH: 10
<212> TYPE: PRT
<213> ORGANISM: Homo sapiens

<400> SEQUENCE: 16

Arg Gln Tyr Phe Pro Glu Thr Trp Leu Trp
1               5                   10

<210> SEQ ID NO 17
<211> LENGTH: 12
<212> TYPE: PRT
<213> ORGANISM: Homo sapiens

<400> SEQUENCE: 17

Asn Thr Trp Leu Thr Ala Phe Val Thr Lys Cys Phe
1               5                   10

<210> SEQ ID NO 18
<211> LENGTH: 17
<212> TYPE: PRT
<213> ORGANISM: Homo sapiens

<400> SEQUENCE: 18

Phe Leu Val Lys Ile Cys Cys Arg Tyr Thr Tyr Gly Lys Pro Met Leu
1               5                   10                  15

Gly

<210> SEQ ID NO 19
<211> LENGTH: 17
<212> TYPE: PRT
<213> ORGANISM: Homo sapiens

<400> SEQUENCE: 19

Met Trp Ala Gln Leu Leu Leu Gly Met Leu Ala Leu Ser Pro Ala Ile
1               5                   10                  15

Ala

<210> SEQ ID NO 20
<211> LENGTH: 179
<212> TYPE: PRT
<213> ORGANISM: Homo sapiens

<400> SEQUENCE: 20

Ser Ser Thr Ile Arg Val Ser Gly Val Cys Tyr Asn Ile Ser Phe Glu
1               5                   10                  15

Glu Asn Lys Lys Val Leu Ile Gln Arg Gln Gly Asn Gly Thr Phe Val
            20                  25                  30
```

```
Gln Thr Asp Lys Pro Leu Tyr Thr Pro Gly Gln Gln Val Tyr Phe Arg
        35                  40                  45

Ile Val Thr Met Asp Ser Asn Phe Val Pro Val Asn Asp Lys Tyr Ser
 50                  55                  60

Met Val Glu Leu Gln Asp Pro Asn Ser Asn Arg Ile Ala Gln Trp Leu
 65                  70                  75                  80

Glu Val Val Pro Glu Gln Gly Ile Val Asp Leu Ser Phe Gln Leu Ala
                 85                  90                  95

Pro Glu Ala Met Leu Gly Thr Tyr Thr Val Ala Val Ala Glu Gly Lys
                100                 105                 110

Thr Phe Gly Thr Phe Ser Val Glu Glu Tyr Val Leu Pro Lys Phe Lys
            115                 120                 125

Val Glu Val Val Glu Pro Lys Glu Leu Ser Thr Val Gln Glu Ser Phe
            130                 135                 140

Leu Val Lys Ile Cys Cys Arg Tyr Thr Tyr Gly Lys Pro Met Leu Gly
145                 150                 155                 160

Ala Val Gln Val Ser Val Cys Gln Lys Ala Asn Thr Tyr Trp Tyr Arg
                165                 170                 175

Glu Val Glu

<210> SEQ ID NO 21
<211> LENGTH: 300
<212> TYPE: PRT
<213> ORGANISM: Homo sapiens

<400> SEQUENCE: 21

Leu Gln Asn Leu Asp Gly Leu Val Gln Met Pro Ser Gly Cys Gly Glu
 1               5                  10                  15

Gln Asn Met Val Leu Phe Ala Pro Ile Ile Tyr Val Leu Gln Tyr Leu
                20                  25                  30

Glu Lys Ala Gly Leu Leu Thr Glu Glu Ile Arg Ser Arg Ala Val Gly
            35                  40                  45

Phe Leu Glu Ile Gly Tyr Gln Lys Glu Leu Met Tyr Lys His Ser Asn
 50                  55                  60

Gly Ser Tyr Ser Ala Phe Gly Glu Arg Asp Gly Asn Gly Asn Thr Trp
 65                  70                  75                  80

Leu Thr Ala Phe Val Thr Lys Cys Phe Gly Gln Ala Gln Lys Phe Ile
                 85                  90                  95

Phe Ile Asp Pro Lys Asn Ile Gln Asp Ala Leu Lys Trp Met Ala Gly
                100                 105                 110

Asn Gln Leu Pro Ser Gly Cys Tyr Ala Asn Val Gly Asn Leu Leu His
            115                 120                 125

Thr Ala Met Lys Gly Gly Val Asp Asp Glu Val Ser Leu Thr Ala Tyr
130                 135                 140

Val Thr Ala Ala Leu Leu Glu Met Gly Lys Asp Val Asp Asp Pro Met
145                 150                 155                 160

Val Ser Gln Gly Leu Arg Cys Leu Lys Asn Ser Ala Thr Ser Thr Thr
                165                 170                 175

Asn Leu Tyr Thr Gln Ala Leu Leu Ala Tyr Ile Phe Ser Leu Ala Gly
            180                 185                 190

Glu Met Asp Ile Arg Asn Ile Leu Leu Lys Gln Leu Asp Gln Gln Ala
        195                 200                 205

Ile Ile Ser Gly Glu Ser Ile Tyr Trp Ser Gln Lys Pro Thr Pro Ser
210                 215                 220
```

-continued

```
Ser Asn Ala Ser Pro Trp Ser Glu Pro Ala Ala Val Asp Val Glu Leu
225                 230                 235                 240

Thr Ala Tyr Ala Leu Leu Ala Gln Leu Thr Lys Pro Ser Leu Thr Gln
            245                 250                 255

Lys Glu Ile Ala Lys Ala Thr Ser Ile Val Ala Trp Leu Ala Lys Gln
                260                 265                 270

His Asn Ala Tyr Gly Gly Phe Ser Ser Thr Gln Asp Thr Val Val Ala
            275                 280                 285

Leu Gln Ala Leu Ala Lys Tyr Ala Thr Thr Ala Tyr
            290                 295                 300
```

<210> SEQ ID NO 22
<211> LENGTH: 137
<212> TYPE: PRT
<213> ORGANISM: Homo sapiens

<400> SEQUENCE: 22

```
Asn Met Lys Thr Phe Ser Leu Ser Val Glu Ile Gly Lys Ala Arg Cys
1               5                   10                  15

Glu Gln Pro Thr Ser Pro Arg Ser Leu Thr Leu Thr Ile His Thr Ser
                20                  25                  30

Tyr Val Gly Ser Arg Ser Ser Asn Met Ala Ile Val Glu Val Lys
            35                  40                  45

Met Leu Ser Gly Phe Ser Pro Met Glu Gly Thr Asn Gln Leu Leu Leu
        50                  55                  60

Gln Gln Pro Leu Val Lys Val Glu Phe Gly Thr Asp Thr Leu Asn
65                  70                  75                  80

Ile Tyr Leu Asp Glu Leu Ile Lys Asn Thr Gln Thr Tyr Thr Phe Thr
                85                  90                  95

Ile Ser Gln Ser Val Leu Val Thr Asn Leu Lys Pro Ala Thr Ile Lys
            100                 105                 110

Val Tyr Asp Tyr Tyr Leu Pro Gly Ser Phe Lys Leu Ser Gln Tyr Thr
        115                 120                 125

Ile Val Trp Ser Met Asn Asn Asp Ser
    130                 135
```

<210> SEQ ID NO 23
<211> LENGTH: 1450
<212> TYPE: PRT
<213> ORGANISM: Homo sapiens

<400> SEQUENCE: 23

```
Leu Leu Leu Val Leu Leu Pro Thr Asp Ala Ser Val Ser Gly Lys Pro
1               5                   10                  15

Gln Tyr Met Val Leu Val Pro Ser Leu Leu His Thr Glu Thr Thr Glu
                20                  25                  30

Lys Gly Cys Val Leu Leu Ser Tyr Leu Asn Glu Thr Val Thr Val Ser
            35                  40                  45

Ala Ser Leu Glu Ser Val Arg Gly Asn Arg Ser Leu Phe Thr Asp Leu
        50                  55                  60

Glu Ala Glu Asn Asp Val Leu His Cys Val Ala Phe Ala Val Pro Lys
65                  70                  75                  80

Ser Ser Ser Asn Glu Glu Val Met Phe Leu Thr Val Gln Val Lys Gly
                85                  90                  95

Pro Thr Gln Glu Phe Lys Lys Arg Thr Thr Val Met Val Lys Asn Glu
            100                 105                 110
```

-continued

```
Asp Ser Leu Val Phe Val Gln Thr Asp Lys Ser Ile Tyr Lys Pro Gly
        115                 120                 125

Gln Thr Val Lys Phe Arg Val Val Ser Met Asp Glu Asn Phe His Pro
    130                 135                 140

Leu Asn Glu Leu Ile Pro Leu Val Tyr Ile Gln Asp Pro Lys Gly Asn
145                 150                 155                 160

Arg Ile Ala Gln Trp Gln Ser Phe Gln Leu Glu Gly Gly Leu Lys Gln
                165                 170                 175

Phe Ser Phe Pro Leu Ser Ser Glu Pro Phe Gln Gly Ser Tyr Lys Val
            180                 185                 190

Val Val Gln Lys Lys Ser Gly Gly Arg Thr Glu His Pro Phe Thr Val
        195                 200                 205

Glu Glu Phe Val Leu Pro Lys Phe Glu Val Gln Val Thr Val Pro Lys
    210                 215                 220

Ile Ile Thr Ile Leu Glu Glu Met Asn Val Ser Val Cys Gly Leu
225                 230                 235                 240

Tyr Thr Tyr Gly Lys Pro Val Pro Gly His Val Thr Val Ser Ile Cys
                245                 250                 255

Arg Lys Tyr Ser Asp Ala Ser Asp Cys His Gly Glu Asp Ser Gln Ala
            260                 265                 270

Phe Cys Glu Lys Phe Ser Gly Gln Leu Asn Ser His Gly Cys Phe Tyr
        275                 280                 285

Gln Gln Val Lys Thr Lys Val Phe Gln Leu Lys Arg Lys Glu Tyr Glu
    290                 295                 300

Met Lys Leu His Thr Glu Ala Gln Ile Gln Glu Glu Gly Thr Val Val
305                 310                 315                 320

Glu Leu Thr Gly Arg Gln Ser Ser Glu Ile Thr Arg Thr Ile Thr Lys
                325                 330                 335

Leu Ser Phe Val Lys Val Asp Ser His Phe Arg Gln Gly Ile Pro Phe
            340                 345                 350

Phe Gly Gln Val Arg Leu Val Asp Gly Lys Gly Val Pro Ile Pro Asn
        355                 360                 365

Lys Val Ile Phe Ile Arg Gly Asn Glu Ala Asn Tyr Tyr Ser Asn Ala
    370                 375                 380

Thr Thr Asp Glu His Gly Leu Val Gln Phe Ser Ile Asn Thr Thr Asn
385                 390                 395                 400

Val Met Gly Thr Ser Leu Thr Val Arg Val Asn Tyr Lys Asp Arg Ser
                405                 410                 415

Pro Cys Tyr Gly Tyr Gln Trp Val Ser Glu Glu His Glu Glu Ala His
            420                 425                 430

His Thr Ala Tyr Leu Val Phe Ser Pro Ser Lys Ser Phe Val His Leu
        435                 440                 445

Glu Pro Met Ser His Glu Leu Pro Cys Gly His Thr Gln Thr Val Gln
    450                 455                 460

Ala His Tyr Ile Leu Asn Gly Gly Thr Leu Leu Gly Leu Lys Lys Leu
465                 470                 475                 480

Ser Phe Tyr Tyr Leu Ile Met Ala Lys Gly Gly Ile Val Arg Thr Gly
                485                 490                 495

Thr His Gly Leu Leu Val Lys Gln Glu Asp Met Lys Gly His Phe Ser
            500                 505                 510

Ile Ser Ile Pro Val Lys Ser Asp Ile Ala Pro Val Ala Arg Leu Leu
        515                 520                 525

Ile Tyr Ala Val Leu Pro Thr Gly Asp Val Ile Gly Asp Ser Ala Lys
```

```
              530                 535                 540
Tyr Asp Val Glu Asn Cys Leu Ala Asn Lys Val Asp Leu Ser Phe Ser
545                 550                 555                 560

Pro Ser Gln Ser Leu Pro Ala Ser His Ala His Leu Arg Val Thr Ala
                565                 570                 575

Ala Pro Gln Ser Val Cys Ala Leu Arg Ala Val Asp Gln Ser Val Leu
                580                 585                 590

Leu Met Lys Pro Asp Ala Glu Leu Ser Ala Ser Ser Val Tyr Asn Leu
                595                 600                 605

Leu Pro Glu Lys Asp Leu Thr Gly Phe Pro Gly Pro Leu Asn Asp Gln
610                 615                 620

Asp Asp Glu Asp Cys Ile Asn Arg His Asn Val Tyr Ile Asn Gly Ile
625                 630                 635                 640

Thr Tyr Thr Pro Val Ser Ser Thr Asn Glu Lys Asp Met Tyr Ser Phe
                645                 650                 655

Leu Glu Asp Met Gly Leu Lys Ala Phe Thr Asn Ser Lys Ile Arg Lys
                660                 665                 670

Pro Lys Met Cys Pro Gln Leu Gln Gln Tyr Glu Met His Gly Pro Glu
                675                 680                 685

Gly Leu Arg Val Gly Phe Tyr Glu Ser Asp Val Met Gly Arg Gly His
690                 695                 700

Ala Arg Leu Val His Val Glu Glu Pro His Thr Glu Thr Val Arg Lys
705                 710                 715                 720

Tyr Phe Pro Glu Thr Trp Ile Trp Asp Leu Val Val Asn Ser Ala
                725                 730                 735

Gly Val Ala Glu Val Gly Val Thr Val Pro Asp Thr Ile Thr Glu Trp
                740                 745                 750

Lys Ala Gly Ala Phe Cys Leu Ser Glu Asp Ala Gly Leu Gly Ile Ser
                755                 760                 765

Ser Thr Ala Ser Leu Arg Ala Phe Gln Pro Phe Phe Val Glu Leu Thr
770                 775                 780

Met Pro Tyr Ser Val Ile Arg Gly Glu Ala Phe Thr Leu Lys Ala Thr
785                 790                 795                 800

Val Leu Asn Tyr Leu Pro Lys Cys Ile Arg Val Ser Val Gln Leu Glu
                805                 810                 815

Ala Ser Pro Ala Phe Leu Ala Val Pro Val Glu Lys Glu Gln Ala Pro
                820                 825                 830

His Cys Ile Cys Ala Asn Gly Arg Gln Thr Val Ser Trp Ala Val Thr
                835                 840                 845

Pro Lys Ser Leu Gly Asn Val Asn Phe Thr Val Ser Ala Glu Ala Leu
                850                 855                 860

Glu Ser Gln Glu Leu Cys Gly Thr Glu Val Pro Ser Val Pro Glu His
865                 870                 875                 880

Gly Arg Lys Asp Thr Val Ile Lys Pro Leu Val Glu Pro Glu Gly
                885                 890                 895

Leu Glu Lys Glu Thr Thr Phe Asn Ser Leu Leu Cys Pro Ser Gly Gly
                900                 905                 910

Glu Val Ser Glu Glu Leu Ser Leu Lys Leu Pro Pro Asn Val Val Glu
                915                 920                 925

Glu Ser Ala Arg Ala Ser Val Ser Val Leu Gly Asp Ile Leu Gly Ser
                930                 935                 940

Ala Met Gln Asn Thr Gln Asn Leu Leu Gln Met Pro Tyr Gly Cys Gly
945                 950                 955                 960
```

-continued

```
Glu Gln Asn Met Val Leu Phe Ala Pro Asn Ile Tyr Val Leu Asp Tyr
            965                 970                 975

Leu Asn Glu Thr Gln Gln Leu Thr Pro Glu Val Lys Ser Lys Ala Ile
            980                 985                 990

Gly Tyr Leu Asn Thr Gly Tyr Gln Arg Gln Leu Asn Tyr Lys His Tyr
            995                1000                1005

Asp Gly Ser Tyr Ser Thr Phe Gly Glu Arg Tyr Gly Arg Asn Gln
        1010                1015                1020

Gly Asn Thr Trp Leu Thr Ala Phe Val Leu Lys Thr Phe Ala Gln
        1025                1030                1035

Ala Arg Ala Tyr Ile Phe Ile Asp Glu Ala His Ile Thr Gln Ala
        1040                1045                1050

Leu Ile Trp Leu Ser Gln Arg Gln Lys Asp Asn Gly Cys Phe Arg
        1055                1060                1065

Ser Ser Gly Ser Leu Leu Asn Asn Ala Ile Lys Gly Gly Val Glu
        1070                1075                1080

Asp Glu Val Thr Leu Ser Ala Tyr Ile Thr Ile Ala Leu Leu Glu
        1085                1090                1095

Ile Pro Leu Thr Val Thr His Pro Val Val Arg Asn Ala Leu Phe
        1100                1105                1110

Cys Leu Glu Ser Ala Trp Lys Thr Ala Gln Glu Gly Asp His Gly
        1115                1120                1125

Ser His Val Tyr Thr Lys Ala Leu Leu Ala Tyr Ala Phe Ala Leu
        1130                1135                1140

Ala Gly Asn Gln Asp Lys Arg Lys Glu Val Leu Lys Ser Leu Asn
        1145                1150                1155

Glu Glu Ala Val Lys Lys Asp Asn Ser Val His Trp Glu Arg Pro
        1160                1165                1170

Gln Lys Pro Lys Ala Pro Val Gly His Phe Tyr Glu Pro Gln Ala
        1175                1180                1185

Pro Ser Ala Glu Val Glu Met Thr Ser Tyr Val Leu Leu Ala Tyr
        1190                1195                1200

Leu Thr Ala Gln Pro Ala Pro Thr Ser Glu Asp Leu Thr Ser Ala
        1205                1210                1215

Thr Asn Ile Val Lys Trp Ile Thr Lys Gln Gln Asn Ala Gln Gly
        1220                1225                1230

Gly Phe Ser Ser Thr Gln Asp Thr Val Val Ala Leu His Ala Leu
        1235                1240                1245

Ser Lys Tyr Gly Ala Ala Thr Phe Thr Arg Thr Gly Lys Ala Ala
        1250                1255                1260

Gln Val Thr Ile Gln Ser Ser Gly Thr Phe Ser Ser Lys Phe Gln
        1265                1270                1275

Val Asp Asn Asn Asn Arg Leu Leu Leu Gln Gln Val Ser Leu Pro
        1280                1285                1290

Glu Leu Pro Gly Glu Tyr Ser Met Lys Val Thr Gly Glu Gly Cys
        1295                1300                1305

Val Tyr Leu Gln Thr Ser Leu Lys Tyr Asn Ile Leu Pro Glu Lys
        1310                1315                1320

Glu Glu Phe Pro Phe Ala Leu Gly Val Gln Thr Leu Pro Gln Thr
        1325                1330                1335

Cys Asp Glu Pro Lys Ala His Thr Ser Phe Gln Ile Ser Leu Ser
        1340                1345                1350
```

-continued

```
Val Ser Tyr Thr Gly Ser Arg Ser Ala Ser Asn Met Ala Ile Val
    1355                1360                1365

Asp Val Lys Met Val Ser Gly Phe Ile Pro Leu Lys Pro Thr Val
    1370                1375                1380

Lys Met Leu Glu Arg Ser Asn His Val Ser Arg Thr Glu Val Ser
    1385                1390                1395

Ser Asn His Val Leu Ile Tyr Leu Asp Lys Val Ser Asn Gln Thr
    1400                1405                1410

Leu Ser Leu Phe Phe Thr Val Leu Gln Asp Val Pro Val Arg Asp
    1415                1420                1425

Leu Lys Pro Ala Ile Val Lys Val Tyr Asp Tyr Tyr Glu Thr Asp
    1430                1435                1440

Glu Phe Ala Ile Ala Glu Tyr
    1445                1450

<210> SEQ ID NO 24
<211> LENGTH: 1451
<212> TYPE: PRT
<213> ORGANISM: Homo sapiens

<400> SEQUENCE: 24

Leu Leu Leu Leu Val Leu Val Pro Thr Asp Ala Ser Val Ser Gly Lys
1               5                   10                  15

Pro Gln Tyr Met Val Leu Val Pro Ser Leu Leu His Thr Glu Thr Thr
                20                  25                  30

Glu Lys Gly Cys Val Leu Leu Ser Tyr Leu Asn Glu Thr Val Thr Val
            35                  40                  45

Ser Ala Ser Leu Glu Ser Val Arg Gly Asn Arg Ser Leu Phe Thr Asp
        50                  55                  60

Leu Glu Ala Glu Asn Asp Val Leu His Cys Val Ala Phe Ala Val Pro
65                  70                  75                  80

Lys Ser Ser Ser Asn Glu Glu Val Met Phe Leu Thr Val Gln Val Lys
                85                  90                  95

Gly Pro Thr Gln Glu Phe Lys Lys Arg Thr Thr Val Met Val Lys Asn
            100                 105                 110

Glu Asp Ser Leu Val Phe Val Gln Thr Asp Lys Ser Ile Tyr Lys Pro
        115                 120                 125

Gly Gln Thr Val Lys Phe Arg Val Val Ser Met Asp Glu Asn Phe His
    130                 135                 140

Pro Leu Asn Glu Leu Ile Pro Leu Val Tyr Ile Gln Asp Pro Lys Gly
145                 150                 155                 160

Asn Arg Ile Ala Gln Trp Gln Ser Phe Gln Leu Glu Gly Gly Leu Lys
                165                 170                 175

Gln Phe Ser Phe Pro Leu Ser Ser Glu Pro Phe Gln Gly Ser Tyr Lys
            180                 185                 190

Val Val Val Gln Lys Lys Ser Gly Gly Arg Thr Glu His Pro Phe Thr
        195                 200                 205

Val Glu Glu Phe Val Leu Pro Lys Phe Glu Val Gln Val Thr Val Pro
    210                 215                 220

Lys Ile Ile Thr Ile Leu Glu Glu Met Asn Val Ser Val Cys Gly
225                 230                 235                 240

Leu Tyr Thr Tyr Gly Lys Pro Val Pro Gly His Val Thr Val Ser Ile
                245                 250                 255

Cys Arg Lys Tyr Ser Asp Ala Ser Asp Cys His Gly Glu Asp Ser Gln
            260                 265                 270
```

```
Ala Phe Cys Glu Lys Phe Ser Gly Gln Leu Asn Ser His Gly Cys Phe
            275                 280                 285
Tyr Gln Gln Val Lys Thr Lys Val Phe Gln Leu Lys Arg Lys Glu Tyr
        290                 295                 300
Glu Met Lys Leu His Thr Glu Ala Gln Ile Gln Glu Glu Gly Thr Val
305                 310                 315                 320
Val Glu Leu Thr Gly Arg Gln Ser Ser Glu Ile Thr Arg Thr Ile Thr
                325                 330                 335
Lys Leu Ser Phe Val Lys Val Asp Ser His Phe Arg Gln Gly Ile Pro
            340                 345                 350
Phe Phe Gly Gln Val Arg Leu Val Asp Gly Lys Gly Val Pro Ile Pro
        355                 360                 365
Asn Lys Val Ile Phe Ile Arg Gly Asn Glu Ala Asn Tyr Tyr Ser Asn
    370                 375                 380
Ala Thr Thr Asp Glu His Gly Leu Val Gln Phe Ser Ile Asn Thr Thr
385                 390                 395                 400
Asn Val Met Gly Thr Ser Leu Thr Val Arg Val Asn Tyr Lys Asp Arg
                405                 410                 415
Ser Pro Cys Tyr Gly Tyr Gln Trp Val Ser Glu His Glu Glu Ala
            420                 425                 430
His His Thr Ala Tyr Leu Val Phe Ser Pro Ser Lys Ser Phe Val His
        435                 440                 445
Leu Glu Pro Met Ser His Glu Leu Pro Cys Gly His Thr Gln Thr Val
    450                 455                 460
Gln Ala His Tyr Ile Leu Asn Gly Gly Thr Leu Leu Gly Leu Lys Lys
465                 470                 475                 480
Leu Ser Phe Tyr Tyr Leu Ile Met Ala Lys Gly Gly Ile Val Arg Thr
                485                 490                 495
Gly Thr His Gly Leu Leu Val Lys Gln Glu Asp Met Lys Gly His Phe
            500                 505                 510
Ser Ile Ser Ile Pro Val Lys Ser Asp Ile Ala Pro Val Ala Arg Leu
        515                 520                 525
Leu Ile Tyr Ala Val Leu Pro Thr Gly Asp Val Ile Gly Asp Ser Ala
    530                 535                 540
Lys Tyr Asp Val Glu Asn Cys Leu Ala Asn Lys Val Asp Leu Ser Phe
545                 550                 555                 560
Ser Pro Ser Gln Ser Leu Pro Ala Ser His Ala His Leu Arg Val Thr
                565                 570                 575
Ala Ala Pro Gln Ser Val Cys Ala Leu Arg Ala Val Asp Gln Ser Val
            580                 585                 590
Leu Leu Met Lys Pro Asp Ala Glu Leu Ser Ala Ser Val Tyr Asn
        595                 600                 605
Leu Leu Pro Glu Lys Asp Leu Thr Gly Phe Pro Gly Pro Leu Asn Asp
    610                 615                 620
Gln Asp Asp Glu Asp Cys Ile Asn Arg His Asn Val Tyr Ile Asn Gly
625                 630                 635                 640
Ile Thr Tyr Thr Pro Val Ser Ser Thr Asn Glu Lys Asp Met Tyr Ser
                645                 650                 655
Phe Leu Glu Asp Met Gly Leu Lys Ala Phe Thr Asn Ser Lys Ile Arg
            660                 665                 670
Lys Pro Lys Met Cys Pro Gln Leu Gln Gln Tyr Glu Met His Gly Pro
        675                 680                 685
```

-continued

```
Glu Gly Leu Arg Val Gly Phe Tyr Glu Ser Asp Val Met Gly Arg Gly
    690             695                 700

His Ala Arg Leu Val His Val Glu Glu Pro His Thr Glu Thr Val Arg
705             710                 715                 720

Lys Tyr Phe Ala Glu Thr Trp Ile Trp Asp Leu Val Val Asn Ser
            725                 730                 735

Ala Gly Val Ala Glu Val Gly Val Thr Val Pro Asp Thr Ile Thr Glu
            740                 745                 750

Trp Lys Ala Gly Ala Phe Cys Leu Ser Glu Asp Ala Gly Leu Gly Ile
            755                 760                 765

Ser Ser Thr Ala Ser Leu Arg Ala Phe Gln Pro Phe Phe Val Glu Leu
770             775                 780

Thr Met Pro Tyr Ser Val Ile Arg Gly Glu Ala Phe Thr Leu Lys Ala
785             790                 795                 800

Thr Val Leu Asn Tyr Leu Pro Lys Cys Ile Arg Val Ser Val Gln Leu
                805                 810                 815

Glu Ala Ser Pro Ala Phe Leu Ala Val Pro Val Glu Lys Glu Gln Ala
            820                 825                 830

Pro His Cys Ile Cys Ala Asn Gly Arg Gln Thr Val Ser Trp Ala Val
            835                 840                 845

Thr Pro Lys Ser Leu Gly Asn Val Asn Phe Thr Val Ser Ala Glu Ala
850             855                 860

Leu Glu Ser Gln Glu Leu Cys Gly Thr Glu Val Pro Ser Val Pro Glu
865             870                 875                 880

His Gly Arg Lys Asp Thr Val Ile Lys Pro Leu Leu Val Glu Pro Glu
                885                 890                 895

Gly Leu Glu Lys Glu Thr Thr Phe Asn Ser Leu Leu Cys Pro Ser Gly
            900                 905                 910

Gly Glu Val Ser Glu Glu Leu Ser Leu Lys Leu Pro Pro Asn Val Val
            915                 920                 925

Glu Glu Ser Ala Arg Ala Ser Val Ser Val Leu Gly Asp Ile Leu Gly
930             935                 940

Ser Ala Met Gln Asn Thr Gln Asn Leu Leu Gln Met Pro Tyr Gly Cys
945             950                 955                 960

Gly Glu Gln Asn Met Val Leu Phe Ala Pro Asn Ile Tyr Val Leu Asp
            965                 970                 975

Tyr Leu Asn Glu Thr Gln Gln Leu Thr Pro Glu Ile Lys Ser Lys Ala
            980                 985                 990

Ile Gly Tyr Leu Asn Thr Gly Tyr Gln Arg Gln Leu Asn Tyr Lys His
            995                 1000                1005

Tyr Asp Gly Ser Tyr Ser Thr Phe Gly Glu Arg Tyr Gly Arg Asn
    1010            1015                1020

Gln Gly Asn Thr Trp Leu Thr Ala Phe Val Leu Lys Thr Phe Ala
    1025            1030                1035

Gln Ala Arg Ala Tyr Ile Phe Ile Asp Glu Ala His Ile Thr Gln
    1040            1045                1050

Ala Leu Ile Trp Leu Ser Gln Arg Gln Lys Asp Asn Gly Cys Phe
    1055            1060                1065

Arg Ser Ser Gly Ser Leu Leu Asn Asn Ala Ile Lys Gly Gly Val
    1070            1075                1080

Glu Asp Glu Val Thr Leu Ser Ala Tyr Ile Thr Ile Ala Leu Leu
    1085            1090                1095

Glu Ile Leu Leu Thr Val Thr His Pro Val Val Arg Asn Ala Leu
```

```
                    1100                1105                1110
Phe Cys Leu Glu Ser Ala Trp Lys Thr Ala Gln Glu Gly Asp His
    1115                1120                1125
Gly Ser His Val Tyr Thr Lys Ala Leu Leu Ala Tyr Ala Phe Ala
    1130                1135                1140
Leu Ala Gly Asn Gln Asp Lys Arg Lys Glu Val Leu Lys Ser Leu
    1145                1150                1155
Asn Glu Glu Ala Val Lys Lys Asp Asn Ser Val His Trp Glu Arg
    1160                1165                1170
Pro Gln Lys Pro Lys Ala Pro Val Gly His Phe Tyr Glu Pro Gln
    1175                1180                1185
Ala Pro Ser Ala Glu Val Glu Met Thr Ser Tyr Val Leu Leu Ala
    1190                1195                1200
Tyr Leu Thr Ala Gln Pro Ala Pro Thr Ser Glu Asp Leu Thr Ser
    1205                1210                1215
Ala Thr Asn Ile Val Lys Trp Ile Thr Lys Gln Gln Asn Ala Gln
    1220                1225                1230
Gly Gly Phe Ser Ser Thr Gln His Thr Val Val Ala Leu His Ala
    1235                1240                1245
Leu Ser Lys Tyr Gly Ala Ala Thr Phe Thr Arg Thr Gly Lys Ala
    1250                1255                1260
Ala Gln Val Thr Ile Gln Ser Ser Gly Thr Phe Ser Ser Lys Phe
    1265                1270                1275
Gln Val Asp Asn Asn Asn Arg Leu Leu Leu Gln Gln Val Ser Leu
    1280                1285                1290
Pro Glu Leu Pro Gly Glu Tyr Ser Met Lys Val Thr Gly Glu Gly
    1295                1300                1305
Cys Val Tyr Leu Gln Thr Ser Leu Lys Tyr Asn Ile Leu Pro Glu
    1310                1315                1320
Lys Glu Glu Phe Pro Phe Ala Leu Gly Val Gln Thr Leu Pro Gln
    1325                1330                1335
Thr Cys Asp Glu Pro Lys Ala His Thr Ser Phe Gln Ile Ser Leu
    1340                1345                1350
Ser Val Ser Tyr Thr Gly Ser Arg Ser Ala Ser Asn Met Ala Ile
    1355                1360                1365
Val Asp Val Lys Met Val Ser Gly Phe Ile Pro Leu Lys Pro Thr
    1370                1375                1380
Val Lys Met Leu Glu Arg Ser Asn His Val Ser Arg Thr Glu Val
    1385                1390                1395
Ser Ser Asn His Val Leu Ile Tyr Leu Asp Lys Val Ser Asn Gln
    1400                1405                1410
Thr Leu Ser Leu Phe Phe Thr Val Leu Gln Asp Val Pro Val Arg
    1415                1420                1425
Asp Leu Lys Pro Ala Ile Val Lys Val Tyr Asp Tyr Tyr Glu Thr
    1430                1435                1440
Asp Glu Phe Ala Ile Ala Glu Tyr
    1445                1450

<210> SEQ ID NO 25
<211> LENGTH: 1491
<212> TYPE: PRT
<213> ORGANISM: hono sapiens

<400> SEQUENCE: 25
```

-continued

```
Glu Glu Leu Pro Asn Tyr Leu Val Thr Leu Pro Ala Arg Leu Asn Phe
1               5                   10                  15

Pro Ser Val Gln Lys Val Cys Leu Asp Leu Ser Pro Gly Tyr Ser Asp
                20                  25                  30

Val Lys Phe Thr Val Thr Leu Glu Thr Lys Asp Lys Thr Gln Lys Leu
            35                  40                  45

Leu Glu Tyr Ser Gly Leu Lys Lys Arg His Leu His Cys Ile Ser Phe
50                      55                  60

Leu Val Pro Pro Ala Gly Gly Thr Glu Glu Val Ala Thr Ile Arg
65              70                  75                  80

Val Ser Gly Val Gly Asn Asn Ile Ser Phe Glu Glu Lys Lys Lys Val
                85                  90                  95

Leu Ile Gln Arg Gln Gly Asn Gly Thr Phe Val Gln Thr Asp Lys Pro
            100                 105                 110

Leu Tyr Thr Pro Gly Gln Gln Val Tyr Phe Arg Ile Val Thr Met Asp
        115                 120                 125

Ser Asn Phe Val Pro Val Asn Asp Lys Tyr Ser Met Val Glu Leu Gln
    130                 135                 140

Asp Pro Asn Ser Asn Arg Ile Ala Gln Trp Leu Glu Val Val Pro Glu
145                 150                 155                 160

Gln Gly Ile Val Asp Leu Ser Phe Gln Leu Ala Pro Glu Ala Met Leu
                165                 170                 175

Gly Thr Tyr Thr Val Ala Val Ala Glu Gly Lys Thr Phe Gly Thr Phe
            180                 185                 190

Ser Val Glu Glu Tyr Val Leu Pro Lys Phe Lys Val Glu Val Val Glu
        195                 200                 205

Pro Lys Glu Leu Ser Thr Val Gln Glu Ser Phe Leu Val Lys Ile Cys
    210                 215                 220

Cys Arg Tyr Thr Tyr Gly Lys Pro Met Leu Gly Ala Val Gln Val Ser
225                 230                 235                 240

Val Cys Gln Lys Ala Asn Thr Tyr Trp Tyr Arg Glu Val Glu Arg Glu
                245                 250                 255

Gln Leu Pro Asp Lys Cys Arg Asn Leu Ser Gly Gln Thr Asp Lys Thr
            260                 265                 270

Gly Cys Phe Ser Ala Pro Val Asp Met Ala Thr Phe Asp Leu Ile Gly
        275                 280                 285

Tyr Ala Tyr Ser His Gln Ile Asn Ile Val Ala Thr Val Val Glu Glu
    290                 295                 300

Gly Thr Gly Val Glu Ala Asn Ala Thr Gln Asn Ile Tyr Ile Ser Pro
305                 310                 315                 320

Gln Met Gly Ser Met Thr Phe Glu Asp Thr Ser Asn Phe Tyr His Pro
                325                 330                 335

Asn Phe Pro Phe Ser Gly Lys Ile Arg Val Arg Gly His Asp Asp Ser
            340                 345                 350

Phe Leu Lys Asn His Leu Val Phe Leu Val Ile Tyr Gly Thr Asn Gly
        355                 360                 365

Thr Phe Asn Gln Thr Leu Val Thr Asp Asn Asn Gly Leu Ala Pro Phe
    370                 375                 380

Thr Leu Glu Thr Ser Gly Trp Asn Gly Thr Asp Val Ser Leu Glu Gly
385                 390                 395                 400

Lys Phe Gln Met Glu Asp Leu Val Tyr Asn Pro Glu Gln Val Pro Arg
                405                 410                 415

Tyr Tyr Gln Asn Ala Tyr Leu His Leu Arg Pro Phe Tyr Ser Thr Thr
```

-continued

```
              420             425             430
Arg Ser Phe Leu Gly Ile His Arg Leu Asn Gly Pro Leu Lys Cys Gly
            435                 440                 445
Gln Pro Gln Glu Val Leu Val Asp Tyr Tyr Ile Asp Pro Ala Asp Ala
            450                 455                 460
Ser Pro Asp Gln Glu Ile Ser Phe Ser Tyr Tyr Leu Ile Gly Lys Gly
465                 470                 475                 480
Ser Leu Val Met Glu Gly Gln Lys His Leu Asn Ser Lys Lys Lys Gly
                485                 490                 495
Leu Lys Ala Ser Phe Ser Leu Ser Leu Thr Phe Thr Ser Arg Leu Ala
                500                 505                 510
Pro Asp Pro Ser Leu Val Ile Tyr Ala Ile Phe Pro Ser Gly Gly Val
                515                 520                 525
Val Ala Asp Lys Ile Gln Phe Ser Val Gly Met Cys Phe Asp Asn Gln
            530                 535                 540
Val Ser Leu Gly Phe Ser Pro Ser Gln Gln Leu Pro Gly Ala Glu Val
545                 550                 555                 560
Glu Leu Gln Leu Gln Ala Ala Pro Gly Ser Leu Cys Ala Leu Arg Ala
                565                 570                 575
Val Asp Glu Ser Val Leu Leu Arg Pro Asp Arg Glu Leu Ser Asn
                580                 585                 590
Arg Ser Val Tyr Gly Met Phe Pro Phe Trp Tyr Gly His Tyr Pro Tyr
            595                 600                 605
Gln Val Ala Glu Tyr Asp Gln Cys Pro Val Ser Gly Pro Trp Asp Phe
            610                 615                 620
Pro Gln Pro Leu Ile Asp Pro Met Pro Gln Gly His Ser Ser Gln Arg
625                 630                 635                 640
Ser Ile Ile Trp Arg Pro Ser Phe Ser Glu Gly Thr Asp Leu Phe Ser
                645                 650                 655
Phe Phe Arg Asp Val Gly Leu Lys Ile Leu Ser Asn Ala Lys Ile Lys
                660                 665                 670
Lys Pro Val Asp Cys Ser His Arg Ser Pro Glu Tyr Ser Thr Ala Met
            675                 680                 685
Gly Gly Gly Gly His Pro Glu Ala Phe Glu Ser Ser Thr Pro Leu His
            690                 695                 700
Gln Ala Glu Asp Ser Gln Val Arg Gln Tyr Phe Pro Glu Thr Trp Leu
705                 710                 715                 720
Trp Asp Leu Phe Pro Ile Gly Asn Ser Gly Lys Glu Ala Val His Val
                725                 730                 735
Thr Val Pro Asp Ala Ile Thr Glu Trp Lys Ala Met Ser Phe Cys Thr
                740                 745                 750
Ser Gln Ser Arg Gly Phe Gly Leu Ser Pro Thr Val Gly Leu Thr Ala
            755                 760                 765
Phe Lys Pro Phe Phe Val Asp Leu Thr Leu Pro Tyr Ser Val Val Arg
            770                 775                 780
Gly Glu Ser Phe Arg Leu Thr Ala Thr Ile Phe Asn Tyr Leu Lys Asp
785                 790                 795                 800
Cys Ile Arg Val Gln Thr Asp Leu Ala Lys Ser His Glu Tyr Gln Leu
                805                 810                 815
Glu Ser Trp Ala Asp Ser Gln Thr Ser Ser Cys Leu Cys Ala Asp Asp
                820                 825                 830
Ala Lys Thr His His Trp Asn Ile Thr Ala Val Lys Leu Gly His Ile
            835                 840                 845
```

-continued

```
Asn Phe Thr Ile Ser Thr Lys Ile Leu Asp Ser Asn Glu Pro Cys Gly
850                 855                 860
Gly Gln Lys Gly Phe Val Pro Gln Lys Gly Arg Ser Asp Thr Leu Ile
865                 870                 875                 880
Lys Pro Val Leu Val Lys Pro Glu Gly Val Leu Val Glu Lys Thr His
                    885                 890                 895
Ser Ser Leu Leu Cys Pro Lys Gly Lys Val Ala Ser Glu Ser Val Ser
                900                 905                 910
Leu Glu Leu Pro Val Asp Ile Val Pro Asp Ser Thr Lys Ala Tyr Val
                915                 920                 925
Thr Val Leu Gly Lys Gln Leu Glu Ile Leu Asp Ser Glu Arg Lys Arg
930                 935                 940
Arg Met Glu Ala Ala Lys Val Trp Arg Asp Ile Met Gly Thr Ala Leu
945                 950                 955                 960
Gln Asn Leu Asp Gly Leu Val Gln Met Pro Ser Gly Cys Gly Glu Gln
                    965                 970                 975
Asn Met Val Leu Phe Ala Pro Ile Ile Tyr Val Leu Gln Tyr Leu Glu
                980                 985                 990
Lys Ala Gly Leu Leu Thr Glu Glu  Ile Arg Ser Arg Ala  Val Gly Phe
                995                 1000                1005
Leu Glu  Ile Gly Tyr Gln Lys  Glu Leu Met Tyr Lys  His Ser Asn
    1010                1015                1020
Gly Ser  Tyr Ser Ala Phe Gly  Glu Arg Asp Gly Asn  Gly Asn Thr
    1025                1030                1035
Trp Leu  Thr Ala Phe Val Thr  Lys Cys Phe Gly Gln  Ala Gln Lys
    1040                1045                1050
Phe Ile  Phe Ile Asp Pro Lys  Asn Ile Gln Asp Ala  Leu Lys Trp
    1055                1060                1065
Met Ala  Gly Asn Gln Leu Pro  Ser Gly Cys Tyr Ala  Asn Val Gly
    1070                1075                1080
Asn Leu  Leu His Thr Ala Met  Lys Gly Gly Val Asp  Asp Glu Val
    1085                1090                1095
Ser Leu  Thr Ala Tyr Val Thr  Ala Ala Leu Leu Glu  Met Gly Lys
    1100                1105                1110
Asp Val  Asp Asp Pro Met Val  Ser Gln Gly Leu Arg  Cys Leu Lys
    1115                1120                1125
Asn Ser  Ala Thr Ser Thr Thr  Asn Leu Tyr Thr Gln  Ala Leu Leu
    1130                1135                1140
Ala Tyr  Ile Phe Ser Leu Ala  Gly Glu Met Asp Ile  Arg Asn Ile
    1145                1150                1155
Leu Leu  Lys Gln Leu Asp Gln  Gln Ala Ile Ile Ser  Gly Glu Ser
    1160                1165                1170
Ile Tyr  Trp Ser Gln Lys Pro  Thr Pro Ser Ser Asn  Ala Ser Pro
    1175                1180                1185
Trp Ser  Glu Pro Ala Ala Val  Asp Val Glu Leu Thr  Ala Tyr Ala
    1190                1195                1200
Leu Leu  Ala Gln Leu Thr Lys  Pro Ser Leu Thr Gln  Lys Glu Ile
    1205                1210                1215
Ala Lys  Ala Thr Ser Ile Val  Ala Trp Leu Ala Lys  Gln His Asn
    1220                1225                1230
Ala Tyr  Gly Gly Phe Ser Ser  Thr Gln Asp Thr Val  Val Ala Leu
    1235                1240                1245
```

```
Gln Ala Leu Ala Lys Tyr Ala Thr Thr Ala Tyr Met Pro Ser Glu
    1250            1255                1260
Glu Ile Asn Leu Val Val Lys Ser Thr Glu Asn Phe Gln Arg Thr
    1265            1270                1275
Phe Asn Ile Gln Ser Val Asn Arg Leu Val Phe Gln Gln Asp Thr
    1280            1285                1290
Leu Pro Asn Val Pro Gly Met Tyr Thr Leu Glu Ala Ser Gly Gln
    1295            1300                1305
Gly Cys Val Tyr Val Gln Thr Val Leu Arg Tyr Asn Ile Leu Pro
    1310            1315                1320
Pro Thr Asn Met Lys Thr Phe Ser Leu Ser Val Glu Ile Gly Lys
    1325            1330                1335
Ala Arg Cys Glu Gln Pro Thr Ser Pro Arg Ser Leu Thr Leu Thr
    1340            1345                1350
Ile His Thr Ser Tyr Val Gly Ser Arg Ser Ser Asn Met Ala
    1355            1360                1365
Ile Val Glu Val Lys Met Leu Ser Gly Phe Ser Pro Met Glu Gly
    1370            1375                1380
Thr Asn Gln Leu Leu Leu Gln Pro Leu Val Lys Lys Val Glu
    1385            1390                1395
Phe Gly Thr Asp Thr Leu Asn Ile Tyr Leu Asp Glu Leu Ile Lys
    1400            1405                1410
Asn Thr Gln Thr Tyr Thr Phe Thr Ile Ser Gln Ser Val Leu Val
    1415            1420                1425
Thr Asn Leu Lys Pro Ala Thr Ile Lys Val Tyr Asp Tyr Tyr Leu
    1430            1435                1440
Pro Gly Ser Phe Lys Leu Ser Gln Tyr Thr Ile Val Trp Ser Met
    1445            1450                1455
Asn Asn Asp Ser Ile Val Asp Ser Val Ala Arg His Pro Glu Pro
    1460            1465                1470
Pro Pro Phe Lys Thr Glu Ala Phe Ile Pro Ser Leu Pro Gly Ser
    1475            1480                1485
Val Asn Asn
    1490

<210> SEQ ID NO 26
<211> LENGTH: 388
<212> TYPE: DNA
<213> ORGANISM: homo sapiens
<220> FEATURE:
<221> NAME/KEY: misc_feature
<222> LOCATION: (1)..(388)
<223> OTHER INFORMATION: n=G, A, T, or C

<400> SEQUENCE: 26
attgcagtca cagatctcca gaatacagca ctgctatggg tgcaggcggt ggtcatccag      60
aggcttttga gtcatcaact cctttacatc aagcagagga ttctcaggtc cgccagtact     120
tcccagagac ctggctctgg gatctgtttc ctattggtaa ctcggggaag gaggcggtcc     180
acgtcacagt tcctgacgcc atcaccgagt ggaaggcgat gagtttctgc acttcccaga     240
caagaggctt cgggctttca cccactgttg gactaactgc tttcaagcca ttctttgttg     300
acctgactct cccttactca gtagtccgtg gggaatcctt tcgtcttact gccaccatct     360
tcaattacct aaaggattgc atcagggn                                        388

<210> SEQ ID NO 27
```

<211> LENGTH: 4771
<212> TYPE: DNA
<213> ORGANISM: homo sapiens

<400> SEQUENCE: 27

```
atgtgggctc agctccttct aggaatgttg gccctatcac cagccattgc agaagaactt      60
ccaaactacc tggtgacatt accagcccgg ctaaatttcc cctccgttca gaaggtttgt     120
ttggacctga gccctgggta cagtgatgtt aaattcacgg ttactctgga gaccaaggac     180
aagacccaga agttgctaga atactctgga ctgaagaaga ggcacttaca ttgtatctcc     240
tttcttgtac cacctcctgc tggtggcaca gaagaagtgg ccacaatccg ggtgtcggga     300
gttggaaata acatcagctt tgaggagaag aaaaaggttc taattcagag gcaggggaac     360
ggcacctttg tacagactga caaacctctc tacaccccag gcagcaagt gtatttccgc      420
attgtcacca tggatagcaa cttcgttcca gtgaatgaca agtactccat ggtggaacta     480
caggatccaa atagcaacag gattgcacag tggctgaaa tggtacctga gcaaggcatt      540
gtagacctgt ccttccaact ggcaccagag gcaatgctgg gcacctacac tgtggcagtg     600
gctgagggca agacctttgg tactttcagt gtggaggaat atgtgctttc tccatttctc     660
cttttactct cttcagtgct gccgaagttt aaggtggaag tggtggaacc caaggagtta     720
tcaacggtgc aggaatcttt cttagtaaag gggggttgt aggtacacct atggaaagcc      780
catgctaggg gcagtgcagg tatctgtgtg tcagaaggca atacttact ggtatcgaga      840
ggtgaacgg gaacagcttc ctgacaaatg caggaacctc tctggacaga ctgacaaaac      900
aggatgtttc tcagcacctg tggacatggc cacctttgac ctcattggat atgcgtacag     960
ccatcaaatc aatattgtgg ctactgttgt ggaggaaggg acaggtgtgg aggccaatgc    1020
cactcaaaat atctacattt ctccacaaat gggatcaatg acctttgaag acaccagcaa    1080
tttttaccat ccaaatttcc ccttcagtgg aagataaaa gatagggcc atgatgactc      1140
ctttctcaag aaccatttaa tggttctggg gatttaaggc acaaaatgaa cctttcacca    1200
gaccccctggt taactgaaaa caaatgcgct atgcttcctc tacctttgga gaatccccg     1260
gtggaaaggg acagaacgtt ctctggaggg aaagttttca ataggaaaac ttattatata    1320
atccggaaca aagggccacc gttactacca aaaaggccta acctgggcct gcgaacccttt   1380
ttacaagaac aaacccggaa cttttccttttg gcattccccc ggcttaaacg gcccttgaa   1440
atgtagccag ccccacgaag agctggtgga attattacat tcgacccggg ccatgcaagc    1500
ccctgaccca agagatcaac cttcttctac tattttaaat agggaaagga agtttggtga    1560
tggaggggca caaacacctg acctctaaga agaaaggact gaaagcctcc ttctctctct    1620
cactgaccctt cacttcgaga ctggcccctg atccttccct ggtgatctat gccattttttc   1680
ccagtggagg tgttgtagct gacaaaattc agttctcagt cgagatgtgc tttgacaatc    1740
aggtttccct tggcttctcc ccctcccagc agcttccagg agcagaagtg gagctgcagc    1800
tgcaggcagc tcccggatcc ctgtgtgcgc tccgggcggt ggatgagagt gtcttactgc    1860
ttaggccaga cagagagctg agcaaccgct ctgtctatgg gatgtttcca ttctggtatg    1920
gtcactaccc ctatcaagtg gctgagtatg atcagtgtcc agtgtctggc ccatgggact    1980
ttcctcagcc cctcattgac ccaatgcccc aagggcattc gagccagcgt tccattatct    2040
ggaggccctc gttctctgaa ggcacggacc ttttcagctt tttccgggac gtgggcctga    2100
aaatacatgt ccaatgccaa atcaagaag ccagtagatt gcagtcacag atctccagaa     2160
tacagcactg ctatgggtgc aggcggtggt catccagagg cttttgagtc atcaactcct    2220
```

```
ttacatcaag cagaggattc tcaggtccgc cagtacttcc cagagacctg gctctgggat    2280
ctgtttccta ttggtaactc ggggaaggag gcggtccacg tcacagtttc ctgacgccat    2340
caccgagtgg aaggcgatga gtttctgcac ttcccagtca agaggcttcg ggctttcacc    2400
cactgttgga ctaactgctt tcaagccgtt ctttgttgac ctgactcttc tcttactcag    2460
tagtccgtgg ggaatccttt cgtcttactg ccaccatctt caattaccta aaggattgca    2520
tcagggttca gactgacctg gctaaatcgc atgagtacca gctagaatca tgggcagatt    2580
ctcagacctc cagttgtctc tgtgctgatg aagcaaaaac ccaccactgg aacatcacag    2640
ctgtcaaatt gggtcacatt aactttacta ttagtacaaa gattccggac agcaatgaac    2700
catgtggggg ccagaagggg tttgttcccc aaaagggccg aagtgacacg ctcatcaagc    2760
cagttctcgt caaacctgag ggagtcctgg tggagaagac acacagctca ttgctgtgcc    2820
caaaaggaaa ggtggcatct gaatctgtct ccctggagct cccagtggac attgttcctg    2880
actcgaccaa ggcttatgtt acggttctgg agacattat gggcacagct ctgcagaacc     2940
tggatggtct ggtgcagatg cccagtggcc gtggcgagca gaacatggtc ttgtttgctc    3000
ccatcatcta tgtcttgcag tacctggaga aggcagggct gctgacggag gagatcaggt    3060
ctcgggcagt gggtttcctg gaaatagggt accagaagga gctgatgtac aaacacagca    3120
atggctcata cagtgccttt ggggagcgag atggaaatgg aaacacatgg ctgacagcgt    3180
tgtcacaaa atgctttggc caagctcaga aattcatctt cattgatccc aagaacatcc     3240
aggatgctct caagtggatg gcaggaaacc agctccccag tggctgctat gccaacgtgg    3300
gaaatctcct tcacacagct atgaaggtg ggtgttgatg atgaggtctc ctggactgcg     3360
tatgtcacag ctgcattgct ggagatggga aggatgtag atgacccaat ggtgagtcag     3420
ggtctatggt gtctcaagaa ttcggccacc tccacgacca acctctacac acaggccctg    3480
ttggcttaca ttttctcccct ggctggggaa atggacatca gaaacattct ccttaaacag   3540
ttagatcaac aggctatcat ctcaggagaa tccatttact ggagccagaa acctactcca    3600
tcatcgaacg ccagcccttg gtctgagcct gcggctgtag atgtggaact cacagcatat    3660
gcattgttgg cccagcttac caagcccagc ctgactcaaa aggagatagc gaaggccact    3720
agcatagtgc cttggttggc caagcaacac aatgcatatg ggggcttctc ttctactcag    3780
gatactgtag ttgctctcca agctcttgcc aaatatgcca ctaccgccta catgccatct    3840
gaggagatca acctggttgt aaaatccact gagaatttcc agcgcacatt caacatacag    3900
tcagttaaca gattggtatt tcagcaggat accctgccca atgtccctgg aatgtacacg    3960
ttggaggcct caggccaggg ctgtgtctat gtgcagacgg tgttgagata caatattctc    4020
cctcccataa atatgaagac ctttagtctt agtgtggaaa gaggaaaagc tagatgtgag    4080
cagccgactt cacctcgatc cttgactctc actattcgga gccaggtatg tggggagccg    4140
tagctcttgc aatatggcta ttgtggaagt gaagatgcta tctgggttca gtcccatgga    4200
gggcaccaat cagttacttc tccagcaacc cctggtgaag aaggttgaat ttggaacttg    4260
acaccactta aacatttact ttggatgaaa gctcattaag aacactcaga cttacacctt    4320
caccattagc caaagtgtgc tggtcaccaa cttgaaacca gcaaccatca aggtctatga    4380
ctactaccta ccagatgaac aggcaacaat tcagtattct gatccctgtg aatgaggata    4440
ggagctggaa actcaattag tcctctgtga catttactgg agggtggaac attcttctgt    4500
cgcttgaagc agaactcatt caatcaaata atttaatttc tctgactact atatgggtaa    4560
```

-continued

```
caaatgaata tgtctgaacc tcagctataa tactttctac tacctttgca aggagatggg      4620
ataggaacaa tcactcatag gaggcgttgc atggacaggg tcataggggg aagaaaggtg      4680
gtttatctgt tttatttagc catttcaggg ggctcttcac aagaggagac ggtggtagag      4740
ggtgaactag agaagataag aatgtcttcc t                                      4771

<210> SEQ ID NO 28
<211> LENGTH: 3405
<212> TYPE: DNA
<213> ORGANISM: homosapiens
<220> FEATURE:
<221> NAME/KEY: CDS
<222> LOCATION: (90)..(2828)

<400> SEQUENCE: 28
aatcccctta ctataggctc gagcgccccc ggcagattgg tttttatttgc tgttacacaa     60 acaacactac ataaaacatt ttttgctaa atg ata gtt tat aaa ttt gta cct       113
                                 Met Ile Val Tyr Lys Phe Val Pro
                                  1               5 gtc tca ccc aca aag atg tgg gct cag ctc ctt cta gga atg ttg gcc       161
Val Ser Pro Thr Lys Met Trp Ala Gln Leu Leu Leu Gly Met Leu Ala
 10              15                  20 cta tca cca gcc att gca gaa gaa ctt cca aac tac ctg gtg aca tta       209
Leu Ser Pro Ala Ile Ala Glu Glu Leu Pro Asn Tyr Leu Val Thr Leu
 25                  30                  35                  40 cca gcc cgg cta aat ttc ccc tcc gtt cag aag gtt tgt ttg gac ctg       257
Pro Ala Arg Leu Asn Phe Pro Ser Val Gln Lys Val Cys Leu Asp Leu
                 45                  50                  55 agc cct ggg tac agt gat gtt aaa ttc acg gtt act ctg gag acc aag       305
Ser Pro Gly Tyr Ser Asp Val Lys Phe Thr Val Thr Leu Glu Thr Lys
             60                  65                  70 gac aag acc cag aag ttg cta gaa tac tct gga ctg aag aag agg cac       353
Asp Lys Thr Gln Lys Leu Leu Glu Tyr Ser Gly Leu Lys Lys Arg His
         75                  80                  85 tta cat tgt atc tcc ttt ctt gta cca cct cct gct ggt ggc aca gaa       401
Leu His Cys Ile Ser Phe Leu Val Pro Pro Pro Ala Gly Gly Thr Glu
     90                  95                 100 gaa gtg gcc aca atc cgg gtg tcg gga gtt gga aat aac atc agc ttt       449
Glu Val Ala Thr Ile Arg Val Ser Gly Val Gly Asn Asn Ile Ser Phe
105                 110                 115                 120 gag gag aag aaa aag gtt cta att cag agg cag ggg aac ggc acc ttt       497
Glu Glu Lys Lys Lys Val Leu Ile Gln Arg Gln Gly Asn Gly Thr Phe
                125                 130                 135 gta cag act gac aaa cct ctc tac acc cca ggg cag caa gtg tat ttc       545
Val Gln Thr Asp Lys Pro Leu Tyr Thr Pro Gly Gln Gln Val Tyr Phe
            140                 145                 150 cgc att gtc acc atg gat agc aac ttc gtt cca gtg aat gac aag tac       593
Arg Ile Val Thr Met Asp Ser Asn Phe Val Pro Val Asn Asp Lys Tyr
        155                 160                 165 tcc atg gtg gaa cta cag gat cca aat agc aac agg att gca cag tgg       641
Ser Met Val Glu Leu Gln Asp Pro Asn Ser Asn Arg Ile Ala Gln Trp
    170                 175                 180 ctg gaa gtg gta cct gag caa ggc att gta gac ctg tcc ttc caa ctg       689
Leu Glu Val Val Pro Glu Gln Gly Ile Val Asp Leu Ser Phe Gln Leu
185                 190                 195                 200 gca cca gag gca atg ctg ggc acc tac act gtg gca gtg gct gag ggc       737
Ala Pro Glu Ala Met Leu Gly Thr Tyr Thr Val Ala Val Ala Glu Gly
                205                 210                 215 aag acc ttt ggt act ttc agt gtg gag gaa tat gtg ctg ccg aag ttt       785
Lys Thr Phe Gly Thr Phe Ser Val Glu Glu Tyr Val Leu Pro Lys Phe
```

-continued

```
                 220                 225                 230
aag gtg gaa gtg gtg gaa ccc aag gag tta tca acg gtg cag gaa tct      833
Lys Val Glu Val Val Glu Pro Lys Glu Leu Ser Thr Val Gln Glu Ser
            235                 240                 245 ttc tta gta aaa att tgt tgt agg tac acc tat gga aag ccc atg cta      881
Phe Leu Val Lys Ile Cys Cys Arg Tyr Thr Tyr Gly Lys Pro Met Leu
    250                 255                 260 ggg gca gtg cag gta tct gtg tgt cag aag gca aat act tac tgg tat      929
Gly Ala Val Gln Val Ser Val Cys Gln Lys Ala Asn Thr Tyr Trp Tyr
265                 270                 275                 280 cga gag gtg gaa cgg gaa cag ctt cct gac aaa tgc agg aac ctc tct      977
Arg Glu Val Glu Arg Glu Gln Leu Pro Asp Lys Cys Arg Asn Leu Ser
                285                 290                 295 gga cag act gac aaa aca gga tgt ttc tca gca cct gtg gac atg gcc     1025
Gly Gln Thr Asp Lys Thr Gly Cys Phe Ser Ala Pro Val Asp Met Ala
            300                 305                 310 acc ttt gac ctc att gga tat gcg tac agc cat caa atc aat att gtg     1073
Thr Phe Asp Leu Ile Gly Tyr Ala Tyr Ser His Gln Ile Asn Ile Val
    315                 320                 325 gct act gtt gtg gag gaa ggg aca ggt gtg gag gcc aat gcc act cag     1121
Ala Thr Val Val Glu Glu Gly Thr Gly Val Glu Ala Asn Ala Thr Gln
330                 335                 340 aat atc tac att tct cca caa atg gga tca atg acc ttt gaa gac acc     1169
Asn Ile Tyr Ile Ser Pro Gln Met Gly Ser Met Thr Phe Glu Asp Thr
345                 350                 355                 360 agc aat ttt tac cat cca aat ttc ccc ttc agt ggg aag ata aga gtt     1217
Ser Asn Phe Tyr His Pro Asn Phe Pro Phe Ser Gly Lys Ile Arg Val
                365                 370                 375 agg ggc cat gat gac tcc ttc ctc aag aac cat cta gtg ttt ctg gtg     1265
Arg Gly His Asp Asp Ser Phe Leu Lys Asn His Leu Val Phe Leu Val
            380                 385                 390 att tat ggc aca aat gga acc ttc aac cag acc ctg gtt act gat aac     1313
Ile Tyr Gly Thr Asn Gly Thr Phe Asn Gln Thr Leu Val Thr Asp Asn
    395                 400                 405 aat ggc cta gct ccc ttt acc ttg gag aca tcc ggt tgg aat ggg aca     1361
Asn Gly Leu Ala Pro Phe Thr Leu Glu Thr Ser Gly Trp Asn Gly Thr
410                 415                 420 gac gtt tct ctg gag gga aag ttt caa atg gaa gac tta gta tat aat     1409
Asp Val Ser Leu Glu Gly Lys Phe Gln Met Glu Asp Leu Val Tyr Asn
425                 430                 435                 440 ccg gaa caa gtg cca cgt tac tac caa aat gcc tac ctg cac ctg cga     1457
Pro Glu Gln Val Pro Arg Tyr Tyr Gln Asn Ala Tyr Leu His Leu Arg
                445                 450                 455 ccc ttc tac agc aca acc cgc agc ttc ctt ggc atc cac cgg cta aac     1505
Pro Phe Tyr Ser Thr Thr Arg Ser Phe Leu Gly Ile His Arg Leu Asn
            460                 465                 470 ggc ccc ttg aaa tgt ggc cag ccc cag gaa gtg ctg gtg gat tat tac     1553
Gly Pro Leu Lys Cys Gly Gln Pro Gln Glu Val Leu Val Asp Tyr Tyr
    475                 480                 485 atc gac ccg gcc gat gca agc cct gac caa gag atc agc ttc tcc tac     1601
Ile Asp Pro Ala Asp Ala Ser Pro Asp Gln Glu Ile Ser Phe Ser Tyr
490                 495                 500 tat tta ata ggg aaa gga agt ttg gtg atg gag ggg cag aaa cac ctg     1649
Tyr Leu Ile Gly Lys Gly Ser Leu Val Met Glu Gly Gln Lys His Leu
505                 510                 515                 520 aac tct aag aag aaa gga ctg aaa gcc tcc ttc tct ctc tca ctg acc     1697
Asn Ser Lys Lys Lys Gly Leu Lys Ala Ser Phe Ser Leu Ser Leu Thr
                525                 530                 535 ttc act tcg aga ctg gcc cct gat cct tcc ctg gtg atc tat gcc att     1745
```

```
                Phe Thr Ser Arg Leu Ala Pro Asp Pro Ser Leu Val Ile Tyr Ala Ile
                        540                 545                 550 ttt ccc agt gga ggt gtt gta gct gac aaa att cag ttc tca gtc gag       1793
Phe Pro Ser Gly Gly Val Val Ala Asp Lys Ile Gln Phe Ser Val Glu
            555                 560                 565 atg tgc ttt gac aat cag gtt tcc ctt ggc ttc tcc ccc tcc cag cag       1841
Met Cys Phe Asp Asn Gln Val Ser Leu Gly Phe Ser Pro Ser Gln Gln
570                 575                 580 ctt cca gga gca gaa gtg gag ctg cag ctg cag gca gct ccc gga tcc       1889
Leu Pro Gly Ala Glu Val Glu Leu Gln Leu Gln Ala Ala Pro Gly Ser
585                 590                 595                 600 ctg tgt gcg ctc cgg gcg gtg gat gag agt gtc tta ctg ctt agg cca       1937
Leu Cys Ala Leu Arg Ala Val Asp Glu Ser Val Leu Leu Leu Arg Pro
                605                 610                 615 gac aga gag ctg agc aac cgc tct gtc tat ggg atg ttt cca ttc tgg       1985
Asp Arg Glu Leu Ser Asn Arg Ser Val Tyr Gly Met Phe Pro Phe Trp
            620                 625                 630 tat ggt cac tac ccc tat caa gtg gct gag tat gat cag tgt cca gtg       2033
Tyr Gly His Tyr Pro Tyr Gln Val Ala Glu Tyr Asp Gln Cys Pro Val
                635                 640                 645 tct ggc cca tgg gac ttt cct cag ccc ctc att gac cca atg ccc caa       2081
Ser Gly Pro Trp Asp Phe Pro Gln Pro Leu Ile Asp Pro Met Pro Gln
650                 655                 660 ggg cat tcg agc cag cgt tcc att atc tgg agg ccc tcg ttc tct gaa       2129
Gly His Ser Ser Gln Arg Ser Ile Ile Trp Arg Pro Ser Phe Ser Glu
665                 670                 675                 680 ggc acg gac ctt ttc agc ttt ttc cgg gac gtg ggc ctg aaa ata ctg       2177
Gly Thr Asp Leu Phe Ser Phe Phe Arg Asp Val Gly Leu Lys Ile Leu
                685                 690                 695 tcc aat gcc aaa atc aag aag cca gta gat tgc agt cac aga tct cca       2225
Ser Asn Ala Lys Ile Lys Lys Pro Val Asp Cys Ser His Arg Ser Pro
            700                 705                 710 gaa tac agc act gct atg ggt gca ggc ggt ggt cat cca gag gct ttt       2273
Glu Tyr Ser Thr Ala Met Gly Ala Gly Gly Gly His Pro Glu Ala Phe
            715                 720                 725 gag tca tca act cct tta cat caa gca gag gat tct cag gtc cgc cag       2321
Glu Ser Ser Thr Pro Leu His Gln Ala Glu Asp Ser Gln Val Arg Gln
            730                 735                 740 tac ttc cca gag acc tgg ctc tgg gat ctg ttt cct att ggt aac tcg       2369
Tyr Phe Pro Glu Thr Trp Leu Trp Asp Leu Phe Pro Ile Gly Asn Ser
745                 750                 755                 760 ggg aag gag gcg gtc cac gtc aca gtt cct gac gcc atc acc gag tgg       2417
Gly Lys Glu Ala Val His Val Thr Val Pro Asp Ala Ile Thr Glu Trp
                765                 770                 775 aag gcg atg agt ttc tgc act tcc cag tca aga ggc ttc ggg ctt tca       2465
Lys Ala Met Ser Phe Cys Thr Ser Gln Ser Arg Gly Phe Gly Leu Ser
            780                 785                 790 ccc act gtt gga cta act gct ttc aag cca ttc ttt gtt gac ctg act       2513
Pro Thr Val Gly Leu Thr Ala Phe Lys Pro Phe Phe Val Asp Leu Thr
        795                 800                 805 ctc cct tac tca gta gtc cgt ggg gaa tcc ttt cgt ctt act gcc acc       2561
Leu Pro Tyr Ser Val Val Arg Gly Glu Ser Phe Arg Leu Thr Ala Thr
            810                 815                 820 atc ttc aat tac cta aag gat tgc atc agg gtg aga gct ggg ata aca       2609
Ile Phe Asn Tyr Leu Lys Asp Cys Ile Arg Val Arg Ala Gly Asp Thr
825                 830                 835                 840 gga atc agg tgt cag ccc tgg aat cac acc tcc ccc ata act ttg tct       2657
Gly Ile Arg Cys Gln Pro Trp Asn His Thr Ser Pro Ile Thr Leu Ser
            845                 850                 855 cta aat tgg aag cat ccc aat ttt ccc tgg gaa aga gag gag atg tcg       2705
```

-continued

```
Leu Asn Trp Lys His Pro Asn Phe Pro Trp Glu Arg Glu Glu Met Ser
            860                 865                 870 gcg tct cag ccc cca ggt ttc ccc agg cct cta tgc act acc tcc ttt        2753
Ala Ser Gln Pro Pro Gly Phe Pro Arg Pro Leu Cys Thr Thr Ser Phe
            875                 880                 885 gtt tgt acc ctt tgt ctc tta aac atc ctc cgt agg ttc aga ctg acc        2801
Val Cys Thr Leu Cys Leu Leu Asn Ile Leu Arg Arg Phe Arg Leu Thr
            890                 895                 900 tgg cta aat cgc atg agt acc agc tag aatcatgggc agattctcag              2848
Trp Leu Asn Arg Met Ser Thr Ser
905             910 acctccagtt gtctctgtgc tgatgaagca aaaacccacc actggaacat cacagctgtc      2908
aaattgggta agagagggaa gtggtagacg ggcgaggaaa gccagcagca aaagaccagt      2968
gactgagcac tcagtctttt cctctgccac atctgctttg cttcctcctc catttccac       3028 tattttctc cctcctaagg ctgttataag tcaatacaca aacactcttt gataggtgac       3088
caaacaaatt tgttcaaacc ggaatatttt gagtgtgaaa gggagagctt ttaatattta     3148
tagctggaca aggaatacat ggtcatgtaa ctaatcaagg acttactata agagtccctg     3208
ggccaggcac tattctaact gctttacata tattaactca ttaaattgat tgactaatta     3268 attttattt tatttattta tttttgagag gagaatcgct tgaacctggg aggtggaggt      3328
tgcagtgggc tgagatcacg ccattgcact ccagcctggg cgacagagtg agactctgtc     3388 tcaaaaaaa aaaaaaa                                                     3405

<210> SEQ ID NO 29
<211> LENGTH: 912
<212> TYPE: PRT
<213> ORGANISM: homosapiens

<400> SEQUENCE: 29

Met Ile Val Tyr Lys Phe Val Pro Val Ser Pro Thr Lys Met Trp Ala
1               5                   10                  15

Gln Leu Leu Leu Gly Met Leu Ala Leu Ser Pro Ala Ile Ala Glu Glu
            20                  25                  30

Leu Pro Asn Tyr Leu Val Thr Leu Pro Ala Arg Leu Asn Phe Pro Ser
            35                  40                  45

Val Gln Lys Val Cys Leu Asp Leu Ser Pro Gly Tyr Ser Asp Val Lys
        50                  55                  60

Phe Thr Val Thr Leu Glu Thr Lys Asp Lys Thr Gln Lys Leu Leu Glu
65              70                  75                  80

Tyr Ser Gly Leu Lys Lys Arg His Leu His Cys Ile Ser Phe Leu Val
                85                  90                  95

Pro Pro Pro Ala Gly Gly Thr Glu Glu Val Ala Thr Ile Arg Val Ser
            100                 105                 110

Gly Val Gly Asn Asn Ile Ser Phe Glu Glu Lys Lys Val Leu Ile
            115                 120                 125

Gln Arg Gln Gly Asn Gly Thr Phe Val Gln Thr Asp Lys Pro Leu Tyr
        130                 135                 140

Thr Pro Gly Gln Gln Val Tyr Phe Arg Ile Val Thr Met Asp Ser Asn
145                 150                 155                 160

Phe Val Pro Val Asn Asp Lys Tyr Ser Met Val Glu Leu Gln Asp Pro
                165                 170                 175

Asn Ser Asn Arg Ile Ala Gln Trp Leu Glu Val Pro Glu Gln Gly
            180                 185                 190
```

```
Ile Val Asp Leu Ser Phe Gln Leu Ala Pro Glu Ala Met Leu Gly Thr
            195                 200                 205

Tyr Thr Val Ala Val Ala Glu Gly Lys Thr Phe Gly Thr Phe Ser Val
        210                 215                 220

Glu Glu Tyr Val Leu Pro Lys Phe Lys Val Glu Val Val Glu Pro Lys
225                 230                 235                 240

Glu Leu Ser Thr Val Gln Glu Ser Phe Leu Val Lys Ile Cys Cys Arg
                245                 250                 255

Tyr Thr Tyr Gly Lys Pro Met Leu Gly Ala Val Gln Val Ser Val Cys
            260                 265                 270

Gln Lys Ala Asn Thr Tyr Trp Tyr Arg Glu Val Glu Arg Glu Gln Leu
        275                 280                 285

Pro Asp Lys Cys Arg Asn Leu Ser Gly Gln Thr Asp Lys Thr Gly Cys
290                 295                 300

Phe Ser Ala Pro Val Asp Met Ala Thr Phe Asp Leu Ile Gly Tyr Ala
305                 310                 315                 320

Tyr Ser His Gln Ile Asn Ile Val Ala Thr Val Val Glu Glu Gly Thr
                325                 330                 335

Gly Val Glu Ala Asn Ala Thr Gln Asn Ile Tyr Ile Ser Pro Gln Met
            340                 345                 350

Gly Ser Met Thr Phe Glu Asp Thr Ser Asn Phe Tyr His Pro Asn Phe
        355                 360                 365

Pro Phe Ser Gly Lys Ile Arg Val Arg Gly His Asp Asp Ser Phe Leu
        370                 375                 380

Lys Asn His Leu Val Phe Leu Val Ile Tyr Gly Thr Asn Gly Thr Phe
385                 390                 395                 400

Asn Gln Thr Leu Val Thr Asp Asn Asn Gly Leu Ala Pro Phe Thr Leu
                405                 410                 415

Glu Thr Ser Gly Trp Asn Gly Thr Asp Val Ser Leu Glu Gly Lys Phe
            420                 425                 430

Gln Met Glu Asp Leu Val Tyr Asn Pro Glu Gln Val Pro Arg Tyr Tyr
        435                 440                 445

Gln Asn Ala Tyr Leu His Leu Arg Pro Phe Tyr Ser Thr Thr Arg Ser
450                 455                 460

Phe Leu Gly Ile His Arg Leu Asn Gly Pro Leu Lys Cys Gly Gln Pro
465                 470                 475                 480

Gln Glu Val Leu Val Asp Tyr Tyr Ile Asp Pro Ala Asp Ala Ser Pro
                485                 490                 495

Asp Gln Glu Ile Ser Phe Ser Tyr Tyr Leu Ile Gly Lys Gly Ser Leu
            500                 505                 510

Val Met Glu Gly Gln Lys His Leu Asn Ser Lys Lys Gly Leu Lys
        515                 520                 525

Ala Ser Phe Ser Leu Ser Leu Thr Phe Thr Ser Arg Leu Ala Pro Asp
530                 535                 540

Pro Ser Leu Val Ile Tyr Ala Ile Phe Pro Ser Gly Gly Val Val Ala
545                 550                 555                 560

Asp Lys Ile Gln Phe Ser Val Glu Met Cys Phe Asp Asn Gln Val Ser
                565                 570                 575

Leu Gly Phe Ser Pro Ser Gln Gln Leu Pro Gly Ala Glu Val Glu Leu
            580                 585                 590

Gln Leu Gln Ala Ala Pro Gly Ser Leu Cys Ala Leu Arg Ala Val Asp
        595                 600                 605

Glu Ser Val Leu Leu Leu Arg Pro Asp Arg Glu Leu Ser Asn Arg Ser
```

```
                610             615             620
Val Tyr Gly Met Phe Pro Phe Trp Tyr Gly His Tyr Pro Tyr Gln Val
625             630                     635                 640

Ala Glu Tyr Asp Gln Cys Pro Val Ser Gly Pro Trp Asp Phe Pro Gln
                645                 650                 655

Pro Leu Ile Asp Pro Met Pro Gln Gly His Ser Ser Gln Arg Ser Ile
            660                 665                 670

Ile Trp Arg Pro Ser Phe Ser Glu Gly Thr Asp Leu Phe Ser Phe Phe
        675                 680                 685

Arg Asp Val Gly Leu Lys Ile Leu Ser Asn Ala Lys Ile Lys Lys Pro
690                 695                 700

Val Asp Cys Ser His Arg Ser Pro Glu Tyr Ser Thr Ala Met Gly Ala
705             710                 715                 720

Gly Gly Gly His Pro Glu Ala Phe Glu Ser Ser Thr Pro Leu His Gln
                725                 730                 735

Ala Glu Asp Ser Gln Val Arg Gln Tyr Phe Pro Glu Thr Trp Leu Trp
            740                 745                 750

Asp Leu Phe Pro Ile Gly Asn Ser Gly Lys Glu Ala Val His Val Thr
        755                 760                 765

Val Pro Asp Ala Ile Thr Glu Trp Lys Ala Met Ser Phe Cys Thr Ser
770                 775                 780

Gln Ser Arg Gly Phe Gly Leu Ser Pro Thr Val Gly Leu Thr Ala Phe
785             790                 795                 800

Lys Pro Phe Phe Val Asp Leu Thr Leu Pro Tyr Ser Val Val Arg Gly
                805                 810                 815

Glu Ser Phe Arg Leu Thr Ala Thr Ile Phe Asn Tyr Leu Lys Asp Cys
            820                 825                 830

Ile Arg Val Arg Ala Gly Asp Thr Gly Ile Arg Cys Gln Pro Trp Asn
        835                 840                 845

His Thr Ser Pro Ile Thr Leu Ser Leu Asn Trp Lys His Pro Asn Phe
850                 855                 860

Pro Trp Glu Arg Glu Glu Met Ser Ala Ser Gln Pro Pro Gly Phe Pro
865             870                 875                 880

Arg Pro Leu Cys Thr Thr Ser Phe Val Cys Thr Leu Cys Leu Leu Asn
                885                 890                 895

Ile Leu Arg Arg Phe Arg Leu Thr Trp Leu Asn Arg Met Ser Thr Ser
            900                 905                 910
```

<210> SEQ ID NO 30
<211> LENGTH: 2739
<212> TYPE: DNA
<213> ORGANISM: homo sapiens

<400> SEQUENCE: 30

```
atgatagttt ataaatttgt acctgtctca cccacaaaga tgtgggctca gctccttcta    60
ggaatgttgg ccctatcacc agccattgca gaagaacttc aaactacct ggtgacatta    120
ccagcccggc taaatttccc ctccgttcag aaggttttgt tggacctgag ccctgggtac    180
agtgatgtta aattcacggt tactctggag accaaggaca agacccagaa gttgctagaa    240
tactctggac tgaagaagag gcacttacat tgtatctcct tcttgtacc acctcctgct    300
ggtggcacag aagaagtggc cacaatccgg gtgtcgggag ttggaaataa catcagcttt    360
gaggagaaga aaaaggttct aattcagagg caggggaacg cacctttgt acagactgac    420
aaacctctct acacccccagg gcagcaagtg tatttccgca ttgtcaccat ggatagcaac    480
```

-continued

```
ttcgttccag tgaatgacaa gtactccatg gtggaactac aggatccaaa tagcaacagg      540
attgcacagt ggctggaagt ggtacctgag caaggcattg tagacctgtc cttccaactg      600
gcaccagagg caatgctggg cacctacact gtggcagtgg ctgagggcaa gacctttggt      660
actttcagtg tggaggaata tgtgctgccg aagtttaagg tggaagtggt ggaacccaag      720
gagttatcaa cggtgcagga atctttctta gtaaaaattt gttgtaggta cacctatgga      780
aagcccatgc taggggcagt gcaggtatct gtgtgtcaga aggcaaatac ttactggtat      840
cgagaggtgg aacggaaca gcttcctgac aaatgcagga acctctctgg acagactgac       900
aaaacaggat gtttctcagc acctgtggac atggccacct ttgacctcat tggatatgcg      960
tacagccatc aaatcaatat tgtggctact gttgtggagg aagggacagg tgtgaggcc     1020 aatgccactc agaatatcta catttctcca caaatgggat caatgacctt tgaagacacc     1080 agcaatttt accatccaaa tttccccttc agtgggaaga taagagttag ggccatgat      1140 gactccttcc tcaagaacca tctagtgttt ctggtgattt atggcacaaa tggaaccttc     1200
aaccagaccc tggttactga taacaatggc ctagctccct ttaccttgga catccggt       1260 tggaatggga cagacgtttc tctggaggga aagtttcaaa tggaagactt agtatataat     1320
ccggaacaag tgccacgtta ctaccaaaaat gcctacctgc acctgcgacc cttctacagc    1380
acaacccgca gcttccttgg catccaccgg ctaaacggcc ccttgaaatg tggccagccc     1440
caggaagtgc tggtggatta ttacatcgac ccggccgatg caagccctga ccaagagatc     1500
agcttctcct actatttaat agggaaagga agtttggtga tggagggca gaaacacctg      1560 aactctaaga gaaaggact gaaagcctcc ttctctctct cactgacctt cacttcgaga      1620
ctggcccctg atccttccct ggtgatctat gccatttttc ccagtggagg tgttgtagct     1680
gacaaaattc agttctcagt cgagatgtgc tttgacaatc aggtttccct tggcttctcc     1740
ccctcccagc agcttccagg agcagaagtg gagctgcagc tgcaggcagc tcccggatcc     1800
ctgtgtgcgc tccgggcggt ggatgagagt gtcttactgc ttaggccaga cagagagctg     1860
agcaaccgct ctgtctatgg gatgtttcca ttctggtatg gtcactaccc ctatcaagtg     1920
gctgagtatg atcagtgtcc agtgtctggc ccatgggact ttcctcagcc cctcattgac     1980
ccaatgcccc aagggcattc gagccagcgt tccattatct ggaggccctc gttctctgaa     2040
ggcacggacc ttttcagctt tttccgggac gtgggcctga aaatactgtc caatgccaaa     2100
atcaagaagc cagtagattg cagtcacaga tctccagaat acagcactgc tatgggtgca     2160
ggcggtggtc atccagaggc ttttgagtca tcaactcctt tacatcaagc agaggattct     2220
caggtccgcc agtacttccc agagacctgg ctctgggatc tgtttcctat tggtaactcg     2280
gggaaggagg cggtccacgt cacagttcct gacgccatca ccgagtggaa ggcgatgagt     2340
ttctgcactt cccagtcaag aggcttcggg ctttcaccca ctgttggact aactgctttc     2400
aagccattct tgttgacct gactctccct tactcagtag tccgtgggga atcctttcgt      2460
cttactgcca ccatcttcaa ttacctaaag gattgcatca gggtgagagc tggggataca     2520
ggaatcaggt gtcagccctg gaatcacacc tcccccataa ctttgtctct aaattggaag     2580
catcccaatt ttccctggga aagagaggag atgtcggcgt ctcagccccc aggtttcccc     2640
aggcctctat gcactacctc ctttgtttgt acccctttgtc tcttaaacat cctccgtagg    2700
ttcagactga cctggctaaa tcgcatgagt accagctag                            2739
```

<210> SEQ ID NO 31

```
<211> LENGTH: 30
<212> TYPE: PRT
<213> ORGANISM: homo sapiens

<400> SEQUENCE: 31

Ala Phe Lys Pro Phe Val Asp Leu Thr Leu Pro Tyr Ser Val Val
1               5                   10                  15

Arg Gly Glu Ser Phe Arg Leu Thr Ala Thr Ile Phe Asn Tyr
            20                  25                  30

<210> SEQ ID NO 32
<211> LENGTH: 29
<212> TYPE: PRT
<213> ORGANISM: homo sapiens

<400> SEQUENCE: 32

Thr Phe Val Gln Thr Asp Lys Pro Leu Tyr Thr Pro Gly Gln Val
1               5                   10                  15

Tyr Phe Arg Ile Val Thr Met Asp Ser Asn Phe Val Pro
            20                  25

<210> SEQ ID NO 33
<211> LENGTH: 27
<212> TYPE: PRT
<213> ORGANISM: homo sapiens

<400> SEQUENCE: 33

Phe Val Asp Leu Thr Leu Pro Tyr Ser Val Val Arg Gly Glu Ser Phe
1               5                   10                  15

Arg Leu Thr Ala Thr Ile Phe Asn Tyr Leu Lys
            20                  25

<210> SEQ ID NO 34
<211> LENGTH: 21
<212> TYPE: PRT
<213> ORGANISM: homo sapiens

<400> SEQUENCE: 34

Val Pro Asp Ala Ile Thr Glu Trp Lys Ala Met Ser Phe Cys Thr Ser
1               5                   10                  15

Gln Ser Arg Gly Phe
            20

<210> SEQ ID NO 35
<211> LENGTH: 13
<212> TYPE: PRT
<213> ORGANISM: homo sapiens

<400> SEQUENCE: 35

Phe Ser Val Glu Glu Tyr Val Leu Pro Lys Phe Lys Val
1               5                   10

<210> SEQ ID NO 36
<211> LENGTH: 10
<212> TYPE: PRT
<213> ORGANISM: homo sapiens

<400> SEQUENCE: 36

Arg Gln Tyr Phe Pro Glu Thr Trp Leu Trp
1               5                   10

<210> SEQ ID NO 37
<211> LENGTH: 17
```

-continued

```
<212> TYPE: PRT
<213> ORGANISM: homo sapiens

<400> SEQUENCE: 37

Phe Leu Val Lys Ile Cys Cys Arg Tyr Thr Tyr Gly Lys Pro Met Leu
1               5                   10                  15

Gly

<210> SEQ ID NO 38
<211> LENGTH: 30
<212> TYPE: PRT
<213> ORGANISM: homo sapiens

<400> SEQUENCE: 38

Met Ile Val Tyr Lys Phe Val Pro Val Ser Pro Thr Lys Met Trp Ala
1               5                   10                  15

Gln Leu Leu Leu Gly Met Leu Ala Leu Ser Pro Ala Ile Ala
            20                  25                  30

<210> SEQ ID NO 39
<211> LENGTH: 882
<212> TYPE: PRT
<213> ORGANISM: homo sapiens

<400> SEQUENCE: 39

Glu Glu Leu Pro Asn Tyr Leu Val Thr Leu Pro Ala Arg Leu Asn Phe
1               5                   10                  15

Pro Ser Val Gln Lys Val Cys Leu Asp Leu Ser Pro Gly Tyr Ser Asp
            20                  25                  30

Val Lys Phe Thr Val Thr Leu Glu Thr Lys Asp Lys Thr Gln Lys Leu
        35                  40                  45

Leu Glu Tyr Ser Gly Leu Lys Lys Arg His Leu His Cys Ile Ser Phe
    50                  55                  60

Leu Val Pro Pro Ala Gly Gly Thr Glu Val Ala Thr Ile Arg
65                  70                  75                  80

Val Ser Gly Val Gly Asn Asn Ile Ser Phe Glu Glu Lys Lys Lys Val
                85                  90                  95

Leu Ile Gln Arg Gln Gly Asn Gly Thr Phe Val Gln Thr Asp Lys Pro
            100                 105                 110

Leu Tyr Thr Pro Gly Gln Gln Val Tyr Phe Arg Ile Val Thr Met Asp
        115                 120                 125

Ser Asn Phe Val Pro Val Asn Asp Lys Tyr Ser Met Val Glu Leu Gln
    130                 135                 140

Asp Pro Asn Ser Asn Arg Ile Ala Gln Trp Leu Glu Val Val Pro Glu
145                 150                 155                 160

Gln Gly Ile Val Asp Leu Ser Phe Gln Leu Ala Pro Glu Ala Met Leu
                165                 170                 175

Gly Thr Tyr Thr Val Ala Val Ala Glu Gly Lys Thr Phe Gly Thr Phe
            180                 185                 190

Ser Val Glu Glu Tyr Val Leu Pro Lys Phe Lys Val Glu Val Val Glu
        195                 200                 205

Pro Lys Glu Leu Ser Thr Val Gln Glu Ser Phe Leu Val Lys Ile Cys
    210                 215                 220

Cys Arg Tyr Thr Tyr Gly Lys Pro Met Leu Gly Ala Val Gln Val Ser
225                 230                 235                 240

Val Cys Gln Lys Ala Asn Thr Tyr Trp Tyr Arg Glu Val Glu Arg Glu
                245                 250                 255
```

-continued

```
Gln Leu Pro Asp Lys Cys Arg Asn Leu Ser Gly Gln Thr Asp Lys Thr
            260                 265                 270
Gly Cys Phe Ser Ala Pro Val Asp Met Ala Thr Phe Asp Leu Ile Gly
        275                 280                 285
Tyr Ala Tyr Ser His Gln Ile Asn Ile Val Ala Thr Val Val Glu Glu
    290                 295                 300
Gly Thr Gly Val Glu Ala Asn Ala Thr Gln Asn Ile Tyr Ile Ser Pro
305                 310                 315                 320
Gln Met Gly Ser Met Thr Phe Glu Asp Thr Ser Asn Phe Tyr His Pro
                325                 330                 335
Asn Phe Pro Phe Ser Gly Lys Ile Arg Val Arg Gly His Asp Asp Ser
            340                 345                 350
Phe Leu Lys Asn His Leu Val Phe Leu Val Ile Tyr Gly Thr Asn Gly
        355                 360                 365
Thr Phe Asn Gln Thr Leu Val Thr Asp Asn Asn Gly Leu Ala Pro Phe
    370                 375                 380
Thr Leu Glu Thr Ser Gly Trp Asn Gly Thr Asp Val Ser Leu Glu Gly
385                 390                 395                 400
Lys Phe Gln Met Glu Asp Leu Val Tyr Asn Pro Glu Gln Val Pro Arg
                405                 410                 415
Tyr Tyr Gln Asn Ala Tyr Leu His Leu Arg Pro Phe Tyr Ser Thr Thr
            420                 425                 430
Arg Ser Phe Leu Gly Ile His Arg Leu Asn Gly Pro Leu Lys Cys Gly
        435                 440                 445
Gln Pro Gln Glu Val Leu Val Asp Tyr Tyr Ile Asp Pro Ala Asp Ala
    450                 455                 460
Ser Pro Asp Gln Glu Ile Ser Phe Ser Tyr Tyr Leu Ile Gly Lys Gly
465                 470                 475                 480
Ser Leu Val Met Glu Gly Gln Lys His Leu Asn Ser Lys Lys Lys Gly
                485                 490                 495
Leu Lys Ala Ser Phe Ser Leu Ser Leu Thr Phe Thr Ser Arg Leu Ala
            500                 505                 510
Pro Asp Pro Ser Leu Val Ile Tyr Ala Ile Phe Pro Ser Gly Gly Val
        515                 520                 525
Val Ala Asp Lys Ile Gln Phe Ser Val Glu Met Cys Phe Asp Asn Gln
    530                 535                 540
Val Ser Leu Gly Phe Ser Pro Ser Gln Gln Leu Pro Gly Ala Glu Val
545                 550                 555                 560
Glu Leu Gln Leu Gln Ala Ala Pro Gly Ser Leu Cys Ala Leu Arg Ala
                565                 570                 575
Val Asp Glu Ser Val Leu Leu Leu Arg Pro Asp Arg Glu Leu Ser Asn
            580                 585                 590
Arg Ser Val Tyr Gly Met Phe Pro Phe Trp Tyr Gly His Tyr Pro Tyr
        595                 600                 605
Gln Val Ala Glu Tyr Asp Gln Cys Pro Val Ser Gly Pro Trp Asp Phe
    610                 615                 620
Pro Gln Pro Leu Ile Asp Pro Met Pro Gln Gly His Ser Ser Gln Arg
625                 630                 635                 640
Ser Ile Ile Trp Arg Pro Ser Phe Ser Glu Gly Thr Asp Leu Phe Ser
                645                 650                 655
Phe Phe Arg Asp Val Gly Leu Lys Ile Leu Ser Asn Ala Lys Ile Lys
            660                 665                 670
```

-continued

```
Lys Pro Val Asp Cys Ser His Arg Ser Pro Glu Tyr Ser Thr Ala Met
            675                 680                 685
Gly Ala Gly Gly His Pro Glu Ala Phe Glu Ser Ser Thr Pro Leu
        690                 695                 700
His Gln Ala Glu Asp Ser Gln Val Arg Gln Tyr Phe Pro Glu Thr Trp
705                 710                 715                 720
Leu Trp Asp Leu Phe Pro Ile Gly Asn Ser Gly Lys Glu Ala Val His
                725                 730                 735
Val Thr Val Pro Asp Ala Ile Thr Glu Trp Lys Ala Met Ser Phe Cys
            740                 745                 750
Thr Ser Gln Ser Arg Gly Phe Gly Leu Ser Pro Thr Val Gly Leu Thr
        755                 760                 765
Ala Phe Lys Pro Phe Phe Val Asp Leu Thr Leu Pro Tyr Ser Val Val
        770                 775                 780
Arg Gly Glu Ser Phe Arg Leu Thr Ala Thr Ile Phe Asn Tyr Leu Lys
785                 790                 795                 800
Asp Cys Ile Arg Val Arg Ala Gly Asp Thr Gly Ile Arg Cys Gln Pro
                805                 810                 815
Trp Asn His Thr Ser Pro Ile Thr Leu Ser Leu Asn Trp Lys His Pro
            820                 825                 830
Asn Phe Pro Trp Glu Arg Glu Glu Met Ser Ala Ser Gln Pro Pro Gly
        835                 840                 845
Phe Pro Arg Pro Leu Cys Thr Thr Ser Phe Val Cys Thr Leu Cys Leu
        850                 855                 860
Leu Asn Ile Leu Arg Arg Phe Arg Leu Thr Trp Leu Asn Arg Met Ser
865                 870                 875                 880
Thr Ser

<210> SEQ ID NO 40
<211> LENGTH: 36
<212> TYPE: PRT
<213> ORGANISM: homo sapiens

<400> SEQUENCE: 40

Ser Lys Thr Thr Phe Gly Phe Pro Gly Tyr Gln Lys Glu Leu Met Tyr
1               5                   10                  15
Lys His Ser Asn Gly Ser Tyr Ser Ala Phe Gly Glu Arg Asp Gly Asn
                20                  25                  30
Gly Asn Thr Trp
            35

<210> SEQ ID NO 41
<211> LENGTH: 826
<212> TYPE: PRT
<213> ORGANISM: gallus gallus

<400> SEQUENCE: 41

Ile Leu Ser Phe Phe Cys Leu Thr Val Arg Lys Met Trp Leu Lys Phe
1               5                   10                  15
Ile Leu Ala Ile Leu Leu His Ala Ala Gly Lys Glu Pro Glu
                20                  25                  30
Pro Gln Tyr Val Leu Met Val Pro Ala Val Leu Gln Ser Asp Ser Pro
            35                  40                  45
Ser Gln Val Cys Leu Gln Phe Phe Asn Leu Asn Gln Thr Ile Ser Val
        50                  55                  60
Arg Val Val Leu Glu Tyr Asp Thr Ile Asn Thr Thr Ile Phe Glu Lys
```

-continued

```
            65                  70                  75                  80
Asn Thr Thr Thr Ser Asn Gly Leu Gln Cys Leu Asn Phe Met Ile Pro
                    85                  90                  95
Pro Val Thr Ser Val Ser Leu Ala Phe Ile Ser Phe Thr Ala Lys Gly
                   100                 105                 110
Thr Thr Phe Asp Leu Lys Glu Arg Arg Ser Val Met Ile Trp Asn Met
                   115                 120                 125
Glu Ser Phe Val Phe Val Gln Thr Asp Lys Pro Ile Tyr Lys Pro Gly
        130                 135                 140
Gln Ser Val Met Phe Arg Val Ala Leu Asp Phe Asn Phe Lys Pro
145                 150                 155                 160
Val Gln Glu Met Tyr Pro Leu Ile Ala Val Gln Asp Pro Gln Asn Asn
                    165                 170                 175
Arg Ile Phe Gln Trp Gln Asn Val Thr Ser Glu Ile Asn Ile Val Gln
                    180                 185                 190
Ile Glu Phe Pro Leu Thr Glu Pro Ile Leu Gly Asn Tyr Lys Ile
                195                 200                 205
Ile Val Thr Lys Lys Ser Gly Glu Arg Thr Ser His Ser Phe Leu Val
210                 215                 220
Glu Glu Tyr Val Leu Pro Lys Phe Asp Val Thr Val Thr Ala Pro Gly
225                 230                 235                 240
Ser Leu Thr Val Met Asp Ser Glu Leu Thr Val Lys Ile Cys Ala Val
                    245                 250                 255
Tyr Thr Tyr Gly Gln Pro Val Glu Gly Lys Val Gln Leu Ser Val Cys
                260                 265                 270
Arg Asp Phe Asp Ser Tyr Gly Arg Cys Lys Lys Ser Pro Val Cys Gln
                275                 280                 285
Ser Phe Thr Lys Asp Leu Asp Thr Asp Gly Cys Leu Ser His Ile Leu
                290                 295                 300
Ser Ser Lys Val Phe Glu Leu Asn Arg Ile Gly Tyr Lys Arg Asn Leu
305                 310                 315                 320
Asp Val Lys Ala Ile Val Thr Glu Lys Glu Gln Val Cys Asn Leu Thr
                    325                 330                 335
Ala Thr Gln Ser Ile Ser Ile Thr Gln Val Met Ser Ser Leu Gln Phe
                    340                 345                 350
Glu Asn Val Asp His His Tyr Arg Arg Gly Ile Pro Tyr Phe Gly Gln
                355                 360                 365
Ile Lys Leu Val Asp Lys Asp Asn Ser Pro Ile Ser Asn Lys Val Ile
                370                 375                 380
Gln Leu Phe Val Asn Asn Lys Asn Thr His Asn Phe Thr Thr Asp Ile
385                 390                 395                 400
Asn Gly Ile Ala Pro Phe Ser Ile Asp Thr Ser Lys Ile Phe Asp Pro
                    405                 410                 415
Glu Leu Ser Leu Lys Ala Leu Tyr Lys Thr Ser Asp Gln Cys His Ser
                420                 425                 430
Glu Gly Trp Ile Glu Pro Ser Tyr Pro Asp Ala Ser Leu Ser Val Gln
                435                 440                 445
Arg Leu Tyr Ser Trp Thr Ser Ser Phe Val Arg Ile Glu Pro Leu Trp
        450                 455                 460
Lys Asp Met Ser Cys Gly Gln Lys Arg Met Ile Thr Val Tyr Tyr Ile
465                 470                 475                 480
Leu Asn Thr Glu Gly Tyr Glu His Ile Asn Ile Val Asn Phe Tyr Tyr
                    485                 490                 495
```

```
Val Gly Met Ala Lys Gly Lys Ile Val Leu Thr Gly Glu Ile Lys Val
            500             505             510
Asn Ile Gln Ala Asp Gln Asn Gly Thr Phe Met Ile Pro Leu Val Val
            515             520             525
Asn Glu Lys Met Ala Pro Ala Leu Arg Leu Leu Val Tyr Met Leu His
            530             535             540
Pro Ala Lys Glu Leu Val Ala Asp Ser Val Arg Phe Ser Ile Glu Lys
545             550             555             560
Cys Phe Lys Asn Lys Val Gln Leu Gln Phe Ser Glu Lys Gln Met Leu
            565             570             575
Thr Thr Ser Asn Val Ser Leu Val Ile Glu Ala Ala Ala Asn Ser Phe
            580             585             590
Cys Ala Val Arg Ala Val Asp Lys Ser Met Leu Leu Leu Lys Ser Glu
            595             600             605
Thr Glu Leu Ser Ala Glu Thr Ile Tyr Asn Leu His Pro Ile Gln Asp
            610             615             620
Leu Gln Gly Tyr Ile Phe Asn Gly Leu Asn Leu Glu Asp Asp Pro Gln
625             630             635             640
Asp Pro Cys Val Ser Ser Asp Asp Ile Phe His Lys Gly Leu Tyr Tyr
            645             650             655
Arg Pro Leu Thr Ser Gly Leu Gly Pro Asp Val Tyr Gln Phe Leu Arg
            660             665             670
Asp Met Gly Met Lys Phe Phe Thr Asn Ser Lys Ile Arg Gln Pro Thr
            675             680             685
Val Cys Thr Arg Glu Thr Val Arg Pro Pro Ser Tyr Phe Leu Asn Ala
            690             695             700
Gly Phe Thr Ala Ser Thr His His Val Lys Leu Ser Ala Glu Val Ala
705             710             715             720
Arg Glu Glu Arg Gly Lys Arg His Ile Leu Glu Thr Ile Arg Glu Phe
            725             730             735
Phe Pro Glu Thr Trp Ile Trp Asp Ile Ile Leu Ile Asn Ser Thr Gly
            740             745             750
Lys Ala Ser Val Ser Tyr Thr Ile Pro Asp Thr Ile Thr Glu Trp Lys
            755             760             765
Ala Ser Ala Phe Cys Val Glu Glu Leu Ala Gly Phe Gly Met Ser Val
            770             775             780
Pro Ala Thr Leu Thr Ala Phe Gln Pro Phe Phe Val Asp Leu Thr Leu
785             790             795             800
Pro Tyr Ser Ile Ile His Gly Glu Asp Phe Leu Val Arg Ala Asn Val
            805             810             815
Phe Asn Tyr Leu Asn His Cys Ile Lys Ile
            820             825
```

METHODS AND MATERIALS RELATING TO ALPHA-2-MACROGLOBULIN-LIKE POLYPEPTIDES AND POLYNUCLEOTIDES

1. CROSS REFERENCE TO RELATED APPLICATIONS

This application is a continuation-in-part of U.S. application Ser. No. 09/649,167 filed Aug. 23, 2000, entitled "Novel Nucleic Acids and Polypepticles," (now abandoned) which is a continuation-in-part of U.S. application Ser. No. 09/540,217 filed Mar. 31, 2000, entitled "Novel Nucleic Acids and Polypeptides," (now abandoned); and is a continuation-in-part application of U.S. application Ser. No. 09/684,711 filed Oct. 6, 2000, entitled "Methods and Materials Relating to Alpha-2-Macroglobulin-Like Polypeptides and Polynucleotides." (now abandoned) which is a continuation-in-part of U.S. application Ser. No. 09/560,875 filed Apr. 27, 2000, entitled "Novel Nucleic Acids and Polypeptides," (now abandoned) which is a continuation in part of U.S. application Ser. No. 09/496,914 filed Feb. 3, 2000, entitled "Novel Contigs Obtained from Various Libraries," (now abandoned); all of which are incorporated herein by reference in their entirety.

2. BACKGROUND

2.1 Technical Field

The present invention provides novel polynucleotides and proteins encoded by such polynucleotides, along with uses for these polynucleotides and proteins, for example in therapeutic, diagnostic and research methods. In particular, the invention relates to novel alpha-2-macroglobulin-like polypeptides.

2.2 Background Art

Identified polynucleotide and polypeptide sequences have numerous applications in, for example, diagnostics, forensics, gene mapping; identification of mutations responsible for genetic disorders or other traits, to assess biodiversity, and to produce many other types of data and products dependent on DNA and amino acid sequences. Proteins are known to have biological activity, for example, by virtue of their secreted nature in the case of leader sequence cloning, by virtue of their cell or tissue source in the case of PCR-based techniques, or by virtue of structural similarity to other genes of known biological activity. It is to these polypeptides and the polynucleotides encoding them that the present invention is directed. In particular, this invention is directed to novel alpha-2-macroglobulin-like polypeptides and polynucleotides.

Alpha-2-macroglobulin is a highly conserved proteinase inhibitor present in plasma at relatively high concentrations (2–4 mg/ml). It is unique in its ability to inhibit all the major classes of proteinases (Bhattacharjee et al (2000) J. Biol. Chem. 275, 26806–26811). Alpha-2-macroglobulin is a tetramer of four identical 180 kDa subunits that forms a hollow cylinder-like structure. It presents multiple target peptide bonds to attacking proteinases in its central "bait" domain. Binding of the proteinase and subsequent cleavage of the bait domain leads to a conformational change trapping the proteinase in the central cavity. The "activated" alpha-2-macroglobulin is now recognizable by its receptor. The receptor bound activated alpha-2-macroglobulin is then endocytosed, thus removing the potentially harmful proteinases from the circulation. Alpha-2-macroglobulin is the major proteinase inhibitor acting on foreign proteinases like snake venoms.

However, there are many other proteinase inhibitors in the circulation and it is proposed that alpha-2-macroglobulin may have other functions including binding to and regulation of cytokine and growth factor activity, promotion of tumoricidal capabilities of macrophages, and enhancement of antigen presentation. In accordance with above findings, numerous cytokines, growth factors and other plasma proteins have been shown to bind to alpha-2-macroglobulin including transforming growth factor-beta, platelet-derived growth factor, nerve growth factor, tumor necrosis factor-alpha, basic fibroblast growth factor, interleukin-6, beta-amyloid peptide, apolipoprotein E, myelin basic protein, leptin, beta-microglobulin and vascular endothelial growth factor (VEGF). Most of these proteins do not bind to the bait domain. Also, the native and activated alpha-2-macroglobulins show different binding specificities and kinetics. Binding of these proteins to alpha-2-macroglobulin could sequester them from proteinases and help maintain effective concentrations.

Epidemiological and genetic studies have indicated that alpha-2-macroglobulin deficiency and/or polymorphism may be associated with Alzheimer's disease and cerebral amyloid angiopathy, multiple sclerosis, and congenital antithrombin deficiency. Alpha-2-macroglobulin and VEGF are also implicated in rheumatoid arthritis and growth of various tumors, coronary or limb ischemia and retinopathies. Binding of alpha-2-macroglobulin to beta-microglobulin could be involved in regulation of immune response to tumors and viral infections. It is conceivable that alpha-2-macroglobulin exerts its effects by binding to various biologically important molecules and regulating their activities.

Thus, the alpha-2-macroglobulin-like polypeptides and polynucleotides of the invention may be used in the treatment of Alzheimer's disease and cerebral amyloid angiopathy, multiple sclerosis, congenital antithrombin deficiency, rheumatoid arthritis and growth of various tumors, coronary or limb ischemia, retinopathies, and regulation of immune response to tumors and viral infections.

3. SUMMARY OF THE INVENTION

This invention is based on the discovery of novel alpha-2-macroglobulin-like polypeptides, novel isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies. Specifically, the polynucleotides of the present invention are based on an alpha-2-macroglobulin-like polynucleotide isolated from a cDNA library prepared from fetal brain (Clontech) (SEQ ID NO: 1) and from uterus (Clontech) (SEQ ID NO: 26).

The compositions of the present invention additionally include vectors such as expression vectors containing the polynucleotides of the invention, cells genetically engineered to contain such polynucleotides and cells genetically engineered to express such polynucleotides.

The compositions of the invention provide isolated polynucleotides that include, but are not limited to, a polynucleotide comprising the nucleotide sequence set forth in SEQ ID NO: 1–3, 5, 26–28, or 30; or a fragment of SEQ ID NO: 1–3, 5, 26–28, or 30; a polynucleotide comprising the full length protein coding sequence of SEQ ID NO: 1–3, 5, 26–28, or 30 (for example, SEQ ID NO: 4 or 29); and a polynucleotide comprising the nucleotide sequence of the mature protein coding sequence of any of SEQ ID NO: 1–3, 5, 26–28, or 30. The polynucleotides of the present invention also include, but are not limited to, a polynucleotide that hybridizes under stringent hybridization conditions to (a) the complement of any of the nucleotide sequences set forth in SEQ ID NO: 1–3, 5, 26–28, or 30; (b) a nucleotide sequence encoding any of SEQ ID NO: 4, 6–22, 25, 29, or 31–40; a polynucleotide which is an allelic variant of any polynucleotides recited above having at least 70% polynucleotide sequence identity to the polynucleotides; a polynucleotide which encodes a species homolog (e.g. orthologs) of any of the peptides recited above; or a polynucleotide that encodes a polypeptide comprising a specific domain or truncation of the polypeptide comprising SEQ ID NO: 4 or 29.

A collection as used in this application can be a collection of only one polynucleotide. The collection of sequence information or unique identifying information of each sequence can be provided on a nucleic acid array. In one embodiment, segments of sequence information are provided on a nucleic acid array to detect the polynucleotide that contains the segment. The array can be designed to detect full-match or mismatch to the polynucleotide that contains the segment. The collection can also be provided in a computer-readable format.

This invention further provides cloning or expression vectors comprising at least a fragment of the polynucleotides set forth above and host cells or organisms transformed with these expression vectors. Useful vectors include plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The compositions of the present invention include polypeptides comprising, but not limited to, an isolated polypeptide selected from the group comprising the amino acid sequence of SEQ ID NO: 4, 6–22, 25, 29, or 31–40; or the corresponding full length or mature protein. Polypeptides of the invention also include polypeptides with biological activity that are encoded by (a) any of the polynucleotides having a nucleotide sequence set forth in SEQ ID NO: 1–3, 5, 26–28, or 30; or (b) polynucleotides that hybridize to the complement of the polynucleotides of (a) under stringent hybridization conditions. Biologically or immunologically active variants of any of the protein sequences listed as SEQ ID NO: 4, 6–22, 25, 29, or 31–40 and substantial equivalents thereof that retain biological or immunological activity are also contemplated. The polypeptides of the invention may be wholly or partially chemically synthesized but are preferably produced by recombinant means using the genetically engineered cells (e.g. host cells) of the invention.

The invention also provides compositions comprising a polypeptide of the invention. Pharmaceutical compositions of the invention may comprise a polypeptide of the invention and an acceptable carrier, such as a hydrophilic, e.g., pharmaceutically acceptable, carrier.

The invention also relates to methods for producing a polypeptide of the invention comprising culturing host cells comprising an expression vector containing at least a fragment of a polynucleotide encoding the polypeptide of the invention in a suitable culture medium under conditions permitting expression of the desired polypeptide, and purifying the protein or peptide from the culture or from the host cells. Preferred embodiments include those in which the protein produced by such a process is a mature form of the protein.

Polynucleotides according to the invention have numerous applications in a variety of techniques known to those skilled in the art of molecular biology. These techniques include use as hybridization probes, use as oligomers, or primers, for PCR, use in an array, use in computer-readable media, use for chromosome and gene mapping, use in the recombinant production of protein, and use in generation of antisense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide. Such antibodies, particularly monoclonal antibodies, are useful for detecting or quantitating the polypeptide in tissue. The polypeptides of the invention can also be used as molecular weight markers, and as a food supplement.

Methods are also provided for preventing, treating, or ameliorating a medical condition which comprises the step of administering to a mammalian subject a therapeutically effective amount of a composition comprising a peptide of the present invention and a pharmaceutically acceptable carrier.

Thus, the alpha-2-macroglobulin-like polypeptides and polynucleotides of the invention may be used in the treatment of Alzheimer's disease and cerebral amyloid angiopathy, multiple sclerosis, congenital antithrombin deficiency, rheumatoid arthritis and growth of various tumors, coronary or limb ischemia, retinopathies, and regulation of immune response to tumors and viral infections.

The methods of the invention also provide methods for the treatment of disorders as recited herein which comprise the administration of a therapeutically effective amount of a composition comprising a polynucleotide or polypeptide of the invention and a pharmaceutically acceptable carrier to a mammalian subject exhibiting symptoms or tendencies related to disorders as recited herein. In addition, the invention encompasses methods for treating diseases or disorders as recited herein comprising the step of administering a composition comprising compounds and other substances that modulate the overall activity of the target gene products and a pharmaceutically acceptable carrier. Compounds and other substances can effect such modulation either on the level of target gene/protein expression or target protein activity. Specifically, methods are provided for preventing, treating or ameliorating a medical condition, including viral diseases, which comprises administering to a mammalian subject, including but not limited to humans, a therapeutically effective amount of a composition comprising a polypeptide of the invention or a therapeutically effective amount of a composition comprising a binding partner of (e.g., antibody specifically reactive for) alpha-2-macroglobulin-like polypeptides of the invention. The mechanics of the particular condition or pathology will dictate whether the polypeptides of the invention or binding partners (or inhibitors) of these would be beneficial to the individual in need of treatment.

According to this method, polypeptides of the invention can be administered to produce an in vitro or in vivo inhibition of cellular function. A polypeptide of the invention can be administered in vivo alone or as an adjunct to other therapies. Conversely, protein or other active ingredients of the present invention may be included in formulations of a particular agent to minimize side effects of such an agent.

The invention further provides methods for manufacturing medicaments useful in the above-described methods.

The present invention further relates to methods for detecting the presence of the polynucleotides or polypeptides of the invention in a sample (e.g., tissue or sample). Such methods can, for example, be utilized as part of prognostic and diagnostic evaluation of disorders as recited herein and for the identification of subjects exhibiting a predisposition to such conditions.

The invention provides a method for detecting a polypeptide of the invention in a sample comprising contacting the sample with a compound that binds to and forms a complex with the polypeptide under conditions and for a period sufficient to form the complex and detecting formation of the complex, so that if a complex is formed, the polypeptide is detected.

The invention also provides kits comprising polynucleotide probes and/or monoclonal antibodies, and optionally quantitative standards, for carrying out methods of the invention. Furthermore, the invention provides methods for evaluating the efficacy of drugs, and monitoring the progress of patients, involved in clinical trials for the treatment of disorders as recited above.

The invention also provides methods for the identification of compounds that modulate (i.e., increase or decrease) the expression or activity of the polynucleotides and/or polypeptides of the invention. Such methods can be utilized, for example, for the identification of compounds that can ameliorate symptoms of disorders as recited herein. Such methods can include, but are not limited to, assays for identifying compounds and other substances that interact with (e.g., bind to) the polypeptides of the invention.

The invention provides a method for identifying a compound that binds to the polypeptide of the present invention comprising contacting the compound with the polypeptide under conditions and for a time sufficient to form a polypeptide/compound complex and detecting the complex, so that if the polypeptide/compound complex is detected, a compound that binds to the polypeptide is identified.

Also provided is a method for identifying a compound that binds to the polypeptide comprising contacting the compound with the polypeptide in a cell for a time sufficient to form a polypeptide/compound complex wherein the complex drives expression of a reporter gene sequence in the cell and detecting the complex by detecting reporter gene sequence expression so that if the polypeptide/compound complex is detected a compound that binds to the polypeptide is identified.

4. BRIEF DESCRIPTION OF THE DRAWINGS

FIGS. 1A, 1B and 1C show the BLASTX amino acid sequence alignment between the protein encoded by SEQ ID NO: 3 (i.e. SEQ ID NO: 4) alpha-2-macroglobulin-like polypeptide and alpha-2-macroglobulin precursor SEQ ID NO: 23, indicating that the two sequences share 58% similarity and 39% identity over the same amino acid residues of SEQ ID NO: 4, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIGS. 2A, 2B, and 2C show the BLASTX amino acid sequence alignment between the protein encoded by SEQ ID NO: 3 (i.e. SEQ ID NO: 4) alpha-2-macroglobulin-like polypeptide and recombinant human alpha-2-macroglobulin, SEQ ID NO: 24, indicating that the two sequences share 58% similarity and 39% identity over the same amino acid residues of SEQ ID NO: 4, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIGS. 3A and 3B show the BLASTX amino acid sequence alignment between the protein encoded by SEQ ID NO: 28 (i.e. SEQ ID NO: 29) alpha-2-macroglobulin-like polypeptide and ovos_chick ovostatin, SEQ ID NO: 41, indicating that the two sequences share 53% similarity and 34% identity over the same amino acid residues of SEQ ID NO: 29, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIGS. 4A and 4B show the BLASTX amino acid sequence alignment between the protein encoded by SEQ ID NO: 28 (i.e. SEQ ID NO: 29) alpha-2-macroglobulin-like polypeptide and the first 812 amino acid residues of recombinant human alpha-2-macroglobulin in SEQ ID NO: 24, indicating that the two sequences share 53% similarity and 35% identity over the same amino acid residues of SEQ ID NO: 29, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

5. DETAILED DESCRIPTION OF THE INVENTION

The alpha-2-macroglobulin-like polypeptide of SEQ ID NO: 4 is an approximately 1508-amino acid secreted protein with a predicted molecular mass of approximately 169 kDa unglycosylated. Protein database searches with the BLASTX algorithm (Altschul S. F. et al., J. Mol. Evol. 36:290–300 (1993) and Altschul S. F. et al., J. Mol. Biol. 21:403–10 (1990), herein incorporated by reference) indicate that SEQ ID NO: 4 is homologous to alpha-2-macroglobulin. Protein database searches with GeneAtlas software (Molecular Simulations Inc., San Diego, Calif.) indicate that SEQ ID NO: 4 shares structural homology with complement component C3d and alpha-2-macroglobulin.

FIGS. 1A, 1B and 1C show the BLASTX amino acid sequence alignment between the protein encoded by SEQ ID NO: 3 (i.e. SEQ ID NO: 4) alpha-2-macroglobulin-like polypeptide and alpha-2-macroglobulin precursor SEQ ID NO: 23, indicating that the two sequences share 58% similarity and 39% identity over the same amino acid residues of SEQ ID NO: 4.

FIGS. 2A, 2B, and 2C show the BLASTX amino acid sequence alignment between the protein encoded by SEQ ID NO: 3 (i.e. SEQ ID NO: 4) alpha-2-macroglobulin-like polypeptide and recombinant human alpha-2-macroglobulin, SEQ ID NO: 24, indicating that the two sequences share 58% similarity and 39% identity over the same amino acid residues of SEQ ID NO: 4.

A predicted approximately seventeen-residue signal peptide is encoded from approximately residue 1 through residue 17 of SEQ ID NO: 4 (SEQ ID NO: 19). The extracellular portion is useful on its own. This can be confirmed by expression in mammalian cells and sequencing of the cleaved product. The signal peptide region was predicted using the Kyte-Doolittle hydrophobocity prediction algorithm (J. Mol Biol, 157, pp. 105–31 (1982), incorporated herein by reference) and Neural Network SignalP V1.1 program (from Center for Biological Sequence Analysis, The Technical University of Denmark). One of skill in the art will recognize that the actual cleavage site may be different than that predicted by the computer program.

Using eMATRIX software package (Stanford University, Stanford, Calif.) (Wu et al., J. Comp. Biol., vol. 6, pp. 219–235 (1999), herein incorporated by reference), the alpha-2-macroglobulin-like polypeptide of SEQ ID NO: 4 is expected to have twelve alpha-2-macroglobulin signatures as shown in the table. Using eMATRIX software package (Stanford University, Stanford, Calif.) (Wu et al., J. Comp. Biol., vol. 6, pp. 219–235 (1999), herein incorporated by reference), the alpha-2-macroglobulin-like polypeptide of SEQ ID NO: 4 is also expected to have an anaphylatoxin domain proteins domain signature as shown in the table. The domains corresponding to SEQ ID NO: 6–18 are as follows wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine:

| SEQ ID NO | p-value | Signature ID NO | Name | Amino acid sequence encoded (start and end amino acid position) |
| --- | --- | --- | --- | --- |
| 6 | 3.382e-27 | BL00477J | alpha-2-macroglobulin family thiolester region proteins | IVAWLAKQHNAYGG FSSTQDTVVALQALA KY (1241–1271) |
| 7 | 8.5e-25 | BL00477F | alpha-2-macroglobulin family thiolester region proteins | AFKPFFVDLTLPYSVV RGESFRLTATIFNY (785–814) |
| 8 | 8.826e-23 | BL00477G | alpha-2-macroglobulin family thiolester region proteins | LVQMPSGCGEQNMV LFAPIIYVLQYLEKAG LL (983–1014) |
| 9 | 9.8e-23 | BL00477A | alpha-2-macroglobulin family thiolester region proteins | TFVQTDKPLYTPGQQ VYFRIVTMDSNFVP (122–150) |
| 10 | 5.5e-16 | BL00477L | alpha-2-macroglobulin family thiolester region proteins | FTISQSVLVTNLKPATI KVYDYYLPGSFKLSQ Y (1437–1469) |
| 11 | 4.529e-14 | BL00477K | alpha-2-macroglobulin family thiolester region proteins | SNMAIVEVKMLSGFS PMEGTNQLL (1382–1405) |
| 12 | 4.541e-13 | BL01177E | anaphylatoxin domain proteins | FVDLTLPYSVVRGESF RLTATIFNYLK (790–816) |
| 13 | 6.538e-13 | BL00477E | alpha-2-macroglobulin family thiolester region proteins | VPDAITEWKAMSFCT SQSRGF (755–775) |
| 14 | 6.625e-13 | BL00477B | alpha-2-macroglobulin family thiolester region proteins | FSVEEYVLPKFKV (209–221) |
| 15 | 2.65e-12 | BL00477I | alpha-2-macroglobulin family thiolester region proteins | WMAGNQLPSGCYAN VGNLLHTAMKGGV (1085–1111) |
| 16 | 4.073e-12 | BL00477D | alpha-2-macroglobulin family thiolester region proteins | RQYFPETWLW (729–738) |

-continued

| SEQ ID NO | p-value | Signature ID NO | Name | Amino acid sequence encoded (start and end amino acid position) |
|---|---|---|---|---|
| 17 | 5.395e-12 | BL00477H | alpha-2-macroglobulin family thiolester region proteins | NTWLTAFVTKCF (1054–1065) |
| 18 | 1.161e-10 | BL00477C | alpha-2-macroglobulin family thiolester region proteins | FLVKICCRYTYGKPM LG (236–252) |

Using Molecular Simulations Inc. GeneAtlas software (Molecular Simulations Inc., San Diego, Calif.), the alpha-2-macroglobulin-like polypeptide SEQ ID NO:4 was determined to have a region at residues 977–1276 with characteristic motif for complement component C3d (SEQ ID NO: 21), and at residues 1343–1479 with characteristic motif for receptor domain for alpha-2-macroglobulin domain (SEQ ID NO: 22). The domains corresponding to SEQ ID NO: 21 and 22 are as follows wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine:

Complement component C3d homologous sequence

LQNLDGLVQMPSGCGEQNMVLFAPIIYVLQYLEKAGLLTEEIRSRAVGFLEIGYQKELM

YKHSNGSYSAFGERDGNGNTWLTAFVTKCFGQAQKFIFIDPKNIQDALKWMAGNQLPS

GCYANVGNLLHTAMKGGVDDEVSLTAYVTAALLEMGKDVDDPMVSQGLRCLKNSAT

STTNLYTQALLAYIFSLAGEMDIRNILLKQLDQQAIISGESIYWSQKPTPSSNASPWSEPA

AVDVELTAYALLAQLTKPSLTQKEIAKATSIVAWLAKQHNAYGGFSSTQDTVVALQAL

AKYATTAY (designated as SEQ ID NO: 21) with PSI-BLAST e-value of 4.4e-87, protein database identification number entry=1c3d [Research collaboratory for Structural Bioinformatics.], verify score=0.49, located at residues 977·1276 of SEQ ID NO: 4.

Receptor domain alpha-2-macroglobulin domain

NMKTFSLSVEIGKARCEQPTSPRSLTLTIHTSYVGSRSSSNMAIVEVKMLSGFSPM

EGTNQLLLQQPLVKKVEFGTDTLNIYLDELIKNTQTYTFTISQSVLVTNLKPATIKVYDY

YLPGSFKLSQYTIVWSMNNDS (designated as SEQ ID NO: 22) with PSI-BLAST e-value of 4.4e-52, protein database identification number entry =1bv8, [Research collaboratory for Structural Bioinformatics.), verify score =0.49, located at residues 1349–1479 of SEQ ID NO: 4.

The alpha-2-macroglobulin-like polypeptide of SEQ ID NO: 29 is an approximately 912-amino acid secreted protein with a predicted molecular mass of approximately 102-kDa unglycosylated. Protein database searches with the BLASTX algorithm (Altschul S. F. et al., J. Mol. Evol. 36:290–300 (1993) and Altschul S. F. et al., J. Mol. Biol. 21:403–10 (1990), herein incorporated by reference) indicate that SEQ ID NO: 29 is homologous to ovos_chick ovostatin and recombinant alpha-2-macroglobulin.

FIGS. 3A and 3B show the BLASTX amino acid sequence alignment between the protein encoded by SEQ ID NO: 28 (i.e. SEQ ID NO: 29) alpha-2-macroglobulin-like polypeptide and ovos_chick ovostatin precursor SEQ ID NO: 41, indicating that the two sequences share 53% similarity and 34% identity over the same amino acid residues of SEQ ID NO: 29. FIGS. 4A and 4B show the BLASTX amino acid sequence alignment between the protein encoded by SEQ ID NO: 28 (i.e. SEQ ID NO: 29) alpha-2-macroglobulin-like polypeptide and the first 812 amino acids of recombinant human alpha-2-macroglobulin in SEQ ID NO: 24, indicating that the two sequences share 53% similarity and 35% identity over the same amino acid residues of SEQ ID NO: 29.

A predicted approximately thirty-residue signal peptide is encoded from approximately residue 1 through residue 30 of SEQ ID NO: 29 (SEQ ID NO: 38). The extracellular portion is useful on its own. This can be confirmed by expression in mammalian cells and sequencing of the cleaved product. The signal peptide region was predicted using the Kyte-Doolittle hydrophobocity prediction algorithm (J. Mol Biol, 157, pp. 105–31 (1982), incorporated herein by reference) and Neural Network SignalP V1.1 program (from Center for Biological Sequence Analysis, The Technical University of Denmark). One of skill in the art will recognize that the actual cleavage site may be different than that predicted by the computer program.

Using eMATRIX software package (Stanford University, Stanford, Calif.) (Wu et al., J. Comp. Biol., vol. 6, pp. 219–235 (1999), herein incorporated by reference), the alpha-2-macroglobulin-like polypeptide of SEQ ID NO: 29 is expected to have six alpha-2-macroglobulin family thiolester regions as shown in the table (SEQ ID NO: 31–32, and 34–37). Using eMATRIX software package (Stanford University, Stanford, Calif.) (Wu et al, J. Comp. Biol., vol. 6, pp. 219–235 (1999), herein incorporated by reference), the alpha-2-macroglobulin-like polypeptide of SEQ ID NO: 29 is also expected to have an anaphylatoxin domain protein signature as shown in the table (SEQ ID NO: 33). The domains corresponding to SEQ ID NO: 31–37 are as follows wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine:

membrane trafficking, including the export of secretory or enzymatic molecules as part of a normal or disease process.

The terms "complementary" or "complementarity" refer to the natural binding of polynucleotides by base pairing. For example, the sequence 5'-AGT-3' binds to the complementary sequence 3'-TCA-5'. Complementarity between two single-stranded molecules may be "partial" such that only some of the nucleic acids bind or it may be "complete" such that total complementarity exists between the single stranded molecules. The degree of complementarity between the nucleic acid strands has significant effects on the efficiency and strength of the hybridization between the nucleic acid strands.

The term "embryonic stem cells (ES)" refers to a cell that can give rise to many differentiated cell types in an embryo

| SEQ ID NO | p-value | Signature ID NO | Name | Amino acid sequence encoded (start and end amino acid position) |
|---|---|---|---|---|
| 31 | 8.500e-25 | BL00477F | alpha-2-macroglobulin family thiolester region proteins | AFKPFFVDLTLPYSVV RGESFRLTATIFNY (799–828) |
| 32 | 9.800e-23 | BL00477A | alpha-2-macroglobulin family thiolester region proteins | TFVQTDKPLYTPGQQ VYFRIVTMDSNFVP (135–163) |
| 34 | 6.538e-13 | BL00477E | alpha-2-macroglobulin family thiolester region proteins | VPDAITEWKAMSFCT SQSRGF (769–789) |
| 35 | 6.625e-13 | BL00477B | alpha-2-macroglobulin family thiolester region proteins | FSVEEYVLPKFKV (222–234) |
| 36 | 4.073e-12 | BL00477D | alpha-2-macroglobulin family thiolester region proteins | RQYFPETWLW (743–752) |
| 37 | 1.161e-10 | BL00477C | alpha-2-macroglobulin family thiolester region proteins | FLVKICCRYTYGKPM LG (249–265) |
| 33 | 4.541e-13 | BL01177E | anaphylatoxin domain proteins | FVDLTLPYSVVRGESF RLTATIFNYLK (804–830) |

In particular, the alpha-2-macroglobulin-like polypeptides and polynucleotides of the invention may be used in the treatment of Alzheimer's disease and cerebral amyloid angiopathy, multiple sclerosis, congenital antithrombin deficiency, rheumatoid arthritis and growth of various tumors, coronary or limb ischemia, retinopathies, and regulation of immune response to tumors and viral infections.

5.1 Definitions

It must be noted that as used herein and in the appended claims, the singular forms "a", "an" and "the" include plural references unless the context clearly dictates otherwise.

The term "active" refers to those forms of the polypeptide that retain the biologic and/or immunologic activities of any naturally occurring polypeptide. According to the invention, the terms "biologically active" or "biological activity" refer to a protein or peptide having structural, regulatory or biochemical functions of a naturally occurring molecule. Likewise "biologically active" or "biological activity" refers to the capability of the natural, recombinant or synthetic alpha-2-macroglobulin-like peptide, or any peptide thereof, to induce a specific biological response in appropriate animals or cells and to bind with specific antibodies. The term "alpha-2-macroglobulin-like biological activity" refers to biological activity that is similar to the biological activity of an alpha-2-macroglobulin-like polypeptide.

The term "activated cells" as used in this application are those cells which are engaged in extracellular or intracellular or an adult, including the germ cells. The term "germ line stem cells (GSCs)" refers to stem cells derived from primordial stem cells that provide a steady and continuous source of germ cells for the production of gametes. The term "primordial germ cells (PGCs)" refers to a small population of cells set aside from other cell lineages particularly from the yolk sac, mesenteries, or gonadal ridges during embryogenesis that have the potential to differentiate into germ cells and other cells. PGCs are the source from which GSCs and ES cells are derived The PGCs, the GSCs and the ES cells are capable of self-renewal. Thus these cells not only populate the germ line and give rise to a plurality of terminally differentiated cells that comprise the adult specialized organs, but are able to regenerate themselves.

The term "expression modulating fragment," EMF, means a series of nucleotides that modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs is nucleic acid fragments which induce the expression of an operably linked ORF in response to a specific regulatory factor or physiological event.

The terms "nucleotide sequence" or "nucleic acid" or "polynucleotide" or "oligonculeotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. In the sequences herein, A is adenine, C is cytosine, G is guanine, T is thymine, and N is G, A, C, or T(U). It is contemplated that where the polynucleotide is RNA, the T (thymine) in the sequence herein may be replaced with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" or "probe" or "primer" are used interchangeably and refer to a sequence of nucleotide residues which are at least about 5 nucleotides, more preferably at least about 7 nucleotides, more preferably at least about 9 nucleotides, more preferably at least about 11 nucleotides and most preferably at least about 17 nucleotides. The fragment is preferably less than about 500 nucleotides, preferably less than about 200 nucleotides, more preferably less than about 100 nucleotides, more preferably less than about 50 nucleotides and most preferably less than 30 nucleotides. Preferably the probe is from about 6 nucleotides to about 200 nucleotides, preferably from about 15 to about 50 nucleotides, more preferably from about 17 to 30 nucleotides and most preferably from about 20 to 25 nucleotides. Preferably the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention. Preferably the fragment comprises a sequence substantially similar to a portion of SEQ ID NO: 1–3, 5, 26–28, or 30

Probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250). They may be labeled by nick translation, Klenow fill-in reaction, PCR, or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The nucleic acid sequences of the present invention also include the sequence information from any of the nucleic acid sequences of SEQ ID NO: 1–3, 5, 26–28, or 30. The sequence information can be a segment of SEQ ID NO: 1–3, 5, 26–28, or 30 that uniquely identifies or represents the sequence information of SEQ ID NO: 1–3, 5, 26–28, or 30. One such segment can be a twenty-mer nucleic acid sequence because the probability that a twenty-mer is fully matched in the human genome is 1 in 300. In the human genome, there are three billion base pairs in one set of chromosomes. Because $4^{20}$ possible twenty-mers exist, there are 300 times more twenty-mers than there are base pairs in a set of human chromosome. Using the same analysis, the probability for a seventeen-mer to be fully matched in the human genome is approximately 1 in 5.

When these segments are used in arrays for expression studies, fifteen-mer segments can be used. The probability that the fifteen-mer is fully matched in the expressed sequences is also approximately one in five because expressed sequences comprise less than approximately 5% of the entire genome sequence.

Similarly, when using sequence information for detecting a single mismatch, a segment can be a twenty-five mer. The probability that the twenty-five mer would appear in a human genome with a single mismatch is calculated by multiplying the probability for a full match ($1 \div 4^{25}$) times the increased probability for mismatch at each nucleotide position ($3 \times 25$). The probability that an eighteen mer with a single mismatch can be detected in an array for expression studies is approximately one in five. The probability that a twenty-mer with a single mismatch can be detected in a human genome is approximately one in five.

The term "open reading frame," ORF, means a series of nucleotide triplets coding for amino acids without any termination codons and is a sequence translatable into protein.

The terms "operably linked" or "operably associated" refer to functionally related nucleic acid sequences. For example, a promoter is operably associated or operably linked with a coding sequence if the promoter controls the transcription of the coding sequence. While operably linked nucleic acid sequences can be contiguous and in the same reading frame, certain genetic elements e.g. repressor genes are not contiguously linked to the coding sequence but still control transcription/translation of the coding sequence.

The term "pluripotent" refers to the capability of a cell to differentiate into a number of differentiated cell types that are present in an adult organism. A pluripotent cell is restricted in its differentiation capability in comparison to a totipotent cell.

The terms "polypeptide" or "peptide" or "amino acid sequence" refer to an oligopeptide, peptide, polypeptide or protein sequence or fragment thereof and to naturally occurring or synthetic molecules. A polypeptide "fragment," "portion," or "segment" is a stretch of amino acid residues of at least about 5 amino acids, preferably at least about 7 amino acids, more preferably at least about 9 amino acids and most preferably at least about 17 or more amino acids. The peptide preferably is not greater than about 200 amino acids, more preferably less than 150 amino acids and most preferably less than 100 amino acids. Preferably the peptide is from about 5 to about 200 amino acids. To be active, any polypeptide must have sufficient length to display biological and/or immunological activity.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "translated protein coding portion" means a sequence which encodes for the full length protein which may include any leader sequence or a processing sequence.

The term "mature protein coding sequence" refers to a sequence which encodes a peptide or protein without any leader/signal sequence. The peptide may have the leader sequences removed during processing in the cell or the protein may have been produced synthetically or using a polynucleotide only encoding for the mature protein coding sequence. It is contemplated that the mature protein coding sequence may or may not include the initial methionine. The initial methionine is often removed in the cell during processing of the peptide.

The term "derivative" refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins.

The term "variant" (or "analog") refers to any polypeptide differing from naturally occurring polypeptides by amino acid insertions, deletions, and substitutions, created using, e g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

The terms "purified" or "substantially purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other components normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins that are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2):134–143) and factors released from damaged cells (e.g. Interleukin-1 Receptor Antagonist, see Arend, W. P. et. al. (1998) Annu. Rev. Immunol. 16:27–55).

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

The term "stringent" is used to refer to conditions that are commonly understood in the art as stringent. Stringent conditions can include highly stringent conditions (i.e., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.). Other exemplary hybridization conditions are described herein in the examples.

In instances of hybridization of deoxyoligonucleotides, additional exemplary stringent hybridization conditions include washing in 6×SSC/0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35% (i.e., the number of individual residue substitutions, additions, and/or deletions in a substantially equivalent sequence, as compared to the corresponding reference sequence, divided by the total number of residues in the substantially equivalent sequence is about 0.35 or less). Such a sequence is said to have 65% sequence identity to the listed sequence. In one embodiment, a substantially equivalent, e.g., mutant, sequence of the invention varies from a listed sequence by no more than 30% (70% sequence identity); in a variation of this embodiment, by no more than 25% (75% sequence identity); and in a further variation of this embodiment, by no more than 20% (80% sequence identity); and in a further variation of this embodiment, by no more than 10% (90% sequence identity); and in a further variation of this embodiment, by no more that 5% (95% sequence identity); and in a further variation of this embodiment by no more than 2% (98% sequence identity). Substantially equivalent, e.g., mutant, amino acid sequences according to the invention preferably have at least 80% sequence identity with a listed amino acid sequence, more preferably at least 90% sequence identity, more preferably at least 95% sequence identity, and most preferably at least 98% sequence identity. Substantially equivalent nucleotide sequence of the invention can have lower percent sequence identities, taking into account, for example, the redundancy or degeneracy of the genetic code. Preferably, nucleotide sequence has at least about 65% identity, more preferably at least about 75% identity, more preferably at least about 95% identity, and most preferably at least 98% identity. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method (Hein, J. (1990) Methods Enzymol. 183:626–645). Identity between sequences can also be determined by other methods known in the art, e.g. by varying hybridization conditions.

The term "totipotent" refers to the capability of a cell to differentiate into all of the cell types of an adult organism.

The term "transformation" means introducing DNA into a suitable host cell so that the DNA is replicable, either as an extrachromosomal element, or by chromosomal integration. The term "transfection" refers to the taking up of an expression vector by a suitable host cell, whether or not any coding sequences are in fact expressed. The term "infection" refers to the introduction of nucleic acids into a suitable host cell by use of a virus or viral vector.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below. The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

Each of the above terms is meant to encompass all that is described for each, unless the context dictates otherwise.

5.2 Nucleic Acids of the Invention

The invention is based on the discovery of novel secreted alpha-2-macroglobulin-like polypeptides, the polynucleotides encoding the alpha-2-macroglobulin-like polypeptides and the use of these compositions for the diagnosis, treatment or prevention of cancers and other immunological disorders.

The isolated polynucleotides of the invention include, but are not limited to a polynucleotide comprising any of the nucleotide sequences of SEQ ID NO: 1–3, 5, 26–28, or 30; a fragment of SEQ ID NO: 1–3, 5, 26–28, or 30; a polynucleotide comprising the full length protein coding sequence of SEQ ID NO: 1–3, 5, 26–28, or 30 (for example SEQ ID NO: 4 or 29); and a polynucleotide comprising the nucleotide sequence encoding the mature protein coding sequence of the polynucleotides of any one of SEQ ID NO: 1–3, 5, 26–28, or 30. The polynucleotides of the present invention also include, but are not limited to, a polynucleotide that hybridizes under stringent conditions to (a) the complement of any of the nucleotides sequences of SEQ ID NO: 1–3, 5, 26–28, or 30; (b) a polynucleotide encoding any one of the polypeptides of SEQ ID NO: 4, 6–22, 25, 29, or 31–40; (c) a polynucleotide which is an allelic variant of any polynucleotides recited above; (d) a polynucleotide which encodes a species homolog of any of the proteins recited above; or (e) a polynucleotide that encodes a polypeptide comprising a specific domain or truncation of the polypeptides of SEQ ID NO: 4, 6–22, 25, 29, or 31–40. Domains of interest may depend on the nature of the encoded polypeptide; e.g., domains in receptor-like polypeptides include ligand-binding, extracellular, transmembrane, or cytoplasmic domains, or combinations thereof; domains in immunoglobulin-like proteins include the variable immunoglobulin-like domains; domains in enzyme-like polypeptides include catalytic and substrate binding domains; and domains in ligand polypeptides include receptor-binding domains.

The polynucleotides of the invention include naturally occurring or wholly or partially synthetic DNA, e.g., cDNA and genomic DNA, and RNA, e.g., mRNA. The polynucleotides may include all of the coding region of the cDNA or may represent a portion of the coding region of the cDNA.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Further 5' and 3' sequence can be obtained using methods known in the art. For example, full length cDNA or genomic DNA that corresponds to any of the polynucleotides of SEQ ID NO: 1–3, 5, 26–28, or 30 can be obtained by screening appropriate cDNA or genomic DNA libraries under suitable hybridization conditions using any of the polynucleotides of SEQ ID NO: 1–3, 5, 26–28, or 30 or a portion thereof as a probe. Alternatively, the polynucleotides of SEQ ID NO: 1–3, 5, 26–28, or 30 may be used as the basis for suitable primer(s) that allow identification and/or amplification of genes in appropriate genomic DNA or cDNA libraries.

The nucleic acid sequences of the invention can be assembled from ESTs and sequences (including cDNA and genomic sequences) obtained from one or more public databases, such as dbEST, gbpri, and UniGene. The EST sequences can provide identifying sequence information, representative fragment or segment information, or novel segment information for the full-length gene.

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, more typically at least about 90%, and even more typically at least about 95%, sequence identity to a polynucleotide recited above.

Included within the scope of the nucleic acid sequences of the invention are nucleic acid sequence fragments that hybridize under stringent conditions to any of the nucleotide sequences of SEQ ID NO: 1–3, 5, 26–28, or 30, or complements thereof, which fragment is greater than about 5 nucleotides, preferably 7 nucleotides, more preferably greater than 9 nucleotides and most preferably greater than 17 nucleotides. Fragments of, e.g. 15, 17, or 20 nucleotides or more that are selective for (i.e. specifically hybridize to) any one of the polynucleotides of the invention are contemplated. Probes capable of specifically hybridizing to a polynucleotide can differentiate polynucleotide sequences of the invention from other polynucleotide sequences in the same family of genes or can differentiate human genes from genes of other species, and are preferably based on unique nucleotide sequences.

The sequences falling within the scope of the present invention are not limited to these specific sequences, but also include allelic and species variations thereof. Allelic and species variations can be routinely determined by comparing the sequence provided in SEQ ID NO: 1–3, 5, 26–28, or 30, a representative fragment thereof, or a nucleotide sequence at least 90% identical, preferably 95% identical, to SEQ ID NO: 1–3, 5, 26–28, or 30 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another codon that encodes the same amino acid is expressly contemplated.

The nearest neighbor result for the nucleic acids of the present invention, including SEQ ID NO: 1–3, 5, 26–28, or 30, can be obtained by searching a database using an algorithm or a program. Preferably, a BLAST which stands for Basic Local alignment Search Tool is used to search for local sequence alignments (Altshul, S.F. J. Mol. Evol. 36 290–300 (1993) and Altschul S. F. et al. J. Mol. Biol. 21:403–410 (1990))

Species homologs (or orthologs) of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. Nucleic acids encoding the amino acid sequence variants are preferably constructed by mutating the polynucleotide to encode an amino acid sequence that does not occur in nature. These nucleic acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells and sequences such as FLAG or poly-histidine sequences useful for purifying the expressed protein.

In a preferred method, polynucleotides encoding the novel amino acid sequences are changed via site-directed mutagenesis. This method uses oligonucleotide sequences to alter a polynucleotide to encode the desired amino acid variant, as well as sufficient adjacent nucleotides on both sides of the changed amino acid to form a stable duplex on either side of the site being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives a polynucleotide encoding the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology*, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Polynucleotides encoding preferred polypeptide truncations of the invention can be used to generate polynucleotides encoding chimeric or fusion proteins comprising one or more domains of the invention and heterologous protein sequences.

The polynucleotides of the invention additionally include the complement of any of the polynucleotides recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions that can routinely isolate polynucleotides of the desired sequence identities.

In accordance with the invention, polynucleotide sequences comprising the mature protein coding sequences corresponding to any one of SEQ ID NO: 4, 6–22, 25, 29, or 31–40, or functional equivalents thereof, may be used to generate recombinant DNA molecules that direct the expression of that nucleic acid, or a functional equivalent thereof, in appropriate host cells. Also included are the cDNA inserts of any of the clones identified herein.

A polynucleotide according to the invention can be joined to any of a variety of other nucleotide sequences by well-established recombinant DNA techniques (see Sambrook J et al., (1989) Molecular Cloning: A Laboratory Manual, Cold Spring Harbor Laboratory, NY). Useful nucleotide sequences for joining to polynucleotides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The present invention further provides recombinant constructs comprising a nucleic acid having any of the nucleotide sequences of SEQ ID NO: 1–3, 5, 26–28, or 30 or a fragment thereof or any other polynucleotides of the invention. In one embodiment, the recombinant constructs of the present invention comprise a vector, such as a plasmid or viral vector, into which a nucleic acid having any of the nucleotide sequences of SEQ ID NO: 1–3, 5, 26–28, or 30 or a fragment thereof is inserted, in a forward or reverse orientation. In the case of a vector comprising one of the ORFs of the present invention, the vector may further comprise regulatory sequences, including for example, a promoter, operably linked to the ORF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotide of the invention may be operably linked to an expression control sequence such as the pMT2 or pED expression vectors disclosed in Kaufman et al., *Nucleic Acids Res.* 19, 4485–4490 (1991), in order to produce the protein recombinantly. Many suitable expression control sequences are known in the art. General methods of expressing recombinant proteins are also known and are exemplified in R. Kaufman, *Methods in Enzymology* 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda PR, and trc. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art. Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an amino terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotech, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Polynucleotides of the invention can also be used to induce immune responses. For example, as described in Fan et al., *Nat. Biotech.* 17:870–872 (1999), incorporated herein by reference, nucleic acid sequences encoding a polypeptide may be used to generate antibodies against the encoded polypeptide following topical administration of naked plasmid DNA or following injection, and preferably intramuscular injection of the DNA. The nucleic acid sequences are preferably inserted in a recombinant expression vector and may be in the form of naked DNA.

5.3 Antisense

Another aspect of the invention pertains to isolated antisense nucleic acid molecules that are hybridizable to or complementary to the nucleic acid molecule comprising the nucleotide sequence of SEQ ID NO: 1–3, 5, 26–28, or 30, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire coding strand, or to only a portion thereof. Nucleic acid molecules encoding fragments, homologs, derivatives and analogs of a protein of any of SEQ ID NO: 1–3, 5, 26–28, or 30 or antisense nucleic acids complementary to a nucleic acid sequence of SEQ ID NO: 1–3, 5, 26–28, or 30 are additionally provided.

In one embodiment, an antisense nucleic acid molecule is antisense to a "coding region" of the coding strand of a nucleotide sequence of the invention. The term "coding region" refers to the region of the nucleotide sequence comprising codons which are translated into amino acid residues. In another embodiment, the antisense nucleic acid molecule is antisense to a "noncoding region" of the coding strand of a nucleotide sequence of the invention. The term "noncoding region" refers to 5' and 3' sequences that flank the coding region that are not translated into amino acids (i.e., also referred to as 5' and 3' untranslated regions).

Given the coding strand sequences encoding a nucleic acid disclosed herein (e.g., SEQ ID NO: 1–3, 5, 26–28, or 30, antisense nucleic acids of the invention can be designed according to the rules of Watson and Crick or Hoogsteen base pairing. The antisense nucleic acid molecule can be complementary to the entire coding region of an mRNA, but more preferably is an oligonucleotide that is antisense to only a portion of the coding or noncoding region of an mRNA. For example, the antisense oligonucleotide can be complementary to the region surrounding the translation start site of an mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a protein according to the invention to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

5.4 Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave mRNA transcripts to thereby inhibit translation of an mRNA. A ribozyme having specificity for a nucleic acid of the invention can be designed based upon the nucleotide sequence of a DNA disclosed herein (i.e., SEQ ID NO: 1–3, 5, 26–28, or 30). For example, a derivative of Tetrahymena L-19 IVS RNA can be constructed in which the nucleotide sequence of the active site is complementary to the nucleotide sequence to be cleaved in a SECX-encoding mRNA. See, e.g., Cech et al. U.S. Pat. No. 4,987,071; and Cech et al. U.S. Pat. No. 5,116,742. Alternatively, SECX mRNA can be used to select a catalytic RNA having a specific ribonuclease activity from a pool of RNA molecules. See, e.g., Bartel et al., (1993) *Science* 261:1411–1418.

Alternatively, gene expression can be inhibited by targeting nucleotide sequences complementary to the regulatory region (e.g., promoter and/or enhancers) to form triple helical structures that prevent transcription of the gene in target cells. See generally, Helene. (1991) *Anticancer Drug Des.* 6: 569–84; Helene. et al. (1992) *Ann. N.Y. Acad. Sci.* 660:27–36; and Maher (1992) *Bioassays* 14: 807–15.

In various embodiments, the nucleic acids of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of the invention can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of the invention can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5' (4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5'PNA segment and a 3'DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

5.5 Hosts

The present invention further provides host cells genetically engineered to contain the polynucleoticles of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

Knowledge of alpha-2-macroglobulin-like DNA sequences allows for modification of cells to permit, or increase, expression of alpha-2-macroglobulin-like polypeptide. Cells can be modified (e.g., by homologous recombination) to provide increased alpha-2-macroglobulin-like polypeptide expression by replacing, in whole or in part, the naturally occurring alpha-2-macroglobulin-like promoter with all or part of a heterologous promoter so that the cells alpha-2-macroglobulin-like polypeptide is expressed at higher levels. The heterologous promoter is inserted in such a manner that it is operatively linked to alpha-2-macroglobulin-like encoding sequences. See, for example, PCT International Publication No. WO94/12650, PCT International Publication No. WO92/20808, and PCT International Publication No. WO91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the alpha-2-macroglobulin-like coding sequence, amplification of the marker DNA by standard selection methods results in co-amplification of the alpha-2-macroglobulin-like coding sequences in the cells.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran-mediated transfection, or electroporation (Davis, L. et al., Basic Methods in Molecular Biology (1986)). The host cells containing one of the polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, 293 cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981). Other cell lines capable of expressing a compatible vector are, for example, the C127, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

Alternatively, it may be possible to produce the protein in lower eukaryotes such as yeast or insects or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequence include polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

5.6 Polypeptides of the Invention

The isolated polypeptides of the invention include, but are not limited to, a polypeptide comprising: the amino acid sequence set forth as any one of SEQ ID NO: 4, 6–22, 25, 29, or 31–40 or an amino acid sequence encoded by any one of the nucleotide sequences SEQ ID NO: 1–3, 5, 26–28, or 30 or the corresponding full length or mature protein. Polypeptides of the invention also include polypeptides preferably with biological or immunological activity that are encoded by: (a) a polynucleotide having any one of the nucleotide sequences set forth in SEQ ID NO: 1–3, 5, 26–28, or 30 or (b) polynucleotides encoding any one of the amino acid sequences set forth as SEQ ID NO: 4, 6–22, 25, 29, or 31–40 or (c) polynucleotides that hybridize to the complement of the polynucleotides of either (a) or (b) under stringent hybridization conditions. The invention also provides biologically active or immunologically active variants of any of the amino acid sequences set forth as SEQ ID NO: 4, 6–22, 25, 29, or 31–40 or the corresponding full length or mature protein; and "substantial equivalents" thereof (e.g., with at least about 65%, at least about 70%, at least about 75%, at least about 80%, at least about 85%, at least about 90%, typically at least about 95%, more typically at least about 98%, or most typically at least about 99% amino acid identity) that retain biological activity. Polypeptides encoded by allelic variants may have a similar, increased, or decreased activity compared to polypeptides comprising SEQ ID NO: 4, 6–22, 25, 29, or 31–40.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites.

The present invention also provides both full-length and mature forms (for example, without a signal sequence or precursor sequence) of the disclosed proteins. The protein coding sequence is identified in the sequence listing by translation of the disclosed nucleotide sequences. The mature form of such protein may be obtained by expression of a full-length polynucleotide in a suitable mammalian cell or other host cell. The sequence of the mature form of the protein is also determinable from the amino acid sequence of the full-length form. Where proteins of the present invention are membrane bound, soluble forms of the proteins are also provided. In such forms, part or all of the regions causing the proteins to be membrane bound are deleted so that the proteins are fully secreted from the cell in which it is expressed.

Protein compositions of the present invention may further comprise an acceptable carrier, such as a hydrophilic, e.g., pharmaceutically acceptable, carrier.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

A variety of methodologies known in the art can be utilized to obtain any one of the isolated polypeptides or proteins of the present invention. At the simplest level, the amino acid sequence can be synthesized using commercially available peptide synthesizers. The synthetically-constructed protein sequences, by virtue of sharing primary, secondary or tertiary structural and/or conformational characteristics with proteins may possess biological properties in common therewith, including protein activity. This technique is particularly useful in producing small peptides and fragments of larger polypeptides. Fragments are useful, for example, in generating antibodies against the native polypeptide. Thus, they may be employed as biologically active or immunological substitutes for natural, purified proteins in screening of therapeutic compounds and in immunological processes for the development of antibodies.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The invention also relates to methods for producing a polypeptide comprising growing a culture of host cells of the invention in a suitable culture medium, and purifying the protein from the cells or the culture in which the cells are grown. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, or from a lysate prepared from the host cells and further purified. Preferred embodiments include those in which the protein produced by such process is a full length or mature form of the protein.

In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in Molecular Cloning: *A Laboratory Manual*; Ausubel et al., *Current Protocols in Molecular Biology*. Polypeptide fragments that retain biological/immunological activity include fragments comprising greater than about 100 amino acids, or greater than about 200 amino acids, and fragments that encode specific protein domains.

The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the peptides of the invention or molecules capable of binding to the peptides may be complexed with toxins, e.g., ricin or cholera, or with other compounds that are toxic to cells. The toxin-binding molecule complex is then targeted to a tumor or other cell by the specificity of the binding molecule for SEQ ID NO: 4, 6–22, 25, 29, or 31–40.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The proteins provided herein also include proteins characterized by amino acid sequences similar to those of purified proteins but into which modification are naturally provided or deliberately engineered. For example, modifications, in the peptide or DNA sequence, can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involved systematic substitution of single or strings of amino acids with alanine, followed by testing the resulting alanine-containing variant for biological activity. This type of analysis determines the importance of the substituted amino acid(s) in biological activity. Regions of the protein that are important for protein function may be determined by the eMATRIX program.

Other fragments and derivatives of the sequences of proteins which would be expected to retain protein activity in whole or in part and are useful for screening or other immunological methodologies may also be easily made by those skilled in the art given the disclosures herein. Such modifications are encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl™ or Cibacrom blue 3GA Sepharose™; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include analogs (variants). The polypeptides of the invention include alpha-2-macroglobulin-like analogs. This embraces fragments of alpha-2-macroglobulin-like polypeptides of the invention, as well alpha-2-macroglobulin-like polypeptides which comprise one or more amino acids deleted, inserted, or substituted. Also, analogs of the alpha-2-macroglobulin-like polypeptides of the invention embrace fusions of the alpha-2-macroglobulin-like polypeptides or modifications of the alpha-2-macroglobulin-like polypeptides, wherein the alpha-2-macroglobulin-like polypeptides or analogs are fused to another moiety or moieties, e.g., targeting moiety or another therapeutic agent. Such analogs may exhibit improved properties such as activity and/or stability. Examples of moieties which may be fused to the alpha-2-macroglobulin-like polypeptides or analogs include, for example, targeting moieties which provide for the delivery of polypeptide to neurons, e.g., antibodies to central nervous system, or antibodies to receptor and ligands expressed on neuronal cells. Other moieties which may be fused to alpha-2-macroglobulin-like polypeptides include therapeutic agents which are used for treatment, for example antidepressant drugs or other medications for neurological disorders. Also, alpha-2-macroglobulin-like polypeptides may be fused to neuron growth modulators, and other chemokines for targeted delivery.

5.6.1 Determining Polypeptide and Polynucleotide Identity and Similarity

Preferred identity and/or similarity are designed to give the largest match between the sequences tested. Methods to determine identity and similarity are codified in computer programs including, but are not limited to, the GCG program package, including GAP (Devereux, J., et al., Nucleic Acids Research 12(1):387 (1984); Genetics Computer Group, University of Wisconsin, Madison, Wis.), BLASTP, BLASTN, BLASTX, FASTA (Altschul, S. F. et al., J. Molec. Biol. 215:403–410 (1990), PSI-BLAST (Altschul S. F. et al., Nucleic Acids Res. vol. 25, pp. 3389–3402, herein incorporated by reference), the eMatrix software (Wu et al., J. Comp. Biol., vol. 6, pp. 219–235 (1999), herein incorporated by reference), eMotif software (Nevill-Manning et al, ISMB-97, vol 4, pp. 202–209, herein incorporated by reference), the GeneAtlas software (Molecular Simulations Inc. (MSI), San Diego, Calif.) (Sanchez and Sali (1998) Proc. Natl. Acad. Sci., 95, 13597–13602; Kitson D H et al, (2000) "Remote homology detection using structural modeling—an evaluation" Submitted; Fischer and Eisenberg (1996) Protein Sci. 5, 947–955), Neural Network SignalP V1.1 program (from Center for Biological Sequence Analysis, The Technical University of Denmark).and the Kyte-Doolittle hydrophobocity prediction algorithm (J. Mol Biol, 157, pp. 105–31 (1982), incorporated herein by reference). The BLAST programs are publicly available from the National Center for Biotechnology Information (NCBI) and other sources (BLAST Manual, Altschul, S., et al. NCB NLM NIH Bethesda, Md. 20894; Altschul, S., et al., J. Mol. Biol. 215:403–410 (1990).

5.7 Chimeric and Fusion Proteins

The invention also provides chimeric or fusion proteins. As used herein, a "chimeric protein" or "fusion protein" comprises a polypeptide of the invention operatively linked to another polypeptide. Within a fusion protein the polypeptide according to the invention can correspond to all or a portion of a protein according to the invention. In one embodiment, a fusion protein comprises at least one biologically active portion of a protein according to the invention. In another embodiment, a fusion protein comprises at least two biologically active portions of a protein according to the invention. Within the fusion protein, the term "operatively linked" is intended to indicate that the polypeptide according to the invention and the other polypeptide are fused in-frame to each other. The polypeptide can be fused to the N-terminus or C-terminus, or to the middle.

For example, in one embodiment a fusion protein comprises a polypeptide according to the invention operably linked to the extracellular domain of a second protein.

In another embodiment, the fusion protein is a GST-fusion protein in which the polypeptide sequences of the invention are fused to the C-terminus of the GST (i.e., glutathione S-transferase) sequences.

In another embodiment, the fusion protein is an immunoglobulin fusion protein in which the polypeptide sequences according to the invention comprise one or more domains fused to sequences derived from a member of the immunoglobulin protein family. The immunoglobulin fusion proteins of the invention can be incorporated into pharmaceutical compositions and administered to a subject to inhibit an interaction between a ligand and a protein of the invention on the surface of a cell, to thereby suppress signal transduction in vivo. The immunoglobulin fusion proteins can be used to affect the bioavailability of a cognate ligand. Inhibition of the ligand/protein interaction may be useful therapeutically for both the treatment of proliferative and differentiative disorders, e.g., cancer as well as modulating (e.g., promoting or inhibiting) cell survival. Moreover, the immunoglobulin fusion proteins of the invention can be used as immunogens to produce antibodies in a subject, to purify ligands, and in screening assays to identify molecules that inhibit the interaction of a polypeptide of the invention with a ligand.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the protein of the invention.

5.8 Gene Therapy

Mutations in the polynucleotides of the invention gene may result in loss of normal function of the encoded protein. The invention thus provides gene therapy to restore normal activity of the polypeptides of the invention; or to treat disease states involving polypeptides of the invention. Delivery of a functional gene encoding polypeptides of the invention to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp.25–20 (1998). For additional reviews of gene therapy technology see Friedmann, Science, 244: 1275–1281 (1989); Verma, Scientific American: 68–84 (1990); and Miller, Nature, 357: 455–460 (1992). Introduction of any one of the nucleotides of the present invention or a gene encoding the polypeptides of the present invention can also be accomplished with extrachromosomal substrates (transient expression) or artificial chromosomes (stable expression). Cells may also be cultured ex vivo in the presence of proteins of the present invention in order to proliferate or to produce a desired effect on or activity in such cells. Treated cells can then be introduced in vivo for therapeutic purposes. Alternatively, it is contemplated that in other human disease states, preventing the expression of or inhibiting the activity of polypeptides of the invention will be useful in treating the disease states. It is contemplated that antisense therapy or gene therapy could be applied to negatively regulate the expression of polypeptides of the invention.

Other methods inhibiting expression of a protein include the introduction of antisense molecules to the nucleic acids of the present invention, their complements, or their translated RNA sequences, by methods known in the art. Further, the polypeptides of the present invention can be inhibited by using targeted deletion methods, or the insertion of a negative regulatory element such as a silencer, which is tissue specific.

The present invention still further provides cells genetically engineered in vivo to express the polynucleotides of the invention, wherein such polynucleotides are in operative association with a regulatory sequence heterologous to the host cell which drives expression of the polynucleotides in the cell. These methods can be used to increase or decrease the expression of the polynucleotides of the present invention.

Knowledge of DNA sequences provided by the invention allows for modification of cells to permit, increase, or decrease, expression of endogenous polypeptide. Cells can be modified (e.g., by homologous recombination) to provide increased polypeptide expression by replacing, in whole or in part, the naturally occurring promoter with all or part of a heterologous promoter so that the cells express the protein at higher levels. The heterologous promoter is inserted in such a manner that it is operatively linked to the desired protein encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the desired protein coding sequence, amplification of the marker DNA by standard selection methods results in co-amplification of the desired protein coding sequences in the cells.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequences include polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

5.9 Transgenic Animals

In preferred methods to determine biological functions of the polypeptides of the invention in vivo, one or more genes provided by the invention are either over expressed or inactivated in the germ line of animals using homologous recombination [Capecchi, Science 244:1288–1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No. 5,489,743 and PCT Publication No. WO94/28122, incorporated herein by reference.

Transgenic animals can be prepared wherein all or part of a promoter of the polynucleotides of the invention is either activated or inactivated to alter the level of expression of the polypeptides of the invention. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

The polynucleotides of the present invention also make possible the development, through, e.g., homologous recombination or knock out strategies; of animals that fail to express functional alpha-2-macroglobulin-like polypeptide or that express a variant of alpha-2-macroglobulin-like polypeptide. Such animals are useful as models for studying the in vivo activities of alpha-2-macroglobulin-like polypeptide as well as for studying modulators of the alpha-2-macroglobulin-like polypeptide.

In preferred methods to determine biological functions of the polypeptides of the invention in vivo, one or more genes provided by the invention are either over expressed or inactivated in the germ line of animals using homologous recombination [Capecchi, Science 244:1288–1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably nonhuman mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No. 5,489,743 and PCT Publication No. WO94/28122, incorporated herein by reference.

Transgenic animals can be prepared wherein all or part of the polynucleotides of the invention promoter is either activated or inactivated to alter the level of expression of the polypeptides of the invention. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

5.10 Uses and Biological Activity of Human ALPHA-2-Macroglobulin-Like Polypeptide The polynucleotides and proteins of the present invention are expected to exhibit one or more of the uses or biological activities (including those associated with assays cited herein) identified herein. Uses or activities described for proteins of the present invention may be provided by administration or use of such proteins or of polynucleotides encoding such proteins (such as, for example, in gene therapies or vectors suitable for introduction of DNA). The mechanism underlying the particular condition or pathology will dictate whether the polypeptides of the invention, the polynucleotides of the invention or modulators (activators or inhibitors) thereof would be beneficial to the subject in need of treatment. Thus, "therapeutic compositions of the invention" include compositions comprising isolated polynucleotides (including recombinant DNA molecules, cloned genes and degenerate variants thereof) or polypeptides of the invention (including full length protein, mature protein and truncations or domains thereof), or compounds and other substances that modulate the overall activity of the target gene products, either at the level of target gene/protein expression or target protein activity. Such modulators include polypeptides, analogs, (variants), including fragments and fusion proteins, antibodies and other binding proteins; chemical compounds that directly or indirectly activate or inhibit the polypeptides of the invention (identified, e.g., via drug screening assays as described herein); antisense polynucleotides and polynucleotides suitable for triple helix formation; and in particular antibodies or other binding partners that specifically recognize one or more epitopes of the polypeptides of the invention.

The polypeptides of the present invention may likewise be involved in cellular activation or in one of the other physiological pathways described herein.

5.10.1 Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding polypeptide is preferentially expressed (either constitutively or at a particular stage of tissue differentiation or development or in a disease state); and, of course, to isolate correlative receptors or ligands. Proteins involved in these binding interactions can also be used to screen for peptide or small molecule inhibitors or agonists of the binding interaction.

The polypeptides of the invention are also useful for making antibody substances that are specifically immunoreactive with alpha-2-macroglobulin-like proteins. Antibodies and portions thereof (e.g., Fab fragments) which bind to the polypeptides of the invention can be used to identify the presence of such polypeptides in a sample. Such determinations are carried out using any suitable immunoassay format, and any polypeptide of the invention that is specifically bound by the antibody can be employed as a positive control.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

5.10.2 Nutritional Uses

Polynucleotides and polypeptides of the present invention can also be used as nutritional sources or supplements. Such uses include without limitation use as a protein or amino acid supplement, use as a carbon source, use as a nitrogen source and use as a source of carbohydrate. In such cases the polypeptide or polynucleotide of the invention can be added to the feed, of a particular organism or can be administered as a separate solid or liquid preparation, such as in the form of powder, pills, solutions, suspensions or capsules. In the case of microorganisms, the polypeptide or polynucleotide of the invention can be added to the medium in or on which the microorganism is cultured.

Additionally, the polypeptides of the invention can be used as molecular weight markers, and as a food supplement. A polypeptide consisting of SEQ ID NO: 4, for example, has a molecular mass of approximately 169 kDa in its unprocessed and unglycosylated state and a polypeptide consisting of SEQ ID NO: 29 has a molecular mass of approximately 102 kDa in its unprocessed and unglycosylated state. Protein food supplements are well known and the formulation of suitable food supplements including polypeptides of the invention is within the level of skill in the food preparation art.

5.10.3 Cytokine and Cell Proliferation/Differentiation Activity

A polypeptide of the present invention may exhibit activity relating to cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of therapeutic compositions of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e, CMK, HUVEC, and Caco. Therapeutic compositions of the invention can be used in the following:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., I. Immunol. 149:3778–3783, 1992; Bowman et al., I. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human interleukin-γ, Schreiber, R. D. In Current Protocols in Immunology. J. E. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. Coligan eds. Vol 1 pp. 6.6.1–6.6.5, John Wiley and Sons, Toronto. 1991; Smith et al., Proc. Natl. Aced. Sci. U.S.A. 83:1857–1861, 1986; Measurement of human Interleukin 11—Bennett, F., Giannotti, J., Clark, S. C. and Turner, K. J. In Current Protocols in Immunology. J. E. Coligan eds. Vol 1 pp. 6.15.1 John Wiley and Sons, Toronto. 1991; Measurement of mouse and human Interleukin 9-Ciarletta, A., Giannotti, J., Clark, S. C. and Turner, K. J. In Current Protocols in Immunology. J. E. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

5.10.4 Stem Cell Growth Factor Activity

A polypeptide of the present invention may exhibit stem cell growth factor activity and be involved in the proliferation, differentiation and survival of pluripotent and totipotent stem cells including primordial germ cells, embryonic stem cells, hematopoietic stem cells and/or germ line stem cells. Administration of the polypeptide of the invention to stem cells in vivo or ex vivo may maintain and expand cell populations in a totipotential or pluripotential state which would be useful for re-engineering damaged or diseased tissues, transplantation, manufacture of biopharmaceuticals and the development of bio-sensors. The ability to produce large quantities of human cells has important working applications for the production of human proteins which currently must be obtained from non-human sources or donors, implantation of cells to treat diseases such as Parkinson's, Alzheimer's and other neurodegenerative diseases; tissues for grafting such as bone marrow, skin, cartilage, tendons, bone, muscle (including cardiac muscle), blood vessels, cornea, neural cells, gastrointestinal cells and others; and organs for transplantation such as kidney, liver, pancreas (including islet cells), heart and lung.

It is contemplated that multiple different exogenous growth factors and/or cytokines may be administered in combination with the polypeptide of the invention to achieve the desired effect, including any of the growth factors listed herein, other stem cell maintenance factors, and specifically including stem cell factor (SCF), leukemia inhibitory factor (LIF), Flt-3 ligand (Flt-3L), any of the interleukins, recombinant soluble IL-6 receptor fused to IL-6, macrophage inflammatory protein 1-alpha (MIP-1-alpha), G-CSF, GM-CSF, thrombopoietin (TPO), platelet factor 4 (PF-4), platelet-derived growth factor (PDGF), neural growth factors and basic fibroblast growth factor (bFGF).

Since totipotent stem cells can give rise to virtually any mature cell type, expansion of these cells in culture will facilitate the production of large quantities of mature cells. Techniques for culturing stem cells are known in the art and administration of polypeptides of the invention, optionally with other growth factors and/or cytokines, is expected to enhance the survival and proliferation of the stem cell populations. This can be accomplished by direct administration of the polypeptide of the invention to the culture medium. Alternatively, stroma cells transfected with a polynucleotide that encodes for the polypeptide of the invention can be used as a feeder layer for the stem cell populations in culture or in vivo. Stromal support cells for feeder layers may include embryonic bone marrow fibroblasts, bone marrow stromal cells, fetal liver cells, or cultured embryonic fibroblasts (see U.S. Pat. No. 5,690,926).

Stem cells themselves can be transfected with a polynucleotide of the invention to induce autocrine expression of the polypeptide of the invention. This will allow for generation of undifferentiated totipotential/pluripotential stem cell lines that are useful as is or that can then be differentiated into the desired mature cell types. These stable cell lines can also serve as a source of undifferentiated totipotential/pluripotential mRNA to create cDNA libraries and templates for polymerase chain reaction experiments. These studies would allow for the isolation and identification of differentially expressed genes in stem cell populations that regulate stem cell proliferation and/or maintenance.

Expansion and maintenance of totipotent stem cell populations will be useful in the treatment of many pathological conditions. For example, polypeptides of the present invention may be used to manipulate stem cells in culture to give rise to neuroepithelial cells that can be used to augment or replace cells damaged by illness, autoimmune disease, accidental damage or genetic disorders. The polypeptide of the invention may be useful for inducing the proliferation of neural cells and for the regeneration of nerve and brain tissue, i.e. for the treatment of central and peripheral nervous system diseases and neuropathies, as well as mechanical and traumatic disorders which involve degeneration, death or trauma to neural cells or nerve tissue. In addition, the expanded stem cell populations can also be genetically altered for gene therapy purposes and to decrease host rejection of replacement tissues after grafting or implantation.

Expression of the polypeptide of the invention and its effect on stem cells can also be manipulated to achieve controlled differentiation of the stem cells into more differentiated cell types. A broadly applicable method of obtaining pure populations of a specific differentiated cell type from undifferentiated stem cell populations involves the use of a cell-type specific promoter driving a selectable marker. The selectable marker allows only cells of the desired type to survive. For example, stem cells can be induced to differentiate into cardiomyocytes (Wobus et al., Differentiation, 48: 173–182, (1991); Klug et al., J. Clin. Invest., 98(1): 216–224, (1998)) or skeletal muscle cells (Browder, L. W. In: *Principles of Tissue Engineering eds*. Lanza et al., Academic Press (1997)). Alternatively, directed differentiation of stem cells can be accomplished by culturing the stem cells in the presence of a differentiation factor such as retinoic acid and an antagonist of the polypeptide of the invention which would inhibit the effects of endogenous stem cell factor activity and allow differentiation to proceed.

In vitro cultures of stem cells can be used to determine if the polypeptide of the invention exhibits stem cell growth factor activity. Stem cells are isolated from any one of various cell sources (including hematopoietic stem cells and embryonic stem cells) and cultured on a feeder layer, as described by Thompson et al. Proc. Natl. Acad. Sci, U.S.A., 92: 7844–7848 (1995), in the presence of the polypeptide of the invention alone or in combination with other growth factors or cytokines. The ability of the polypeptide of the invention to induce stem cells proliferation is determined by colony formation on semi-solid support e.g. as described by Bernstein et al., Blood, 77: 2316–2321 (1991).

5.10.5 Hematopoiesis Regulating Activity

A polypeptide of the present invention may be involved in regulation of hematopoiesis and, consequently, in the treatment of myeloid or lymphoid cell disorders. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

Therapeutic compositions of the invention can be used in the following:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

5.10.6 Tissue Growth Activity

A polypeptide of the present invention also may be involved in bone, cartilage, tendon, ligament and/or nerve tissue growth or regeneration, as well as in wound healing and tissue repair and replacement, and in healing of burns, incisions and ulcers.

A polypeptide of the present invention which induces cartilage and/or bone growth in circumstances where bone is not normally formed, has application in the healing of bone fractures and cartilage damage or defects in humans and other animals. Compositions of a polypeptide, antibody, binding partner, or other modulator of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A polypeptide of this invention may also be involved in attracting bone-forming cells, stimulating growth of bone-forming cells, or inducing differentiation of progenitors of bone-forming cells. Treatment of osteoporosis, osteoarthritis, bone degenerative disorders, or periodontal disease, such as through stimulation of bone and/or cartilage repair or by blocking inflammation or processes of tissue destruction (collagenase activity, osteoclast activity, etc.) mediated by inflammatory processes may also be possible using the composition of the invention.

Another category of tissue regeneration activity that may involve the polypeptide of the present invention is tendon/ligament formation. Induction of tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The compositions of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a composition may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a composition of the invention.

Compositions of the invention may also be useful to promote better or faster closure of non-healing wounds, including without limitation pressure ulcers, ulcers associated with vascular insufficiency, surgical and traumatic wounds, and the like.

Compositions of the present invention may also be involved in the generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring may allow normal tissue to regenerate. A polypeptide of the present invention may also exhibit angiogenic activity.

A composition of the present invention may also be useful for gut protection or regeneration and treatment of lung or liver fibrosis, reperfusion injury in various tissues, and conditions resulting from systemic cytokine damage.

A composition of the present invention may also be useful for promoting or inhibiting differentiation of tissues described above from precursor tissues or cells; or for inhibiting the growth of tissues described above.

Therapeutic compositions of the invention can be used in the following:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pp. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

5.10.7 Immune Function Stimulating or Suppressing Activity

A polypeptide of the present invention may also exhibit immune stimulating or immune suppressing activity, including without limitation the activities for which assays are described herein. A polynucleotide of the invention can encode a polypeptide exhibiting such activities. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpes viruses, mycobacteria, Leishmania spp., malaria spp. and various fungal infections such as candidiasis. Of course, in this regard, proteins of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein (or antagonists thereof, including antibodies) of the present invention may also to be useful in the treatment of allergic reactions and conditions (e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies), such as asthma (particularly allergic asthma) or other respiratory problems. Other conditions, in which immune suppression is desired (including, for example, organ transplantation), may also be treatable using a protein (or antagonists thereof) of the present invention. The therapeutic effects of the polypeptides or antagonists thereof on allergic reactions can be evaluated by in vivo animals models such as the cumulative contact enhancement test (Lastbom et al., Toxicology 125: 59–66, 1998), skin prick test (Hoffmann et al., Allergy 54: 446–54, 1999), guinea pig skin sensitization test (Vohr et al., Arch. Toxocol. 73: 501–9), and murine local lymph node assay (Kimber et al., J. Toxicol. Environ. Health 53: 563–79).

Using the proteins of the invention it may also be possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a therapeutic composition of the invention may prevent cytokine synthesis by immune cells, such as T cells, and thus acts as an immunosuppressant. Moreover, a lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular therapeutic compositions in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of therapeutic compositions of the invention on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block stimulation of T cells can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (e.g., a B lymphocyte antigen function), as a means of up regulating immune responses, may also be useful in therapy. Upregulation of immune responses may be in the form of enhancing an existing immune response or eliciting an initial immune response. For example, enhancing an immune response may be useful in cases of viral infection, including systemic viral diseases such as influenza, the common cold, and encephalitis.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

A polypeptide of the present invention may provide the necessary stimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I alpha chain protein and $\beta_2$ microglobulin protein or an MHC class II alpha chain protein and an MHC class II beta chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., I. Immunol. 137:3494–3500, 1986; Takai et al., J. Immunol. 140:508–512, 1988; Bowman et al., J. Virology 61:1992–1998; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad. Sci. USA 88:7548–7551, 1991.

5.10.8 Activin/Inhibin Activity

A polypeptide of the present invention may also exhibit activin- or inhibin-related activities. A polynucleotide of the invention may encode a polypeptide exhibiting such characteristics. Inhibins are characterized by their ability to inhibit the release of follicle stimulating hormone (FSH), while activins and are characterized by their ability to stimulate the release of follicle stimulating hormone (FSH). Thus, a polypeptide of the present invention, alone or in heterodimers with a member of the inhibin family, may be useful as a contraceptive based on the ability of inhibins to decrease fertility in female mammals and decrease spermatogenesis in male mammals. Administration of sufficient amounts of other inhibins can induce infertility in these mammals. Alternatively, the polypeptide of the invention, as a homodimer or as a heterodimer with other protein subunits of the inhibin group, may be useful as a fertility inducing therapeutic, based upon the ability of activin molecules in stimulating FSH release from cells of the anterior pituitary. See, for example, U.S. Pat. No. 4,798,885. A polypeptide of the invention may also be useful for advancement of the onset of fertility in sexually immature mammals, so as to increase the lifetime reproductive performance of domestic animals such as, but not limited to, cows, sheep and pigs.

The activity of a polypeptide of the invention may, among other means, be measured by the following methods.

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

5.10.9 Chemotactic/Chemokinetic Activity

A polypeptide of the present invention may be involved in chemotactic or chemokinetic activity for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic receptor activation can be used to mobilize or attract a desired cell population to a desired site of action. Chemotactic or chemokinetic compositions (e.g. proteins, antibodies, binding partners, or modulators of the invention) provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

Therapeutic compositions of the invention can be used in the following:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153:1762–1768, 1994.

5.10.10 Hemostatic and Thrombolytic Activity

A polypeptide of the invention may also be involved in hemostatis or thrombolysis or thrombosis. A polynucleotide of the invention can encode a polypeptide exhibiting such attributes. Compositions may be useful in treatment of various coagulation disorders (including hereditary disorders, such as hemophilias) or to enhance coagulation and other hemostatic events in treating wounds resulting from trauma, surgery or other causes. A composition of the invention may also be useful for dissolving or inhibiting formation of thromboses and for treatment and prevention of conditions resulting therefrom (such as, for example, infarction of cardiac and central nervous system vessels (e.g., stroke).

Therapeutic compositions of the invention can be used in the following:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

5.10.11 Cancer Diagnosis and Therapy

Polypeptides of the invention may be involved in cancer cell generation, proliferation or metastasis. Detection of the presence or amount of polynucleotides or polypeptides of the invention may be useful for the diagnosis and/or prognosis of one or more types of cancer. For example, the presence or increased expression of a polynucleotide/polypeptide of the invention may indicate a hereditary risk of cancer, a precancerous condition, or an ongoing malignancy. Conversely, a defect in the gene or absence of the polypeptide may be associated with a cancer condition. Identification of single nucleotide polymorphisms associated with cancer or a predisposition to cancer may also be useful for diagnosis or prognosis.

Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. Therapeutic compositions of the invention may be effective in adult and pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma.

Polypeptides, polynucleotides, or modulators of polypeptides of the invention (including inhibitors and stimulators of the biological activity of the polypeptide of the invention) may be administered to treat cancer. Therapeutic compositions can be administered in therapeutically effective dosages alone or in combination with adjuvant cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer.

The composition can also be administered in therapeutically effective amounts as a portion of an anti-cancer cocktail. An anti-cancer cocktail is a mixture of the polypeptide or modulator of the invention with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the polypeptide or modulator of the invention include: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16–213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

In addition, therapeutic compositions of the invention may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of the polypeptide of the invention to reduce the risk of developing cancers.

In vitro models can be used to determine the effective doses of the polypeptide of the invention as a potential cancer treatment. These in vitro models include proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921–30 (1974), mobility and invasive potential of tumor cells in Boyden Chamber assays as described in Pilkington et al., Anticancer Res., 17: 4107–9 (1997), and angiogenesis assays such as induction of vascularization of the chick chorioallantoic membrane or induction of vascular endothelial cell migration as described in Ribatta et al., Intl. J. Dev. Biol., 40: 1189–97 (1999) and Li et al., Clin. Exp. Metastasis, 17:423–9 (1999), respectively. Suitable tumor cells lines are available, e.g. from American Type Tissue Culture Collection catalogs.

5.10.12 Receptor/Ligand Activity

A polypeptide of the present invention may also demonstrate activity as receptor, receptor ligand or inhibitor or agonist of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses. Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a polypeptide of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

By way of example, the polypeptides of the invention may be used as a receptor for a ligand(s) thereby transmitting the biological activity of that ligand(s). Ligands may be identified through binding assays, affinity chromatography, dihybrid screening assays, BIAcore assays, gel overlay assays, or other methods known in the art.

Studies characterizing drugs or proteins as agonist or antagonist or partial agonists or a partial antagonist require the use of other proteins as competing ligands. The polypeptides of the present invention or ligand(s) thereof may be labeled by being coupled to radioisotopes, colorimetric molecules or a toxin molecules by conventional methods. ("Guide to Protein Purification" Murray P. Deutscher (ed) Methods in Enzymology Vol. 182 (1990) Academic Press, Inc. San Diego). Examples of radioisotopes include, but are not limited to, tritium and carbon-14. Examples of colorimetric molecules include, but are not limited to, fluorescent molecules such as fluorescamine, or rhodamine or other calorimetric molecules. Examples of toxins include, but are not limited, to ricin.

5.10.13 Drug Screening

This invention is particularly useful for screening chemical compounds by using the novel polypeptides or binding fragments thereof in any of a variety of drug screening techniques. The polypeptides or fragments employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or a fragment thereof. Drugs are screened against such transformed cells in competitive binding assays. Such cells, either in viable or fixed form, can be used for standard binding assays. One may measure, for example, the formation of complexes between polypeptides of the invention or fragments and the agent being tested or examine the diminution in complex formation between the novel polypeptides and an appropriate cell line, which are well known in the art.

Sources for test compounds that may be screened for ability to bind to or modulate (i.e., increase or decrease) the activity of polypeptides of the invention include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see *Science* 282:63–68 (1998).

Combinatorial libraries are composed of large numbers of peptides, oligonucleotides, or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701–707

(1997). For reviews and examples of peptidomimetic libraries, see Al-Obeidi et al., *Mol. Biotechnol*, 9(3):205–23 (1998); Hruby et al., *Curr Opin Chem Biol*, 1(1):114–19 (1997); Dorner et al., *Bioorg Med Chem*, 4(5):709–15 (1996) (alkylated dipeptides).

Identification of modulators through use of the various libraries described herein permits modification of the candidate "hit" (or "lead") to optimize the capacity of the "hit" to bind a polypeptide of the invention. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

The binding molecules thus identified may be complexed with toxins, e.g., ricin or cholera, or with other compounds that are toxic to cells such as radioisotopes. The toxin-binding molecule complex is then targeted to a tumor or other cell by the specificity of the binding molecule for a polypeptide of the invention. Alternatively, the binding molecules may be complexed with imaging agents for targeting and imaging purposes.

5.10.14 Assay for Receptor Activity

The invention also provides methods to detect specific binding of a polypeptide e.g. a ligand or a receptor. The art provides numerous assays particularly useful for identifying previously unknown binding partners for receptor polypeptides of the invention. For example, expression cloning using mammalian or bacterial cells, or dihybrid screening assays can be used to identify polynucleotides encoding binding partners. As another example, affinity chromatography with the appropriate immobilized polypeptide of the invention can be used to isolate polypeptides that recognize and bind polypeptides of the invention. There are a number of different libraries used for the identification of compounds, and in particular small molecule, that modulate (i.e., increase or decrease) biological activity of a polypeptide of the invention. Ligands for receptor polypeptides of the invention can also be identified by adding exogenous ligands, or cocktails of ligands to two cells populations that are genetically identical except for the expression of the receptor of the invention: one cell population expresses the receptor of the invention whereas the other does not. The response of the two cell populations to the addition of ligands(s) is then compared. Alternatively, an expression library can be co-expressed with the polypeptide of the invention in cells and assayed for an autocrine response to identify potential ligand(s). As still another example, BIAcore assays, gel overlay assays, or other methods known in the art can be used to identify binding partner polypeptides, including, (1) organic and inorganic chemical libraries, (2) natural product libraries, and (3) combinatorial libraries comprised of random peptides, oligonucleotides or organic molecules.

The role of downstream intracellular signaling molecules in the signaling cascade of the polypeptide of the invention can be determined. For example, a chimeric protein in which the cytoplasmic domain of the polypeptide of the invention is fused to the extracellular portion of a protein, whose ligand has been identified, is produced in a host cell. The cell is then incubated with the ligand specific for the extracellular portion of the chimeric protein, thereby activating the chimeric receptor. Known downstream proteins involved in intracellular signaling can then be assayed for expected modifications i.e. phosphorylation. Other methods known to those in the art can also be used to identify signaling molecules involved in receptor activity.

5.10.15 Anti-Inflammatory Activity

Compositions of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Compositions with such activities can be used to treat inflammatory conditions including chronic or acute conditions, including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Compositions of the invention may also be useful to treat anaphylaxis and hypersensitivity to an antigenic substance or material. Compositions of this invention may be utilized to prevent or treat conditions such as, but not limited to, sepsis, acute pancreatitis, endotoxin shock, cytokine induced shock, rheumatoid arthritis, chronic inflammatory arthritis, pancreatic cell damage from diabetes mellitus type 1, graft versus host disease, inflammatory bowel disease, inflamation associated with pulmonary disease, other autoimmune disease or inflammatory disease, an antiproliferative agent such as for acute or chronic mylegenous leukemia or in the prevention of premature labor secondary to intrauterine infections.

5.10.16 Leukemias

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, Medicine, 2d Ed., J. B. Lippincott Co., Philadelphia).

5.10.17 Nervous System Disorders

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(iv) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(v) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vi) neurological lesions associated with systemic diseases including but not limited to diabetes (diabetic neuropathy, Bell's palsy), systemic lupus erythematosus, carcinoma, or sarcoidosis;

(vii) lesions caused by toxic substances including alcohol, lead, or particular neurotoxins; and (viii) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.10.18 Other Activities

A polypeptide of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, collecting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

5.10.19 Identification of Polymorphisms

The demonstration of polymorphisms makes possible the identification of such polymorphisms in human subjects and the pharmacogenetic use of this information for diagnosis and treatment. Such polymorphisms may be associated with, e.g., differential predisposition or susceptibility to various disease states (such as disorders involving inflammation or immune response) or a differential response to drug administration, and this genetic information can be used to tailor preventive or therapeutic treatment appropriately. For example, the existence of a polymorphism associated with a predisposition to inflammation or autoimmune disease makes possible the diagnosis of this condition in humans by identifying the presence of the polymorphism.

Polymorphisms can be identified in a variety of ways known in the art which all generally involve obtaining a sample from a patient, analyzing DNA from the sample, optionally involving isolation or amplification of the DNA, and identifying the presence of the polymorphism in the DNA. For example, PCR may be used to amplify an appropriate fragment of genomic DNA which may then be sequenced. Alternatively, the DNA may be subjected to allele-specific oligonucleotide hybridization (in which appropriate oligonucleotides are hybridized to the DNA under conditions permitting detection of a single base mismatch) or to a single nucleotide extension assay (in which an oligonucleotide that hybridizes immediately adjacent to the position of the polymorphism is extended with one or more labeled nucleotides). In addition, traditional restriction fragment length polymorphism analysis (using restriction enzymes that provide differential digestion of the genomic DNA depending on the presence or absence of the polymorphism) may be performed. Arrays with nucleotide sequences of the present invention can be used to detect polymorphisms. The array can comprise modified nucleotide sequences of the present invention in order to detect the nucleotide sequences of the present invention. In the alternative, any one of the nucleotide sequences of the present invention can be placed on the array to detect changes from those sequences.

Alternatively a polymorphism resulting in a change in the amino acid sequence could also be detected by detecting a corresponding change in amino acid sequence of the protein, e.g., by an antibody specific to the variant sequence.

5.10.20 Arthritis and Inflammation

The immunosuppressive effects of the compositions of the invention against rheumatoid arthritis is determined in an experimental animal model system. The experimental model system is adjuvant induced arthritis in rats, and the protocol is described by J. Holoshitz, et al., 1983, Science, 219:56, or by B. Waksman et al., 1963, Int. Arch. Allergy Appl. Immunol., 23:129. Induction of the disease can be caused by a single injection, generally intradermally, of a suspension of killed *Mycobacterium tuberculosis* in complete Freund's adjuvant (CFA). The route of injection can vary, but rats may be injected at the base of the tail with an adjuvant mixture. The polypeptide is administered in phosphate buffered solution (PBS) at a dose of about 1–5 mg/kg. The control consists of administering PBS only.

The procedure for testing the effects of the test compound would consist of intradermally injecting killed *Mycobacterium tuberculosis* in CFA followed by immediately administering the test compound and subsequent treatment every other day until day 24. At 14, 15, 18, 20, 22, and 24 days after injection of Mycobacterium CFA, an overall arthritis score may be obtained as described by J. Holoskitz above. An analysis of the data would reveal that the test compound would have a dramatic affect on the swelling of the joints as measured by a decrease of the arthritis score.

5.11 Therapeutic Methods

The compositions (including polypeptide fragments, analogs, variants and antibodies or other binding partners or modulators including antisense polynucleotides) of the invention have numerous applications in a variety of therapeutic methods. Examples of therapeutic applications include, but are not limited to, those exemplified herein.

5.11.1 Example

One embodiment of the invention is the administration of an effective amount of the alpha-2-macroglobulin-like polypeptides or other composition of the invention to individuals affected by a disease or disorder that can be modulated by regulating the peptides of the invention. While the mode of administration is not particularly important, parenteral administration is preferred. An exemplary mode of administration is to deliver an intravenous bolus. The dosage of alpha-2-macroglobulin-like polypeptides or other composition of the invention will normally be determined by the prescribing physician. It is to be expected that the dosage will vary according to the age, weight, condition and response of the individual patient. Typically, the amount of polypeptide administered per dose will be in the range of about 0.01 μg/kg to 100 mg/kg of body weight, with the preferred dose being about 0.1 μg/kg to 10 mg/kg of patient body weight. For parenteral administration, alpha-2-macroglobulin-like polypeptides of the invention will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the polypeptide or other active ingredient. The preparation of such solutions is within the skill of the art.

5.12 Pharmaceutical Formulations and Routes of Administration

A protein or other composition of the present invention (from whatever source derived, including without limitation from recombinant and non-recombinant sources and including antibodies and other binding partners of the polypeptides of the invention) may be administered to a patient in need, by itself, or in pharmaceutical compositions where it is mixed with suitable carriers or excipient(s) at doses to treat or ameliorate a variety of disorders. Such a composition may optionally contain (in addition to protein or other active ingredient and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. In further compositions, proteins of the invention may be combined with other agents beneficial to the treatment of the disease or disorder in question. These agents include various growth factors such as epidermal growth factor (EGF), platelet-derived growth factor (PDGF), transforming growth factors (TGF-α and TGF-β), insulin-like growth factor (IGF), as well as cytokines described herein.

The pharmaceutical composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects. Conversely, protein or other active ingredient of the present invention may be included in formulations of the particular clotting factor, cytokine, lymphokine, other hematopoietic factor, thrombolytic or anti-thrombotic factor, or anti-inflammatory agent to minimize side effects of the clotting factor, cytokine, lymphokine, other hematopoietic factor, thrombolytic or anti-thrombotic factor, or anti-inflammatory agent (such as IL-1Ra, IL-1Hy1, IL-1Hy2, anti-TNF, corticosteroids, immunosuppressive agents). A protein of the present invention may be active in multimers (e.g., heterodimers or homodimers) or complexes with itself or other proteins. As a result, pharmaceutical compositions of the invention may comprise a protein of the invention in such multimeric or complexed form.

As an alternative to being included in a pharmaceutical composition of the invention including a first protein, a second protein or a therapeutic agent may be concurrently administered with the first protein (e.g., at the same time, or at differing times provided that therapeutic concentrations of the combination of agents is achieved at the treatment site). Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein or other active ingredient of the present invention is administered to a mammal having a condition to be treated. Protein or other active ingredient of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein or other active ingredient of the present invention may be administered either simultaneously with the cytokine(s), lymphokine(s), other hematopoietic factor (s), thrombolytic or anti-thrombotic factors, or sequentially. If administered sequentially, the attending physician will decide on the appropriate sequence of administering protein or other active ingredient of the present invention in combination with cytokine(s), lymphokine(s), other hematopoietic factor(s), thrombolytic or anti-thrombotic factors.

5.12.1 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein or other active ingredient of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

The polypeptides of the invention are administered by any route that delivers an effective dosage to the desired site of action. The determination of a suitable route of administration and an effective dosage for a particular indication is within the level of skill in the art. Preferably for wound treatment, one administers the therapeutic compound directly to the site. Suitable dosage ranges for the polypeptides of the invention can be extrapolated from these dosages or from similar studies in appropriate animal models. Dosages can then be adjusted as necessary by the clinician to provide maximal therapeutic benefit.

5.12.2 Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein or other active ingredient of the present invention is administered orally, protein or other active ingredient of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein or other active ingredient of the present invention, and preferably from about 25 to 90% protein or other active ingredient of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein or other active ingredient of the present invention, and preferably from about 1 to 50% protein or other active ingredient of the present invention.

When a therapeutically effective amount of protein or other active ingredient of the present invention is administered by intravenous, cutaneous or subcutaneous injection, protein or other active ingredient of the present invention will be in the form of a pyrogen-free, parenterally acceptable aqueous solution. The preparation of such parenterally acceptable protein or other active ingredient solutions, having due regard to pH, isotonicity, stability, and the like, is within the skill in the art. A preferred pharmaceutical composition for intravenous, cutaneous, or subcutaneous injection should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrroli done, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin For use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with pharmaceutically compatible counter ions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) or other active ingredient of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein or other active ingredient of the present invention in the pharmaceutical composition of the present invention will depend upon the nature and severity of the condition being treated, and on the nature of prior treatments which the patient has undergone. Ultimately, the attending physician will decide the amount of protein or other active ingredient of the present invention with which to treat each individual patient. Initially, the attending physician will administer low doses of protein or other active ingredient of the present invention and observe the patient's response. Larger doses of protein or other active ingredient of the present invention may be administered until the optimal therapeutic effect is obtained for the patient, and at that point the dosage is not increased further. It is contemplated that the various pharmaceutical compositions used to practice the method of the present invention should contain about 0.01 μg to about 100 mg (preferably about 0.1 μg to about 10 mg, more preferably about 0.1 μg to about 1 mg) of protein or other active ingredient of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein or other active ingredient of the invention which may also optionally be included in the composition as described above, may alternatively or additionally, be administered simultaneously or sequentially with the composition in the methods of the invention. Preferably for bone and/or cartilage Formation, the composition would include a matrix capable of delivering the protein-containing or other active ingredient-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropylmethylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorption of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins or other active ingredient of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins or other active ingredient of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

5.12.3 Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amount is well within the capability of those skilled in the art, especially in light of the detailed disclosure provided herein. For any compound used in the method of the invention, the therapeutically effective dose can be estimated initially from appropriate in vitro assays. For example, a dose can be formulated in animal models to achieve a circulating concentration range that can be used to more accurately determine useful doses in humans. For example, a dose can be formulated in animal models to achieve a circulating concentration range that includes the $IC_{50}$ as determined in cell culture (i.e., the concentration of the test compound which achieves a half-maximal inhibition of the protein's biological activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1. Dosage amount and interval may be adjusted individually to provide plasma levels of the active moiety which are sufficient to maintain the desired effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

An exemplary dosage regimen for polypeptides or other compositions of the invention will be in the range of about 0.01 µg/kg to 100 mg/kg of body weight daily, with the preferred dose being about 0.1 µg/kg to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

5.12.4 Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

5.13 Antibodies

Also included in the invention are antibodies to proteins, or fragments of proteins of the invention. The term "antibody" as used herein refers to immunoglobulin molecules and immunologically active portions of immunoglobulin (Ig) molecules, i.e., molecules that contain an antigen-binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO: 4, 6–22, 25, 29, or 31–40, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of alpha-2-macroglobulin-like protein that is located on the surface of the protein, e.g., a hydrophilic region. A hydrophobicity analysis of the human related protein sequence will indicate which regions of a related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

The term "specific for" indicates that the variable regions of the antibodies of the invention recognize and bind polypeptides of the invention exclusively (i.e., able to distinguish the polypeptide of the invention from other similar polypeptides despite sequence identity, homology, or similarity found in the family of polypeptides), but may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the polypeptides of the invention are also contemplated, provided that the antibodies are first and foremost specific for, as defined above, full-length polypeptides of the invention. As with antibodies that are specific for full length polypeptides of the invention, antibodies of the invention that recognize fragments are those which can distinguish polypeptides from the same family of polypeptides despite inherent sequence identity, homology, or similarity found in the family of proteins.

Antibodies of the invention are useful for, for example, therapeutic purposes (by modulating activity of a polypeptide of the invention), diagnostic purposes to detect or quantitate a polypeptide of the invention, as well as purification of a polypeptide of the invention. Kits comprising an antibody of the invention for any of the purposes described herein are also comprehended. In general, a kit of the invention also includes a control antigen for which the antibody is immunospecific. The invention further provides a hybridoma that produces an antibody according to the invention. Antibodies of the invention are useful for detection and/or purification of the polypeptides of the invention.

Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and Sepharose®, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

5.13.1 Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface-active substances (e.g., lysolecithin, pluronic polyols, polyanions, peptides, oil emulsions, dinitrophenol, etc.), adjuvants usable in humans such as Bacille Calmette-Guerin and *Corynebacterium* parvum, or similar immunostimulatory agents. Additional examples of adjuvants that can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

5.13.2 Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen-binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

5.13.3 Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', $F(ab')_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., Nature, 321:522–525 (1986); Riechmann et al., Nature, 332:323–327 (1988); Verhoeyen et al., Science, 239:1534–1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, Curr. Op. Struct. Biol., 2:593–596 (1992)).

5.13.4 Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10, 779–783 (1992)); Lonberg et al. (Nature 368 856–859 (1994)); Morrison (Nature 368, 812–13 (1994)); Fishwild et al, (Nature Biotechnology 14, 845–51 (1996)); Neuberger (Nature Biotechnology 14, 826 (1996)); and Lonberg and Huszar (Intern. Rev. Immunol. 13 65–93 (1995)).

Human antibodies may additionally be produced using transgenic nonhuman animals that are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

5.13.5 FAB Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275–1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an Fab fragment generated by reducing the disulfide bridges of an $F_{(ab')2}$ fragment; (iii) an Fab fragment generated by the treatment of the antibody molecule with papain and a reducing agent and (iv) $F_v$ fragments.

5.13.6 Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., 1991 EMBO J., 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers that are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217–225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

5.13.7 Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

5.13.8 Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell filling and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et al., Anti-Cancer Drug Design, 3: 219–230 (1989).

5.13.9 Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

5.14 Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing any of the nucleotide sequences SEQ ID NO: 1–3, 5, 26–28, or 30 or a representative fragment thereof; or a nucleotide sequence at least 95% identical; or more preferably at least 98% identical, to any of the nucleotide sequences of SEQ ID NO: 1–3, 5, 26–28, or 30 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brutlag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, Smith-Waterman, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids, or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

5.15 Triple Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself (antisense—Olmno, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

5.16 Diagnostic Assays and Kits

The present invention further provides methods to identify the presence or expression of one of the ORFs of the present invention, or homolog thereof, in a test sample, using a nucleic acid probe or antibodies of the present invention, optionally conjugated or otherwise associated with a suitable label.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of the nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

5.17 Medical Imaging

The novel polypeptides and binding partners of the invention are useful in medical imaging of sites expressing the molecules of the invention (e.g., where the polypeptide of the invention is involved in the immune response, for imaging sites of inflammation or infection). See, e.g., Kunkel et al., U.S. Pat. No. 5,413,778. Such methods involve chemical attachment of a labeling or imaging agent, administration of the labeled polypeptide to a subject in a pharmaceutically acceptable carrier, and imaging the labeled polypeptide in vivo at the target site.

5.18 Screening Assays

Using the isolated proteins and polynucleotides of the invention, the present invention further provides methods of obtaining and identifying agents which bind to a polypeptide encoded by an ORF corresponding to any of the nucleotide sequences set forth in SEQ ID NO: 1–3, 5, 26–28, or 30, or bind to a specific domain of the polypeptide encoded by the nucleic acid. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polypeptide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like, capable of binding to a specific peptide sequence, in order to generate rationally designed antipeptide peptides, for example see Hurby et al., Application of Synthetic Peptides: Antisense Peptides," In Synthetic Peptides, A User's Guide, W. H. Freeman, NY (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while anti-sense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents that bind to a protein encoded by one of the ORFs of the present invention can be used as a diagnostic agent. Agents which bind to a protein encoded by one of the ORFs of the present invention can be formulated using known techniques to generate a pharmaceutical composition.

5.19 Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from any of the nucleotide sequences SEQ ID NO: 1–3, 5, 26–28, or 30. Because the corresponding gene is only expressed in a limited number of tissues, a hybridization probe derived from of any of the nucleotide sequences SEQ ID NO: 1–3, 5, 26–28, or 30 can be used as an indicator of the presence of RNA of cell type of such a tissue in a sample.

Any suitable hybridization technique can be employed, such as, for example, in situ hybridization. PCR as described in U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

5.20 Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved using passive adsorption (Inouye & Hondo, 1990 J. Clin Microbiol 28(6) 1462–72); using UV light (Nagata et al., 1985; Dahlen et al., 1987; Morrissey & Collins, Mol. Cell Probes 1989 3(2) 189–207) or by covalent binding of base modified DNA (Keller et al., 1988; 1989); all references being specifically incorporated herein.

Another strategy that may be employed is the use of the strong biotin-streptavidin interaction as a linker. For example, Broude et al. (1994) Proc. Natl. Acad. Sci USA 91(8) 3072–6 describe the use of biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond, allowing immobilization of more than 1 pmol of DNA (Rasmussen et al., (1991) Anal Biochem 198(1) 138–42.

The use of CovaLink NH strips for covalent binding of DNA molecules at the 5'-end has been described (Rasmussen et al., 1991). In this technology, a phosphoramidate bond is employed (Chu et al., 1983 Nucleic Acids 11(18) 6513–29). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/ul) and denaturing for 10 min. at 95° C. and cooling on ice for 10 min. Ice-cold 0.1 M 1-methylimidazole, pH 7.0 (1-MeIm$_7$), is then added to a final concentration of 10 MM 1-MeIm$_7$. A ss DNA solution is then dispensed into Covalink NH strips (75 ul/well) standing on ice.

Carbodiimide 0.2 M 1-ethyl-3-(3-dimethylaminopropyl)-carbodiimide (EDC), dissolved in 10 mM 1-MeIm$_7$, is made fresh and 25 ul added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (where in the washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991) Science 251(4995) 767–73, incorporated herein by reference. Probes may also be immobilized on nylon supports as described by Van Ness et al. (1991) Nucleic Acids Res. 19(12) 3345–50; or linked to Teflon using the method of Duncan & Cavalier (1988) Anal Biochem 169(1) 104–8; all references being specifically incorporated herein.

To link an oligonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucleotides is to utilize the light-generated synthesis described by Pease et al., (1994) Proc. Natl. Acad. Sci USA 91(11) 5022–6. These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5' protected N-acyl-deoxynucleoside phosphoramidites, surface linker chemistry and versatile combinatorial synthesis strategies. A matrix of 256 spatially defined oligonucleotide probes may be generated in this manner.

5.21 Preparation of Nucleic Acid Fragments

The nucleic acids may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14–9.23).

DNA fragments may be prepared as clones in M13, plasmid or lambda vectors and/or prepared directly from genomic DNA or cDNA by PCR or other amplification methods. Samples may be prepared or dispensed in multi-well plates. About 100–1000 ng of DNA samples may be prepared in 2–500 ml of final volume.

The nucleic acids would then be fragmented by any of the methods known to those of skill in the art including, for example, using restriction enzymes as described at 9.24–9.28 of Sambrook et al. (1989), shearing by ultrasound and NaOH treatment.

Low pressure shearing is also appropriate, as described by Schriefer et al. (1990) Nucleic Acids Res. 18(24) 7455–6. In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992) Nucleic Acids Res. 20(14) 3753–62. These authors described an approach for the rapid fragmentation and fractionation of DNA into particular sizes that they contemplated to be suitable for shotgun cloning and sequencing.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2–0.5 ug instead of 2–5 ug); and fewer steps are involved (no preligation, end repair, chemical extraction, or agarose gel electrophoresis and elution are needed).

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip. Phosphate groups must also be removed from genomic DNA by methods known in the art.

5.22 Preparation of DNA Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 $mm^2$, depending on the type of label used. By avoiding spotting in some preselected number of rows and columns, separate subsets (subarrays) may be formed. Samples in one subarray may be the same genomic segment of DNA (or the same gene) from different individuals, or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 $mm^2$ and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples. The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

6.0 EXAMPLES

Example 1

Isolation of SEQ ID NO: 1 from a cDNA Library of Fetal brain and SEQ ID NO: 26 from a cDNA Library of Uterus A plurality of novel nucleic acids were obtained from a cDNA library prepared from fetal brain mRNA (Clontech) (SEQ ID NO: 1) and uterus mRNA (Clontech) (SEQ ID NO: 26) using standard PCR, sequencing by hybridization sequence signature analysis, and Sanger sequencing techniques. The inserts of the library were amplified with PCR using primers specific for vector sequences flanking the inserts. These samples were spotted onto nylon membranes and interrogated with oligonucleotide probes to give sequence signatures. The clones were clustered into groups of similar or identical sequences, and single representative clones were selected from each group for gel sequencing. The 5' sequence of the amplified inserts was then deduced using the reverse M13 sequencing primer in a typical Sanger sequencing protocol. PCR products were purified and subjected to fluorescent dye terminator cycle sequencing. Single-pass gel sequencing was done using a 377 Applied Biosystems (ABI) sequencer. The inserts were identified as novel sequences not previously obtained from this library and not previously reported in public databases. The sequences were designated as SEQ ID NO: 1 and 26.

Example 2

Assemblage of SEQ ID NO: 2

The nucleic acid of the present invention, designated as SEQ ID NO: 2 was assembled using SEQ ID NO: 1 as a seed. Then a recursive algorithm was used to extend the seed into an extended assemblage, by pulling additional sequences from different databases (i.e., HIyseq's database containing EST sequences, dbEST version 114, gb pri 114, and UniGene version 101) that belong to this assemblage. The algorithm terminated when there was no additional sequences from the above databases that would extend the assemblage. Inclusion of component sequences into the assemblage was based on a BLASTN hit to the extending assemblage with BLAST score greater than 300 and percent identity greater than 95%.

The nearest neighbor result for the assembled contigs were obtained by a FASTA version 3 search against Genpept release 114, using FASTXY algorithm. FASTXY is an improved version of FASTA alignment which allows in-codon frame shifts. The nearest neighbor result showed the closest homologue for each assemblage from Genpept (and contains the translated amino acid sequences for which the assemblage encodes). The nearest neighbor results is set forth below:

| SEQ ID NO: | Accession No. | Description | Smith-Waterman Score | % Identity |
|---|---|---|---|---|
| 2 | D84338 | Cavia porcellus alpha-macroglobulin | 513 | 42.442 |

The nucleic acid of the present invention, designated as SEQ ID NO: 27 was assembled using SEQ ID NO: 26 as a seed. Then a recursive algorithm was used to extend the seed into an extended assemblage, by pulling additional sequences from different databases (i.e., Hyseq's database containing EST sequences, dbEST version 115, gb pri 115, UniGene version 103, and exons from public domain genomic sequences predicated by GenScan) that belong to this assemblage. The algorithm terminated when there was no additional sequences from the above databases that would extend the assemblage. Inclusion of component sequences into the assemblage was based on a BLASTN hit to the extending assemblage with BLAST score greater than 300 and percent identity greater than 95%.

The nearest neighbor result for the assembled contigs were obtained by a FASTA version 3 search against Genpept release 115, using FASTXY algorithm. FASTXY is an improved version of FASTA alignment which allows in-codon frame shifts. The nearest neighbor result showed the closest homologue for each assemblage from Genpept (and contains the translated amino acid sequences for which the assemblage encodes). The nearest neighbor results is set forth below:

| SEQ ID NO: | Accession No. | Description | Smith-Waterman Score | % Identity |
|---|---|---|---|---|
| 27 | M11313 | Homo sapiens alpha-2-macroglobulin precurser | 133 | 66.667 |

Polypeptides were predicted to be encoded by SEQ ID NO: 2 and SEQ ID NO: 27 as set forth below. The polypeptide was predicted using a software program called FASTY (University of Virginia) which selects a polypeptide based on a comparison of translated novel polynucleotide to known polypeptides (W. R. Pearson, Methods in Enzymology, 183: 63–98 (1990), herein incorporated by reference).

For SEQ ID NO: 2:

| Predicted beginning nucleotide location corresponding to first | Predicted end nucleotide location corresponding to last | AMINO ACID ENCODED BY SEQ ID NO: 2 (A = Alanine, C = Cysteine, D = Aspartic Acid, E = Glutamic Acid, F = Phenylalanine, G = Glycine, H = Histidine, I = Isoleucine, K = Lysine, L = Leucine, M = Methionine, N = Asparagine, P = Proline, |

| amino acid residue of amino acid segment | amino acid residue of amino acid segment | Q = Glutamine, R = Arginine, S = Serine, T = Threonine, V = Valine, W = Tryptophan, Y = Tyrosine, X = Unknown, *Stop Codon, / = possible nucleotide deletion, \ = possible nucleotide insertion) |
|---|---|---|
| 3 | 542 | SSTIRVSGVCYNISFEENKKVLIQRQGNGTFVQTD KPLYTPGQQVYFRIVTMDSNFVPVNDKYSMVEL QDPNSNRIAQWLEVVPEQGIVDLSFQLAPEAMLG TYTVAVAEGKTFGTFSVEEYVLPKFKVEVVEPKE LSTVQESFLVKICCRYTYGKPMLGAVQVSVCQK ANTYWYREVE (SEQ ID NO: 20) |

For SEQ ID NO: 27:

| Predicted beginning nucleotide location corresponding to first amino acid residue of amino acid segment | Predicted end nucleotide location corresponding to last amino acid residue of amino acid segment | AMINO ACID ENCODED BY SEQ ID NO: 2 (A = Alanine, C = Cysteine, D = Aspartic Acid, E = Glutamic Acid, F = Phenylalanine, G = Glycine, H = Histidine, I = Isoleucine, K = Lysine, L = Leucine, M = Methionine, N = Asparagine, P = Proline, Q = Glutamine, R = Arginine, S = Serine, T = Threonine, V = Valine, W = Tryptophan, Y = Tyrosine, X = Unknown, *Stop Codon, / = possible nucleotide deletion, [ ]= possible nucleotide insertion) |
|---|---|---|
| 286 | 393 | SKTTFGFPGYQKELMYKHSNGSYSAFGERDGNG NTW (SEQ ID NO: 40) |

Example 3

Assemblage of SEQ ID NOs: 3–4, and 28–29

Assembly of the novel nucleotide sequence of SEQ ID NO: 3 was accomplished by using an EST sequence SEQ ID NO: 1 as a seed. The seed was extended by gel sequencing (377 Applied Biosystems (ABI) sequencer) using primers to extend the 3' end (primer extension). The 5' end was extended by identifying a full length clone from the mixed tissue library (from trachea, and pituitary gland from Clontech; and from heart, fetal heart, placenta, brain, small intestine, fetal lung, lung, uterus, and fetal brain from Invitrogen) by hybridization to a portion of SEQ ID NO: 1. The DNA from the full length clone was then isolated, sonicated, and recloned for gel sequencing. Each fragment was sequenced by gel sequencing (377 Applied Biosystems (ABI) sequencer) and the sequences were assembled to arrive at the complete sequence.

A polypeptide (SEQ ID NO: 4) was predicted to be encoded by SEQ ID NO: 3 as set forth below. The polypeptide was predicted using a software program called BLASTX which selects a polypeptide based on a comparison of translated novel polynucleotide to known polynucleotides. The initial methionine starts at position 1 of SEQ ID NO: 3 and the putative stop codon, TGA, begins at position 4525 of the nucleotide sequence.

FIGS. 1A, 1B, and 1C show the BLASTX amino acid sequence alignment between the protein encoded by SEQ ID NO: 3 (i.e. SEQ ID NO: 4) alpha-2-macroglobulin-like polypeptide and alpha-2-macroglobulin precursor SEQ ID NO: 23, indicating that the two sequences share 58% similarity over 1494 amino acid residues of SEQ ID NO: 4 and 39% identity over the same 1494 amino acid residues of SEQ ID NO: 4.

FIGS. 2A, 2B, and 2C show the BLASTX amino acid sequence alignment between the protein encoded by SEQ ID NO: 3 (i.e. SEQ ID NO: 4) alpha-2-macroglobulin-like polypeptide and recombinant human alpha-2-macroglobulin, SEQ ID NO: 24, indicating that the two sequences share 58% similarity over 1494 amino acid residues of SEQ ID NO: 4 and 39% identity over the same 1494 amino acid residues of SEQ ID NO: 4.

A predicted approximately seventeen-residue signal peptide is encoded from approximately residue 1 through residue 17 of SEQ ID NO: 4 (SEQ ID NO: 19). The extracellular portion is useful on its own. This can be confirmed by expression in mammalian cells and sequencing of the cleaved product. The signal peptide region was predicted using the Kyte-Doolittle hydrophobocity prediction algorithm (J. Mol Biol, 157, pp. 105–31 (1982), incorporated herein by reference). One of skill in the art will recognize that the actual cleavage site may be different than that predicted by the computer program.

Using eMATRIX software package (Stanford University, Stanford, Calif.) (Wu et al., J. Comp. Biol., vol. 6, pp. 219–235 (1999), herein incorporated by reference), the alpha-2-macroglobulin-like polypeptide of SEQ ID NO: 4 is expected to have twelve alpha-2-macroglobulin signatures as shown in the table. Using eMATRIX software package (Stanford University, Stanford, Calif.) (Wu et al., J. Comp. Biol., vol. 6, pp. 219–235 (1999), herein incorporated by reference), the alpha-2-macroglobulin-like polypeptide of SEQ ID NO: 4 is also expected to have an anaphylatoxin domain proteins domain signature as shown in the table. The domains corresponding to SEQ ID NO: 6–18 are as follows wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine:

| SEQ ID NO | p-value | Signature ID NO | Name | Amino acid sequence encoded (start and end amino acid position) |
|---|---|---|---|---|
| 6 | 3.382e-27 | BL00477J | alpha-2-macroglobulin family thiolester region proteins | IVAWLAKQIHNAYGG FSSTQDTVVALQALA KY (1241–1271) |
| 7 | 8.5e-25 | BL00477F | alpha-2-macroglobulin family thiolester region proteins | AFKPFFVDLTLPYSVV RGESFRLTATIFNY (785–814) |
| 8 | 8.826e-23 | BL00477G | alpha-2-macroglobulin family thiolester region proteins | LVQMPSGCGEQNMV LFAPIIYVLQYLEKAG LL (983–1014) |
| 9 | 9.8e-23 | BL00477A | alpha-2-macroglobulin family thiolester region proteins | TFVQTDKPLYTPGQQ VYFRIVTMDSNFVP (122–150) |
| 10 | 5.5e-16 | BL00477L | alpha-2-macroglobulin family thiolester region proteins | FTISQSVLVTNLKPATI KVYDYYLPGSFKLSQ Y (1437–1469) |
| 11 | 4.529e-14 | BL00477K | alpha-2-macroglobulin family thiolester region proteins | SNMAIVEVKMLSGFS PMEGTNQLL (1382–1405) |
| 12 | 4.541e-13 | BL01177E | anaphylatoxin domain proteins | FVDLTLPYSVVRGESF RLTATIFNYLK (790–816) |
| 13 | 6.538e-13 | BL00477E | alpha-2-macroglobulin family thiolester region proteins | VPDAITEWKAMSFCT SQSRGF (755–775) |
| 14 | 6.625e-13 | BL00477B | alpha-2-macroglobulin family thiolester region proteins | FSVEEYVLPKFKV (209–221) |
| 15 | 2.65e-12 | BL004771 | alpha-2-macroglobulin family thiolester region proteins | WMAGNQLPSGCYAN VGNLLHTAMKGGV (1085–1111) |
| 16 | 4.073e-12 | BL00477D | alpha-2-macroglobulin family thiolester region proteins | RQYFPETWLW (729–738) |
| 17 | 5.395e-12 | BL00477H | alpha-2-macroglobulin family thiolester region proteins | NTWLTAFVTKCF (1054–1065) |
| 18 | 1.161e-10 | BL00477C | alpha-2-macroglobulin family thiolester region proteins | FLVKICCRYTYGKPM LG (236–252) |

Using Molecular Simulations Inc. GeneAtlas software (Molecular Simulations Inc., San Diego, Calif.), alpha-2-macroglobulin-like polypeptide SEQ ID NO: 4 was determined to have a region at residues 977–1276 with characteristic motif for complement component C3d (SEQ ID NO: 21), and at residues 1343–1479 with characteristic motif for receptor domain for alpha-2-macroglobulin domain (SEQ ID NO: 22). The domains corresponding to SEQ ID NO: 21 and 22 are as follows wherein A=Alanine, C=Cysteine, D=Aspartic Acid, E=Glutamic Acid, F=Phenylalanine, G=Glycine, H=Histidine, I=Isoleucine, K=Lysine, L—Leucine, M=Methionine, N=Asparagine, P=Proline, Q=Glutamine, R=Arginine, S=Serine, T=Threonine, V=Valine, W=Tryptophan, Y=Tyrosine:

Complement component C3d homologous sequence

LQNLDGLVQMPSGCGEQNMVLFAPIIYVLQYLEKAGLLTEEIRSRAVGFLEIGYQKELM

YKHSNGSYSAFGERDGNGNTWLTAFVTKCFGQAQKFIFIDPKNIQDALKWMAGNQLPS

GCYANVGNLLHTAMKGGVDDEVSLTAYVTAALLEMGKDVDDPMVSQGLRCLKNSAT

STTNLYTQALLAYIFSLAGEMDIRNILLKQLDQQAIISGESIYWSQKPTPSSNASPWSEPA

AVDVELTAYALLAQLTKPSLTQKEIAKATSIVAWLAKQHNAYGGFSSTQDTVVALQAL

AKYATTAY (designated as SEQ ID NO: 21) with PSI-BLAST e-value of 4.4e-87, protein database identificaiion number entry =1c3d, [Research collaboratory for Structural Bioinformatics.), verify score 0.49, located at residues 977–1276 of SEQ ID NO: 4.

Receptor domain alpha-2-macroglobulin domain

NMKTFSLSVEIGKARCEQPTSPRSLTLTIHTSYVGSRSSSNMAIVEVKMLSGFSPM

EGTNQLLLQQPLVKKVEFGTDTLNIYLDELIKNTQTYTFTISQSVLVTNLKPATIKVYDY

YLPGSFKLSQYTIVWSMNNDS (designated as SEQ ID NO: 22) with PSI-BLAST e-value of 4.4e-52, protein database identification number entry =1bv8, [Research collaboratory for Structural Bioinformatics.), verify score 0.49, located at residues 1349–1479 of SEQ ID NO: 4.

Assembly of the novel nucleotide sequence of SEQ ID NO: 28 was accomplished by using an EST sequence SEQ ID NO: 26 as a seed. The seed was extended by gel sequencing (377 Applied Biosystems (ABI) sequencer) using primers to extend the 3' end (primer extension). Once the end of the clone was reached, the 3' end was completed by blastn comparison of the 3' extended root sequence to public databases and a database of Hyseq clones. The 5' end was initially extended using RACE (Rapid Amplification of cDNA Ends), as, disclosed in Marathon-Ready™ cDNA User Manual (PT1156-1) (Clontech) herein incorporated by reference. The sequence that was obtained at the 5' end of the gene was then further extended by blastn comparison to other clones in the Hyseq proprietary database, and adding the sequence obtained from one of those clones to the 5' end. The remainder of the 5' end was extended using RACE (Rapid Amplification of cDNA Ends), as disclosed in Marathon-Ready™ cDNA User Manual (PT1156-1) (Clontech) herein incorporated by reference.

A polypeptide (SEQ ID NO: 29) was predicted to be encoded by SEQ ID NO: 28 as set forth below. The polypeptide was predicted using a software program called BLASTX which selects a polypeptide based on a comparison of translated novel polynucleotide to known polynucleotides. The initial methionine starts at position 90 of SEQ ID NO: 28 and the putative stop codon, TAG, begins at position 2826 of the nucleotide sequence.

FIGS. 3A and 3B show the BLASTX amino acid sequence alignment between the protein encoded by SEQ ID NO: 28 (i.e. SEQ ID NO: 29) alpha-2-macroglobulin-like polypeptide and ovos_chick ovostatin precursor SEQ ID NO: 41, indicating that the two sequences share 53% similarity and 34% identity over the same amino acid residues of SEQ ID NO: 29. FIGS. 4A and 4B show the BLASTX amino acid sequence alignment between the protein encoded by SEQ ID NO: 28 (i.e. SEQ ID NO: 29) alpha-2-macroglobulin-like polypeptide and the first 812 amino acids of recombinant human alpha-2-macroglobulin in SEQ ID NO: 24, indicating that the two sequences share 53% similarity and 35% identity over the same amino acid residues of SEQ ID NO: 29.

A predicted approximately thirty-residue signal peptide is encoded from approximately residue 1 through residue 30 of SEQ ID NO: 29 (SEQ ID NO: 38). The extracellular portion is useful on its own. This can be confirmed by expression in mammalian cells and sequencing of the cleaved product. The signal peptide region was predicted using the Kyte-Doolittle hydrophobocity prediction algorithm (J. Mol Biol, 157, pp. 105–31 (1982), incorporated herein by reference) and Neural Network SignalP V1.1 program (from Center for Biological Sequence Analysis, The Technical University of Denmark). One of skill in the art will recognize that the actual cleavage site may be different than that predicted by the computer program.

Using eMATRIX software package (Stanford University, Stanford, Calif.) (Wu et al., J. Comp. Biol., vol. 6, pp. 219–235 (1999), herein incorporated by reference), the alpha-2-macroglobulin-like polypeptide of SEQ ID NO: 29 is expected to have six alpha-2-macroglobulin family thiolester regions as shown in the table (SEQ ID NO: 31–32, and 34–37). Using eMATRIX software package (Stanford University, Stanford, Calif.) (Wu et al., J. Comp. Biol., vol. 6, pp. 219–235 (1999), herein incorporated by reference), the alpha-2-macroglobulin-like polypeptide of SEQ ID NO: 29 is also expected to have an anaphylatoxin domain protein signature as shown in the table (SEQ ID NO: 33). The domains corresponding to SEQ ID NO: 31–37 are as follows wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine:

| SEQ ID NO | p-value | Signature ID NO | Name | Amino acid sequence encoded (start and end amino acid position) |
|---|---|---|---|---|
| 31 | 8.500e-25 | BL00477F | alpha-2-macroglobulin family thiolester region proteins | AFKPFFVDLTLPYSVV RGESFRLTATIFNY (799–828) |
| 32 | 9.800e-23 | BL00477A | alpha-2-macroglobulin family thiolester region proteins | TFVQTDKPLYTPGQQ VYFRIVTMDSNFVP (135–163) |
| 34 | 6.538e-13 | BL00477E | alpha-2-macroglobulin family thiolester region proteins | VPDAITEWKAMSFCT SQSRGF (769–789) |
| 35 | 6.625e-13 | BL00477B | alpha-2-macroglobulin family thiolester region proteins | FSVEEYVLPKFKV (222–234) |
| 36 | 4.073e-12 | BL00477D | alpha-2-macroglobulin family thiolester region proteins | RQYFPETWLW (743–752) |

-continued

| SEQ ID NO | p-value | Signature ID NO | Name | Amino acid sequence encoded (start and end amino acid position) |
|---|---|---|---|---|
| 37 | 1.161e-10 | BL00477C | alpha-2-macroglobulin family thiolester region proteins | FLVKICCRYTYGKPM LG (249–265) |
| 33 | 4.541e-13 | BL01177E | anaphylatoxin domain proteins | FVDLTLPYSVVRGESF RLTATIFNYLK (804–830) |

Example 4

A. Expression of SEQ ID NO: 4 or 29 in Cells

Chinese Hamster Ovary (CHO) cells or other suitable cell types are grown in DMEM (ATCC) and 10% fetal bovine serum (FBS) (Gibco) to 70% confluence. Prior to transfection the media is changed to DMEM and 0.5% FCS. Cells are transfected with cDNAs for SEQ ID NO: 3, 5, 28, or 30 or with pBGal vector by the FuGENE-6 transfection reagent (Boehringer). In summary, 4 µl of FuGENE-6 is diluted in 100 µl of DMEM and incubated for 5 minutes. Then, this is added to 1 µg of DNA and incubated for 15 minutes before adding it to a 35 mm dish of CHO cells. The CHO cells are incubated at 37° C. with 5% $CO_2$. After 24 hours, media and cell lysates are collected, centrifuged and dialyzed against assay buffer (15 mM Tris pH 7.6, 134 mM NaCl, 5 mM glucose, 3 mM $CaCl_2$ and $MgCl_2$.

B. Expression Study Using SEQ ID NO: 1–3, 5, 26–28, or 30

The expression of SEQ ID NO: 1–3, 5, 26–28, or 30 in various tissues is analyzed using a semi-quantitative polymerase chain reaction-based technique. Human cDNA libraries are used as sources of expressed genes from tissues of interest (adult bladder, adult brain, adult heart, adult kidney, adult lymph node, adult liver, adult lung, adult ovary, adult placenta, adult rectum, adult spleen, adult testis, bone marrow, thymus, thyroid gland, fetal kidney, fetal liver, fetal liver-spleen, fetal skin, fetal brain, fetal leukocyte and macrophage). Gene-specific primers are used to amplify portions of SEQ ID NO: 1–3, 5, 26–28, or 30 sequence from the samples. Amplified products are separated on an agarose gel, transferred and chemically linked to a nylon filter. The filter is then hybridized with a radioactively labeled ($^{33}$P-dCTP) double-stranded probe generated from SEQ ID NO: 1–3, 5, 26–28, or 30 using a Klenow polymerase, random-prime method. The filters are washed (high stringency) and used to expose a phosphorimaging screen for several hours. Bands indicate the presence of cDNA including SEQ ID NO: 1–3, 5, 26–28, or 30 sequences in a specific library, and thus mRNA expression in the corresponding cell type or tissue.

We claim:

1. An isolated polypeptide consisting of an amino acid sequence of SEQ ID NO: 4, or the mature protein portion thereof.

2. A composition comprising the polypeptide of claim 1 and a carrier.

* * * * *